US005789650A

United States Patent [19]
Lonberg et al.

[11] Patent Number: 5,789,650
[45] Date of Patent: *Aug. 4, 1998

[54] TRANSGENIC NON-HUMAN ANIMALS FOR PRODUCING HETEROLOGOUS ANTIBODIES

[75] Inventors: Nils Lonberg; Robert M. Kay, both of San Francisco, Calif.

[73] Assignee: GenPharm International, Inc., Palo Alto, Calif.

[*] Notice: The term of this patent shall not extend beyond the expiration date of Pat. No. 5,569,825.

[21] Appl. No.: 853,408

[22] Filed: Mar. 18, 1992

Related U.S. Application Data

[63] Continuation-in-part of Ser. No. 834,539, Feb. 5, 1992, Pat. No. 5,633,425, which is a continuation-in-part of Ser. No. 810,279, Dec. 17, 1991, Pat. No. 5,569,825, which is a continuation-in-part of Ser. No. 575,962, Sep. 30, 1990, abandoned, which is a continuation-in-part of Ser. No. 574,748, Aug. 29, 1990, abandoned.

[30] Foreign Application Priority Data

Aug. 28, 1991 [WO] WIPO ............... PCT/US91/06185

[51] Int. Cl.$^6$ ............... C12N 15/00; C07K 16/00; C07H 19/04
[52] U.S. Cl. ............... 800/2; 435/172.3; 530/387.1; 536/26.53; 800/DIG. 1; 800/DIG. 2; 800/DIG. 4
[58] Field of Search ............... 800/2; 536/23.52

[56] References Cited

U.S. PATENT DOCUMENTS 5,175,384  12/1992  Krimpenfort et al. ............... 800/2
5,434,340   7/1995  Krimpenfort et al. ............... 800/2

FOREIGN PATENT DOCUMENTS 9100906  1/1991  WIPO.
9110741  7/1991  WIPO.

OTHER PUBLICATIONS

Declaration Under 37 C.F.R. §1.132 of Diane E. Cox, executed on Aug. 16, 1994.
Durdik et al. PNAS 86: 2346, 1989.
Ichihara et al. EMBO J. 7(13); 4141, 1988.
Humphries et al. Nature 331: 446, 1988.
Zijlstra et al. Nature 342: 435, 1989.
Petterson et al. Nature 344: 165, 1990.
Stites et al. in Basic & Clinical Immunology, p.56, 1984.
Bruggemann et al. PNAS 86: 6709, 1989.
Berman et al. EMBO J 7(3): 727, 1988.
Ferrier et al., "Separate elements control DJ and VDJ rearrangement in a transgenic recombination substrate" The EMBO Journal 9:117–125 (1990).
Nussenzweig et al., "Allelic exclusion in transgenic mice carrying mutant human IgM genes" J. Exp. Med. 167:1969–1974 (1988).
Buttin, Exogenous Ig gene rearrangement in transgenic mice: a new strategy for human monoclonal antibody production? TIG—vol. 3, No. 8 (Aug. 1987).
Hofker et al., Complete physical map of the human immunoglobulin heavy chain constant region gene complex. Proc. Natl. Acad. Sci. USA 86:5567–5571 (1989).
Jaenisch, Transgenic Animals. Science 240:1468–1474 (1988).
Miller et al., Structural alterations in J regions of mouse immunoglobulin λ genes are associated with differential gene expression. Nature 295:428–430 (1982).
Scangos and Bieberich, Gene transfer into mice. Advances in Genetics 24: 285–322 (1987).
Tanaka et al., An antisense oligonucleotide complementary to a sequence in Iγ2b Increase γ2b germline transcrips, stimulates B cell DNA synthesis, and inhibits immunoglobulin secretion, The Journal of Experimental Medicine 175:597–607 (1992).
Vlasov et al., Arrest of immunoglobulin G mRNA translation in vitro with an alkylating antisense oligonucleotide derivative. Chemical Abstracts, p. 28, 112:229433X (1990).
Davis et al. NAR 20(11): 2693, 1992.
Matsuda et al. Nature Genetics 3:88, 1993.
Shon et al. EMBO J 10(12): 3641, 1991.
Pachnes et al. PNAS 87: 5109, 1990.
Pavon et al. Mol. Cell Biol 10(8): 4163, 1990.
Burke et al. Science 236: 806, 1987.
Gaya et al. Science 246: 641, 1989.
Brownstein et al. Science 244: 1348, 1989.
Albertson et al. PNAS 87: 4256, 1990.

(List continued on next page.)

Primary Examiner—Suzanne E. Ziska
Attorney, Agent, or Firm—Townsend and Townsend and Crew LLP

[57] ABSTRACT

The invention relates to transgenic non-human animals capable of producing heterologous antibodies and transgenic non-human animals having inactivated endogenous immunoglobulin genes. In one aspect of the invention, endogenous immunoglobulin genes are suppressed by antisense polynucleotides and/or by antiserum directed against endogenous immunoglobulins. Heterologous antibodies are encoded by immunoglobulin genes not normally found in the genome of that species of non-human animal. In one aspect of the invention, one or more transgenes containing sequences of unrearranged heterologous human immunoglobulin heavy chains are introduced into a non-human animal thereby forming a transgenic animal capable of functionally rearranging transgenic immunoglobulin sequences and producing a repertoire of antibodies of various isotypes encoded by human immunoglobulin genes. Such heterologous human antibodies are produced in B-cells which are thereafter immortalized, e.g., by fusing with an immortalizing cell line such as a myeloma or by manipulating such B-cells by other techniques to perpetuate a cell line capable of producing a monoclonal heterologous antibody. The invention also relates to heavy and light chain immunoglobulin transgenes for making such transgenic non-human animals as well as methods and vectors for disrupting endogenous immunoglobulin loci in the transgenic animal.

5 Claims, 37 Drawing Sheets

OTHER PUBLICATIONS

Gnerhe et al. EMBO J 10(7): 1629, 1991.
Elicieri et al. PNAS 88: 2179, 1991.
Davis et al. Biotechnology 11: 911, 1993.
Chai et al. Nature Genetics 4: 117, 1993.
Jubotsonits et al. Nature 362: 255, 1993.
Marison Nature 368: 812, 1994.
Green et al. Nature Genetics 7: 13, 1994.
Wagner et al. NAR 22(8):1389, 1994.
Traver et al. PNAS 86: 5898, 1989.
Huxley et al. Genetics 9: 742, 1991.

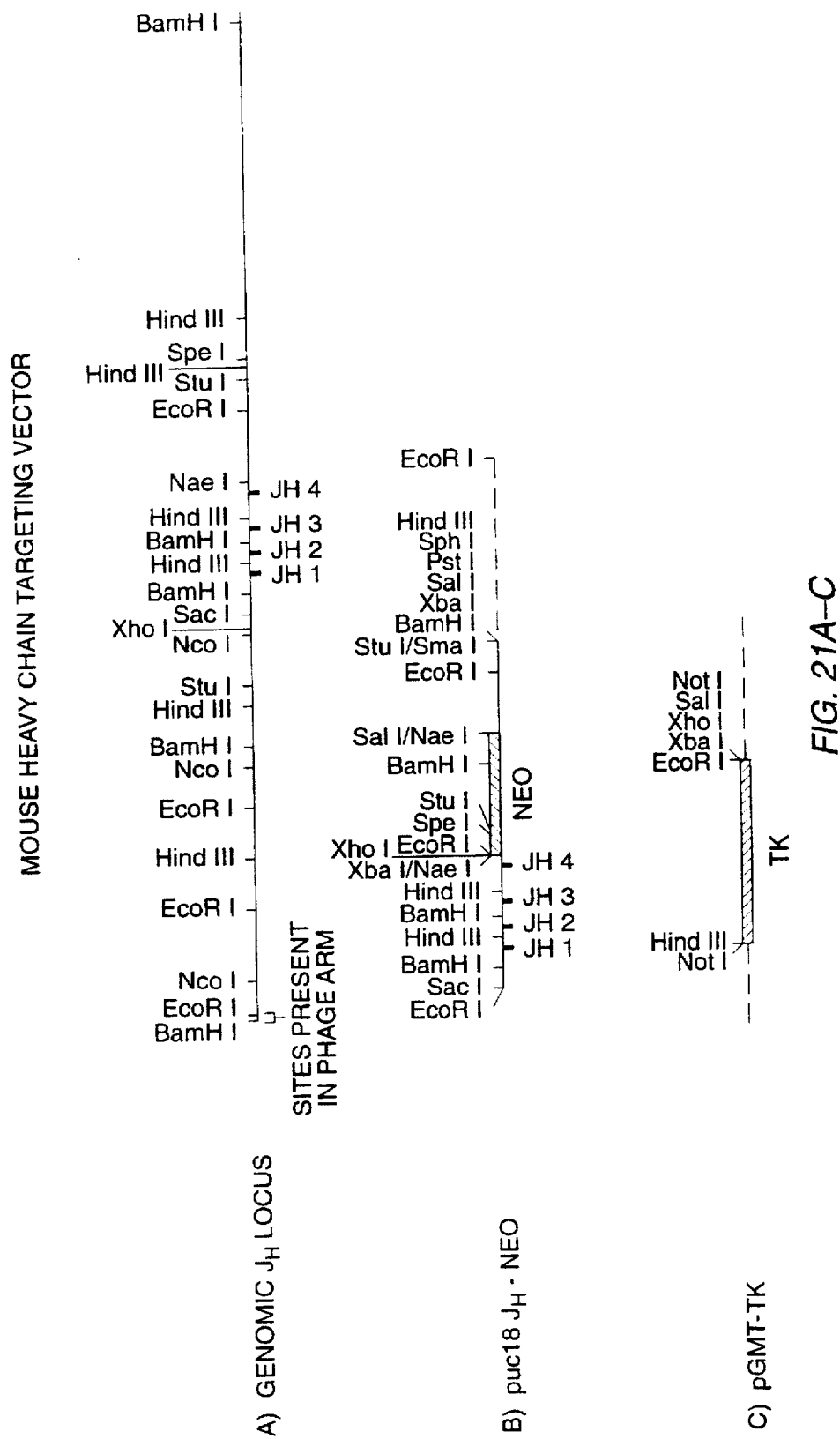
FIG. 21A-C

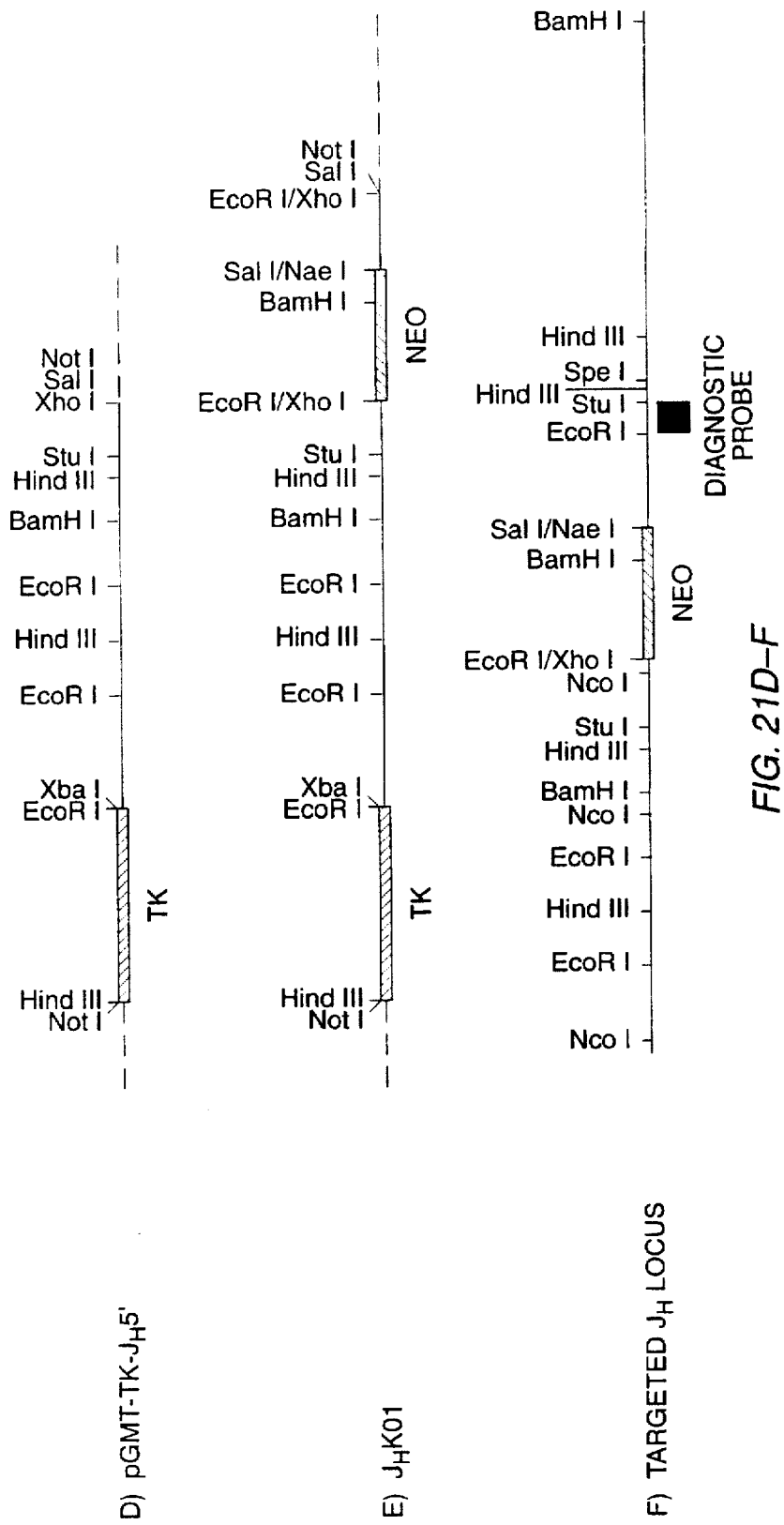

SEQUENCE LISTING ( 1 ) GENERAL INFORMATION:

( i i i ) NUMBER OF SEQUENCES: 150

( 2 ) INFORMATION FOR SEQ ID NO:1:

( i ) SEQUENCE CHARACTERISTICS:
( A ) LENGTH: 10 base pairs
( B ) TYPE: nucleic acid
( C ) STRANDEDNESS: single
( D ) TOPOLOGY: linear ( i i ) MOLECULE TYPE: DNA (primer)

( x i ) SEQUENCE DESCRIPTION: SEQ ID NO:1:

C T A A D T G G G G        1 0

( 2 ) INFORMATION FOR SEQ ID NO:2:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:2:

Asp Ala Phe Asp Ile
1               5

( 2 ) INFORMATION FOR SEQ ID NO:3:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:3:

Asp Tyr Phe Asp Tyr
1               5

( 2 ) INFORMATION FOR SEQ ID NO:4:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:4:

```
    Gly Ala Phe Asp Ile
    1               5
```

( 2 ) INFORMATION FOR SEQ ID NO:5:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

```
    Lys Gly Arg Val
    1
```

( 2 ) INFORMATION FOR SEQ ID NO:6:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

```
    Asn Asp Ser Val
    1
```

( 2 ) INFORMATION FOR SEQ ID NO:7:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:7:

AAAGAAAGAG UU                                                                                           12

( 2 ) INFORMATION FOR SEQ ID NO:8:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:8:

AACGACAGCG UU                                                                                          12

( 2 ) INFORMATION FOR SEQ ID NO:9:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:9:

AATTGCGGCC GC                                                                                          12

( 2 ) INFORMATION FOR SEQ ID NO:10:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:10:

CTTGAGCCCG CCTAATGAGC GGGCTTTTTT TTGCATACTG CGGCC           45

( 2 ) INFORMATION FOR SEQ ID NO:11:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:11:

GCAATGGCCT GGATCCATGG CGCGCTAGCA TCGATATCTA GAGCTCGAGC A      51

( 2 ) INFORMATION FOR SEQ ID NO:12:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:12:

TGCAGATCTG AATTCCCGGG TACCAAGCTT ACGCGTACTA GTGCGGCCGC T      51

( 2 ) INFORMATION FOR SEQ ID NO:13:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:13:

AATTAGCGGC CGCACTAGTA CGCGTAAGCT TGGTACCCGG GAATT           45

( 2 ) INFORMATION FOR SEQ ID NO:14:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:14:

CAGATCTGCA TGCTCGAGCT CTAGATATCG ATGCTAGCGC GCCATGGATC C      51

( 2 ) INFORMATION FOR SEQ ID NO:15:

( i ) SEQUENCE CHARACTERISTICS:
        ( A ) LENGTH: 51 base pairs

-continued (B) TYPE: nucleic acid
(C) STRANDEDNESS: single
(D) TOPOLOGY: linear (ii) MOLECULE TYPE: DNA (primer)

(xi) SEQUENCE DESCRIPTION: SEQ ID NO:15:

AGGCCATTGC GGCCGCAGTA TGCAAAAAAA AGCCCGCTCA TTAGGCGGGC T    51

(2) INFORMATION FOR SEQ ID NO:16:

(i) SEQUENCE CHARACTERISTICS:
    (A) LENGTH: 19 base pairs
    (B) TYPE: nucleic acid
    (C) STRANDEDNESS: single
    (D) TOPOLOGY: linear (ii) MOLECULE TYPE: DNA (primer)

(xi) SEQUENCE DESCRIPTION: SEQ ID NO:16:

CGCGTGGCCG CAATGGCCA    19

(2) INFORMATION FOR SEQ ID NO:17:

(i) SEQUENCE CHARACTERISTICS:
    (A) LENGTH: 19 base pairs
    (B) TYPE: nucleic acid
    (C) STRANDEDNESS: single
    (D) TOPOLOGY: linear (ii) MOLECULE TYPE: DNA (primer)

(xi) SEQUENCE DESCRIPTION: SEQ ID NO:17:

CTAGTGGCCA TTGCGGCCA    19

(2) INFORMATION FOR SEQ ID NO:18:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (ii) MOLECULE TYPE: DNA (primer)

(xi) SEQUENCE DESCRIPTION: SEQ ID NO:18:

CAGGATCCAG ATATCAGTAC CTGAAACAGG GCTTGC    36

(2) INFORMATION FOR SEQ ID NO:19:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (ii) MOLECULE TYPE: DNA (primer)

(xi) SEQUENCE DESCRIPTION: SEQ ID NO:19:

GAGCATGCAC AGGACCTGGA GCACACACAG CCTTCC    36

(2) INFORMATION FOR SEQ ID NO:20:

(i) SEQUENCE CHARACTERISTICS:
    (A) LENGTH: 42 base pairs
    (B) TYPE: nucleic acid
    (C) STRANDEDNESS: single
    (D) TOPOLOGY: linear (ii) MOLECULE TYPE: DNA (primer)

( x i ) SEQUENCE DESCRIPTION: SEQ ID NO:20:

GGACTGTGTC CCTGTGTCAT GCTTTTGATG TCTGGGGCCA AG 42

( 2 ) INFORMATION FOR SEQ ID NO:21:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:21:

CACCAAGTTG ACCTGCCTGG TCACAGACCT GACCACCTAT GA 42

( 2 ) INFORMATION FOR SEQ ID NO:22:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:22:

CCTGTGGACC ACCGCCTCCA CCTTCATCGT CCTCTTCCTC CT 42

( 2 ) INFORMATION FOR SEQ ID NO:23:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:23:

TGAGCCACGA AGACCCTGAG GTCAAGTTCA AGTTCAACTG GTACGTGG 48

( 2 ) INFORMATION FOR SEQ ID NO:24:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:24:

TGGTATTACT ATGGTTCGGG GAGTTATTAT AACCACAGTG TC 42

( 2 ) INFORMATION FOR SEQ ID NO:25:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:25:

GCCTGAAATG GAGCCTCAGG GCACAGTGGG CACGGACACT GT 42

( 2 ) INFORMATION FOR SEQ ID NO:26:

( i ) SEQUENCE CHARACTERISTICS:
     ( A ) LENGTH: 42 base pairs
     ( B ) TYPE: nucleic acid
     ( C ) STRANDEDNESS: single
     ( D ) TOPOLOGY: linear ( i i ) MOLECULE TYPE: DNA (primer)

( x i ) SEQUENCE DESCRIPTION: SEQ ID NO:26:

GCAGGGAGGA CATGTTTAGG ATCTGAGGCC GCACCTGACA CC      4 2

( 2 ) INFORMATION FOR SEQ ID NO:27:

( i ) SEQUENCE CHARACTERISTICS:
     ( A ) LENGTH: 42 base pairs
     ( B ) TYPE: nucleic acid
     ( C ) STRANDEDNESS: single
     ( D , TOPOLOGY: linear ( i i ) MOLECULE TYPE: DNA (primer)

( x i ) SEQUENCE DESCRIPTION: SEQ ID NO:27:

GATCCTGGTT TAGTTAAAGA GGATTTTATT CACCCCTGTG TC      4 2

( 2 ) INFORMATION FOR SEQ ID NO:28:

( i ) SEQUENCE CHARACTERISTICS:
     ( A ) LENGTH: 12 base pairs
     ( B ) TYPE: nucleic acid
     ( C ) STRANDEDNESS: single
     ( D ) TOPOLOGY: linear ( i i ) MOLECULE TYPE: DNA (primer)

( x i ) SEQUENCE DESCRIPTION: SEQ ID NO:28:

GATCCAAGCA GT      1 2

( 2 ) INFORMATION FOR SEQ ID NO:29:

( i ) SEQUENCE CHARACTERISTICS:
     ( A ) LENGTH: 12 base pairs
     ( B ) TYPE: nucleic acid
     ( C ) STRANDEDNESS: single
     ( D ) TOPOLOGY: linear ( i i ) MOLECULE TYPE: DNA (primer)

( x i ) SEQUENCE DESCRIPTION: SEQ ID NO:29:

CTAGACTGCT TG      1 2

( 2 ) INFORMATION FOR SEQ ID NO:30:

( i ) SEQUENCE CHARACTERISTICS:
     ( A ) LENGTH: 12 base pairs
     ( B ) TYPE: nucleic acid
     ( C ) STRANDEDNESS: single
     ( D ) TOPOLOGY: linear ( i i ) MOLECULE TYPE: DNA (primer)

( x i ) SEQUENCE DESCRIPTION: SEQ ID NO:30:

CGCGTCGAAC TA      1 2

( 2 ) INFORMATION FOR SEQ ID NO:31:

( i ) SEQUENCE CHARACTERISTICS:
     ( A ) LENGTH: 12 base pairs (B) TYPE: nucleic acid
(C) STRANDEDNESS: single
(D) TOPOLOGY: linear (ii) MOLECULE TYPE: DNA (primer)

(xi) SEQUENCE DESCRIPTION: SEQ ID NO:31:

AGCTTAGTTC GA                                                                            12

(2) INFORMATION FOR SEQ ID NO:32:

(i) SEQUENCE CHARACTERISTICS:
    (A) LENGTH: 42 base pairs
    (B) TYPE: nucleic acid
    (C) STRANDEDNESS: single
    (D) TOPOLOGY: linear (ii) MOLECULE TYPE: DNA (primer)

(xi) SEQUENCE DESCRIPTION: SEQ ID NO:32:

GAATGGGAGT GAGGCTCTCT CATACCCTAT TCAGAACTGA CT                                            42

(2) INFORMATION FOR SEQ ID NO:33:

(i) SEQUENCE CHARACTERISTICS:
    (A) LENGTH: 42 base pairs
    (B) TYPE: nucleic acid
    (C) STRANDEDNESS: single
    (D) TOPOLOGY: linear (ii) MOLECULE TYPE: DNA (primer)

(xi) SEQUENCE DESCRIPTION: SEQ ID NO:33:

GAACTGTGGC TGCACCATCT GTCTTCATCT TCCCGCCATC TG                                            42

(2) INFORMATION FOR SEQ ID NO:34:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (ii) MOLECULE TYPE: DNA (primer)

(xi) SEQUENCE DESCRIPTION: SEQ ID NO:34:

GAGGTACACT GACATACTGG CATGCCCCCC CCCCCC                                                   36

(2) INFORMATION FOR SEQ ID NO:35:

(i) SEQUENCE CHARACTERISTICS:
    (A) LENGTH: 60 base pairs
    (B) TYPE: nucleic acid
    (C) STRANDEDNESS: single
    (D) TOPOLOGY: linear (ii) MOLECULE TYPE: DNA (primer)

(xi) SEQUENCE DESCRIPTION: SEQ ID NO:35:

GTACGCCATA TCAGCTGGAT GAAGTCATCA GATGGCGGGA AGATGAAGAC AGATGGTGCA                         60

(2) INFORMATION FOR SEQ ID NO:36:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (ii) MOLECULE TYPE: DNA (primer)

( x i ) SEQUENCE DESCRIPTION: SEQ ID NO:36:

TCATCAGATG GCGGGAAGAT GAAGACAGAT GGTGCA                                  36

( 2 ) INFORMATION FOR SEQ ID NO:37:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:37:

GTACGCCATA TCAGCTGGAT GAAG                                               24

( 2 ) INFORMATION FOR SEQ ID NO:38:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:38:

GAGGTACACT GACATACTGG CATG                                               24

( 2 ) INFORMATION FOR SEQ ID NO:39:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:39:

GTACGCCATA TCAGCTGGAT GAAG                                               24

( 2 ) INFORMATION FOR SEQ ID NO:40:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:40:

GAGGTACACT GACATACTGG CATG                                               24

( 2 ) INFORMATION FOR SEQ ID NO:41:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:41:

GTACGCCATA TCAGCTGGAT GAAGACAGGA GACGAGGGGG AAAAGGGTTG GGGCGGATGC        60

( 2 ) INFORMATION FOR SEQ ID NO:42:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:42:

ACAGGAGACG AGGGGGAAAA GGGTTGGGGC GGATGC        36

( 2 ) INFORMATION FOR SEQ ID NO:43:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:43:

GTACGCCATA TCAGCTGGAT GAAG        24

( 2 ) INFORMATION FOR SEQ ID NO:44:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:44:

GAGGTACACT GACATACTGG CATG        24

( 2 ) INFORMATION FOR SEQ ID NO:45:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:45:

GTACTCCATA TCAGCTGGAT GAAG        24

( 2 ) INFORMATION FOR SEQ ID NO:46:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:46:

GAGGTACACT GACATACTGG CATG        24

( 2 ) INFORMATION FOR SEQ ID NO:47:

( i ) SEQUENCE CHARACTERISTICS:
        ( A ) LENGTH: 42 base pairs

```
            ( B ) TYPE: nucleic acid
            ( C ) STRANDEDNESS: single
            ( D ) TOPOLOGY: linear ( i i ) MOLECULE TYPE: DNA (primer)

( x i ) SEQUENCE DESCRIPTION: SEQ ID NO:47:
```

GGCTGATGCT GCACCAACTG TATCCATCTT CCCACCATCC AG                    42

( 2 ) INFORMATION FOR SEQ ID NO:48:

```
    ( i ) SEQUENCE CHARACTERISTICS:
            ( A ) LENGTH: 42 base pairs
            ( B ) TYPE: nucleic acid
            ( C ) STRANDEDNESS: single
            ( D ) TOPOLOGY: linear ( i i ) MOLECULE TYPE: DNA (primer)

( x i ) SEQUENCE DESCRIPTION: SEQ ID NO:48:
```

CTCACGTTCG GTGCTGGGAC CAAGCTGGAG CTGAAACGTA AG                    42

( 2 ) INFORMATION FOR SEQ ID NO:49:

```
    ( i ) SEQUENCE CHARACTERISTICS:
            ( A ) LENGTH: 42 base pairs
            ( B ) TYPE: nucleic acid
            ( C ) STRANDEDNESS: single
            ( D ) TOPOLOGY: linear ( i i ) MOLECULE TYPE: DNA (primer)

( x i ) SEQUENCE DESCRIPTION: SEQ ID NO:49:
```

ACTATGCTAT GGACTACTGG GGTCAAGGAA CCTCAGTCAC CG                    42

( 2 ) INFORMATION FOR SEQ ID NO:50:

```
    ( i ) SEQUENCE CHARACTERISTICS:
            ( A ) LENGTH: 59 base pairs
            ( B ) TYPE: nucleic acid
            ( C ) STRANDEDNESS: single
            ( D ) TOPOLOGY: linear ( i i ) MOLECULE TYPE: DNA (primer)

( x i ) SEQUENCE DESCRIPTION: SEQ ID NO:50:
```

GGCCGCTCGA CGATAGCCTC GAGGCTATAA ATCTAGAAGA ATTCCAGCAA AGCTTTGGC    59

( 2 ) INFORMATION FOR SEQ ID NO:51:

```
    ( i ) SEQUENCE CHARACTERISTICS:
            ( A ) LENGTH: 48 base pairs
            ( B ) TYPE: nucleic acid
            ( C ) STRANDEDNESS: single
            ( D ) TOPOLOGY: linear ( i i ) MOLECULE TYPE: DNA (primer)

( x i ) SEQUENCE DESCRIPTION: SEQ ID NO:51:
```

CAAGAGCCCG CCTAATGAGC GGGCTTTTTT TTGCATACTG CGGCCGCT              48

( 2 ) INFORMATION FOR SEQ ID NO:52:

```
    ( i ) SEQUENCE CHARACTERISTICS:
            ( A ) LENGTH: 48 base pairs
            ( B ) TYPE: nucleic acid
            ( C ) STRANDEDNESS: single
            ( D ) TOPOLOGY: linear ( i i ) MOLECULE TYPE: DNA (primer)
```

( x i ) SEQUENCE DESCRIPTION: SEQ ID NO:52:

AATTAGCGGC CGCAGTATGC AAAAAAAGC CCGCTCATTA GGCGGGCT    48

( 2 ) INFORMATION FOR SEQ ID NO:53:

( i ) SEQUENCE CHARACTERISTICS:
    ( A ) LENGTH: 59 base pairs
    ( B ) TYPE: nucleic acid
    ( C ) STRANDEDNESS: single
    ( D ) TOPOLOGY: linear ( i i ) MOLECULE TYPE: DNA (primer)

( x i ) SEQUENCE DESCRIPTION: SEQ ID NO:53:

GCGGCCGCCT CGAGATCACT ATCGATTAAT TAAGGATCCA GCAGTAAGCT TGCGGCCGC    59

( 2 ) INFORMATION FOR SEQ ID NO:54:

( i ) SEQUENCE CHARACTERISTICS:
    ( A ) LENGTH: 53 base pairs
    ( B ) TYPE: nucleic acid
    ( C ) STRANDEDNESS: single
    ( D ) TOPOLOGY: linear ( i i ) MOLECULE TYPE: DNA (primer)

( x i ) SEQUENCE DESCRIPTION: SEQ ID NO:54:

GCGGCCGCAT CCCGGGTCTC GAGGTCGACA AGCTTTCGAG GATCCGCGGC CGC    53

( 2 ) INFORMATION FOR SEQ ID NO:55:

( i ) SEQUENCE CHARACTERISTICS:
    ( A ) LENGTH: 47 base pairs
    ( B ) TYPE: nucleic acid
    ( C ) STRANDEDNESS: single
    ( D ) TOPOLOGY: linear ( i i ) MOLECULE TYPE: DNA (primer)

( x i ) SEQUENCE DESCRIPTION: SEQ ID NO:55:

GCGGCCGCTG TCGACAAGCT TATCGATGGA TCCTCGAGTG CGGCCGC    47

( 2 ) INFORMATION FOR SEQ ID NO:56:

( i ) SEQUENCE CHARACTERISTICS:
    ( A ) LENGTH: 65 base pairs
    ( B ) TYPE: nucleic acid
    ( C ) STRANDEDNESS: single
    ( D ) TOPOLOGY: linear ( i i ) MOLECULE TYPE: DNA (primer)

( x i ) SEQUENCE DESCRIPTION: SEQ ID NO:56:

GCGGCCGCTG TCGACAAGCT TCGAATTCAG ATCGATGTGG TACCTGGATC CTCGAGTGCG    60

GCCGC    65

( 2 ) INFORMATION FOR SEQ ID NO:57:

( i ) SEQUENCE CHARACTERISTICS:
    ( A ) LENGTH: 51 base pairs
    ( B ) TYPE: nucleic acid
    ( C ) STRANDEDNESS: single
    ( D ) TOPOLOGY: linear ( i i ) MOLECULE TYPE: DNA (primer)

( x i ) SEQUENCE DESCRIPTION: SEQ ID NO:57:

```
GGCCGCAAGC TTACTGCTGG ATCCTTAATT AATCGATAGT GATCTCGAGG C            51
```

( 2 ) INFORMATION FOR SEQ ID NO:58:

( i ) SEQUENCE CHARACTERISTICS:
    ( A ) LENGTH: 51 base pairs
    ( B ) TYPE: nucleic acid
    ( C ) STRANDEDNESS: single
    ( D ) TOPOLOGY: linear ( i i ) MOLECULE TYPE: DNA (primer)

( x i ) SEQUENCE DESCRIPTION: SEQ ID NO:58:

```
GGCCGCCTCG AGATCACTAT CGATTAATTA AGGATCCAGC AGTAAGCTTG C            51
```

( 2 ) INFORMATION FOR SEQ ID NO:59:

( i ) SEQUENCE CHARACTERISTICS:
    ( A ) LENGTH: 39 base pairs
    ( B ) TYPE: nucleic acid
    ( C ) STRANDEDNESS: single
    ( D ) TOPOLOGY: linear ( i i ) MOLECULE TYPE: DNA (primer)

( x i ) SEQUENCE DESCRIPTION: SEQ ID NO:59:

```
CTCCAGGATC CAGATATCAG TACCTGAAAC AGGGCTTGC                          39
```

( 2 ) INFORMATION FOR SEQ ID NO:60:

( i ) SEQUENCE CHARACTERISTICS:
    ( A ) LENGTH: 39 base pairs
    ( B ) TYPE: nucleic acid
    ( C ) STRANDEDNESS: single
    ( D ) TOPOLOGY: linear ( i i ) MOLECULE TYPE: DNA (primer)

( x i ) SEQUENCE DESCRIPTION: SEQ ID NO:60:

```
CTCGAGCATG CACAGGACCT GGAGCACACA CAGCCTTCC                          39
```

( 2 ) INFORMATION FOR SEQ ID NO:61:

( i ) SEQUENCE CHARACTERISTICS:
    ( A ) LENGTH: 813 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: CDS
    ( B ) LOCATION: 241..285

( i x ) FEATURE:
    ( A ) NAME/KEY: CDS
    ( B ) LOCATION: 373..678

( x i ) SEQUENCE DESCRIPTION: SEQ ID NO:61:

```
TTCCTCAGGC AGGATTTAGG GCTTGGTCTC TCAGCATCCC ACACTTGTAC AGCTGATGTG   60
GCATCTGTGT TTTCTTTCTC ATCCTAGATC AAGCTTTGAG CTGTGAAATA CCCTGCCTCA  120
TGAATATGCA AATAATCTGA GGTCTTCTGA GATAAATATA GATATATTGG TGCCCTGAGA  180
GCATCACATA ACAACCAGAT TCCTCCTCTA AAGAAGCCCC TGGGAGCACA GCTCATCACC  240
ATG GAC TGG ACC TGG AGG TTC CTC TTT GTG GTG GCA GCA GCT ACA        285
Met Asp Trp Thr Trp Arg Phe Leu Phe Val Val Ala Ala Ala Thr
 1               5                  10                  15
```

```
GGTAAGGGGC TTCCTAGTCC CTAAGGCTGA GGAAGGGATC CTGGTTTAGT TAAAGAGGAT           345

TTTATTCACC CCTGTGTCCT CTCCACA GGT GTC CAG TCC CAG GTC CAG CTG              396
                                Gly Val Gln Ser Gln Val Gln Leu
                                 1               5

GTG CAG TCT GGG GCT GAG GTG AAG AAG CCT GGG TCC TCG GTG AAG GTC            444
Val Gln Ser Gly Ala Glu Val Lys Lys Pro Gly Ser Ser Val Lys Val
         10              15                  20

TCC TGC AAG GCT TCT GGA GGC ACC TTC AGC AGC TAT GCT ATC AGC TGG            492
Ser Cys Lys Ala Ser Gly Gly Thr Phe Ser Ser Tyr Ala Ile Ser Trp
 25              30                  35                      40

GTG CGA CAG GCC CCT GGA CAA GGG CTT GAG TGG ATG GGA AGG ATC ATC            540
Val Arg Gln Ala Pro Gly Gln Gly Leu Glu Trp Met Gly Arg Ile Ile
                 45                  50                      55

CCT ATC CTT GGT ATA GCA AAC TAC GCA CAG AAG TTC CAG GGC AGA GTC            588
Pro Ile Leu Gly Ile Ala Asn Tyr Ala Gln Lys Phe Gln Gly Arg Val
             60                  65                  70

ACG ATT ACC GCG GAC AAA TCC ACG AGC ACA GCC TAC ATG GAG CTG AGC            636
Thr Ile Thr Ala Asp Lys Ser Thr Ser Thr Ala Tyr Met Glu Leu Ser
         75                  80                  85

AGC CTG AGA TCT GAG GAC ACG GCC GTG TAT TAC TGT GCG AGA                    678
Ser Leu Arg Ser Glu Asp Thr Ala Val Tyr Tyr Cys Ala Arg
     90                  95                 100

GACACAGTGT GAAAACCCAC ATCCTGAGAG TGTCAGAAAC CCTGAGGGAG AAGGCAGCTG          738

TGCCGGGCTG AGGAGATGAC AGGGTTTATT AGGTTTAAGG CTGTTTACAA AATGGGTTAT          798

ATATTGAGA AAAAA                                                            813
```

( 2 ) INFORMATION FOR SEQ ID NO:62:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: protein ( x i ) SEQUENCE DESCRIPTION: SEQ ID NO:62:

```
Met Asp Trp Thr Trp Arg Phe Leu Phe Val Val Ala Ala Ala Thr
 1               5                  10                  15
```

( 2 ) INFORMATION FOR SEQ ID NO:63:

( i ) SEQUENCE CHARACTERISTICS:
        ( A ) LENGTH: 102 amino acids
        ( B ) TYPE: amino acid
        ( D ) TOPOLOGY: linear ( i i ) MOLECULE TYPE: protein ( x i ) SEQUENCE DESCRIPTION: SEQ ID NO:63:

```
Gly Val Gln Ser Gln Val Gln Leu Val Gln Ser Gly Ala Glu Val Lys
 1               5                  10                  15

Lys Pro Gly Ser Ser Val Lys Val Ser Cys Lys Ala Ser Gly Gly Thr
             20                  25                  30

Phe Ser Ser Tyr Ala Ile Ser Trp Val Arg Gln Ala Pro Gly Gln Gly
         35                  40                  45

Leu Glu Trp Met Gly Arg Ile Ile Pro Ile Leu Gly Ile Ala Asn Tyr
     50                  55                  60

Ala Gln Lys Phe Gln Gly Arg Val Thr Ile Thr Ala Asp Lys Ser Thr
 65                  70                  75                  80

Ser Thr Ala Tyr Met Glu Leu Ser Ser Leu Arg Ser Glu Asp Thr Ala
                 85                  90                  95
```

Val Tyr Tyr Cys Ala Arg
                100

( 2 ) INFORMATION FOR SEQ ID NO:64:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:64:

GGACTGTGTC CCTGTGTGAT GCTTTTGATG TCTGGGGCCA AG　　　　　　　42

( 2 ) INFORMATION FOR SEQ ID NO:65:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:65:

CACCAAGTTG ACCTGCCTGG TCACAGACCT GACCACCTAT GA　　　　　　　42

( 2 ) INFORMATION FOR SEQ ID NO:66:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:66:

TGGTATTACT ATGGTTCGGG GAGTTATTAT AACCACAGTG TC　　　　　　　42

( 2 ) INFORMATION FOR SEQ ID NO:67:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:67:

CAGCAGGTGC ACACCCAATG CCCATGAGCC CAGACACTGG AC　　　　　　　42

( 2 ) INFORMATION FOR SEQ ID NO:68:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:68:

TGAGCCCAGA CACTGGAC　　　　　　　18

( 2 ) INFORMATION FOR SEQ ID NO:69:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:69:

GTTAAAGAGG ATTTTATTCA CCCCTGTGTC CTCTCCACAG GTGTC     45

( 2 ) INFORMATION FOR SEQ ID NO:70:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:70:

CCGGTCGACC GG     12

( 2 ) INFORMATION FOR SEQ ID NO:71:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:71:

Tyr Cys Ala Arg Arg Leu Thr Gly Val Asp Ala Phe Asp Ile Trp Gly
1               5                      10                  15

Gln Gly Thr Met Val Thr Val Ser Ser Ala Ser Thr Lys
             20                  25

( 2 ) INFORMATION FOR SEQ ID NO:72:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:72:

Tyr Cys Ala Arg His Arg Ile Ala Ala Ala Gly Phe Asp Tyr Trp Gly
1               5                      10                  15

Gln Gly Thr Leu Val Thr Val Ser Ser Ala Ser Thr Lys
             20                  25

( 2 ) INFORMATION FOR SEQ ID NO:73:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:73:

-continued

Tyr Cys Ala Arg Tyr Tyr Tyr Tyr Tyr Gly Met Asp Val Trp Gly
1               5                   10                  15

Gln Gly Thr Thr Val Thr Val Ser Ser Ala Ser Thr Lys
            20              25

(2) INFORMATION FOR SEQ ID NO:74:

(i) SEQUENCE CHARACTERISTICS:
      (A) LENGTH: 34 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:74:

Tyr Cys Ala Arg His Tyr Asp Ile Leu Thr Gly Pro Thr Thr Thr
1               5                   10                  15

Val Trp Thr Ser Gly Ala Lys Gly Pro Arg Ser Pro Ser Pro Gln Pro
            20                  25                  30

Pro Pro (2) INFORMATION FOR SEQ ID NO:75:

(i) SEQUENCE CHARACTERISTICS:
      (A) LENGTH: 34 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:75:

Tyr Cys Ala Arg Arg Arg Tyr Tyr Gly Ser Gly Ser Tyr Tyr Asn Val
1               5                   10                  15

Phe Asp Tyr Trp Gly Gln Gly Thr Leu Val Thr Val Ser Ser Ala Ser
            20                  25                  30

Thr Lys (2) INFORMATION FOR SEQ ID NO:76:

(i) SEQUENCE CHARACTERISTICS:
      (A) LENGTH: 28 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:76:

Tyr Cys Ala Arg Arg Gly Val Ser Asp Ala Phe Asp Ile Trp Gly Gln
1               5                   10                  15

Gly Thr Met Val Thr Val Ser Ser Ala Ser Thr Lys
            20                  25

(2) INFORMATION FOR SEQ ID NO:77:

(i) SEQUENCE CHARACTERISTICS:
      (A) LENGTH: 26 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:77:

```
Tyr Cys Ala Arg Ala Thr Gly Ala Phe Asp Ile Trp Gly Gln Gly Thr
1               5                   10                  15

Met Val Thr Val Ser Ser Gly Ser Ala Ser
            20                  25
```

( 2 ) INFORMATION FOR SEQ ID NO:78:

( i ) SEQUENCE CHARACTERISTICS:
        ( A ) LENGTH: 33 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:78:

```
Tyr Cys Ala Arg Ser Ala Asn Trp Gly Ser Tyr Tyr Tyr Tyr Gly Met
1               5                   10                  15

Asp Val Trp Gly Gln Gly Thr Met Val Thr Val Ser Ser Gly Ser Ala
                20                  25                  30

Ser
```

( 2 ) INFORMATION FOR SEQ ID NO:79:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:79:

```
Tyr Cys Ala Arg Tyr Phe Gly His Trp Gly Gln Gly Thr Leu Val Thr
1               5                   10                  15

Val Ser Ser Gly Ser Ala Ser
            20
```

( 2 ) INFORMATION FOR SEQ ID NO:80:

( i ) SEQUENCE CHARACTERISTICS:
        ( A ) LENGTH: 27 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:80:

```
Tyr Cys Ala Arg His Val Ala Asn Ser Phe Asp Tyr Trp Gly Gln Gly
1               5                   10                  15

Thr Leu Val Thr Val Ser Ser Gly Ser Ala Ser
            20                  25
```

( 2 ) INFORMATION FOR SEQ ID NO:81:

( i ) SEQUENCE CHARACTERISTICS:
        ( A ) LENGTH: 31 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:81:

```
Tyr Cys Ala Arg Gln Ile Thr Met Val Arg Gly Val Pro Phe Asp Tyr
1               5                   10                  15
```

```
            Trp Gly Gln Gly Thr Leu Val Thr Val Ser Ser Gly Ser Ala Ser
                        20                  25                  30
```

( 2 ) INFORMATION FOR SEQ ID NO:82:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:82:

```
    Tyr Cys Ala Arg Gln Tyr Phe Gln His Trp Gly Gln Gly Thr Leu Val
    1               5                   10                  15

Thr Val Ser Ser Gly Ser Ala Ser
                    20
```

( 2 ) INFORMATION FOR SEQ ID NO:83:

( i ) SEQUENCE CHARACTERISTICS:
        ( A ) LENGTH: 31 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:83:

```
    Tyr Cys Ala Arg Gln Thr Gly Asp Tyr Tyr Tyr Gly Met Asp Val
    1               5                   10                  15

Trp Gly Gln Gly Thr Thr Val Thr Val Ser Ser Gly Ser Ala Ser
                    20                  25                  30
```

( 2 ) INFORMATION FOR SEQ ID NO:84:

( i ) SEQUENCE CHARACTERISTICS:
        ( A ) LENGTH: 36 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:84:

```
    Tyr Cys Ala Arg His Tyr Tyr Gly Ser Gly Ser Tyr Asp Tyr Tyr Tyr
    1               5                   10                  15

Tyr Gly Met Asp Val Trp Gly Gln Gly Thr Thr Val Thr Val Ser Ser
                    20                  25                  30

Gly Ser Ala Ser
                35
```

( 2 ) INFORMATION FOR SEQ ID NO:85:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:85:

```
    Tyr Cys Ala Arg Gln Gly Val Gly Pro Gly Asn Pro Gly His Arg Leu
    1               5                   10                  15
```

Leu Ser Leu His Gln
               20

( 2 ) INFORMATION FOR SEQ ID NO:86:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:86:

Tyr Cys Ala Arg Phe Thr Glu Thr Gly Ser Thr Pro Gly Ala Arg Glu
1               5                   10                  15

Pro Trp Ser Pro Ser Pro Gln Gly Val His
            20                  25

( 2 ) INFORMATION FOR SEQ ID NO:87:

( i ) SEQUENCE CHARACTERISTICS:
        ( A ) LENGTH: 34 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:87:

Tyr Cys Ala Arg Arg Arg Tyr Tyr Gly Ser Gly Ser Tyr Tyr Asn Val
1               5                   10                  15

Phe Asp Tyr Trp Gly Gln Gly Thr Leu Val Thr Val Ser Ser Ala Ser
            20                  25                  30

Thr Lys ( 2 ) INFORMATION FOR SEQ ID NO:88:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:88:

Tyr Cys Ala Arg Gln Thr Trp Gly Gly Asp Tyr Trp Gly Gln Gly Thr
1               5                   10                  15

Leu Val Thr Val Ser Ser Ala Ser Thr Lys
            20                  25

( 2 ) INFORMATION FOR SEQ ID NO:89:

( i ) SEQUENCE CHARACTERISTICS:
        ( A ) LENGTH: 33 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:89:

Tyr Cys Ala Arg Gly Tyr Ser Gly Tyr Asp Asn Tyr Tyr Tyr Gly Ile
1               5                   10                  15

His Val Trp Gly Gln Gly Thr Thr Val Thr Val Ser Ser Ala Ser Thr
            20                  25                  30

Lys ( 2 ) INFORMATION FOR SEQ ID NO:90:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:90:

```
Tyr Cys Ala Arg Gln Thr Gly Glu Asp Tyr Phe Asp Tyr Trp Gly Gln
 1               5                  10                  15
Gly Thr Leu Val Thr Val Ser Ser Gly Ser Ala Ser
            20                  25
```

( 2 ) INFORMATION FOR SEQ ID NO:91:

( i ) SEQUENCE CHARACTERISTICS:
        ( A ) LENGTH: 31 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:91:

```
Tyr Cys Ala Arg Tyr Ser Gly Tyr Asp Tyr Leu Leu Val Leu Arg Ser
 1               5                  10                  15
Leu Gly Pro Trp His Pro Gly His Cys Leu Leu Ser Leu His Arg
            20                  25                  30
```

( 2 ) INFORMATION FOR SEQ ID NO:92:

( i ) SEQUENCE CHARACTERISTICS:
        ( A ) LENGTH: 32 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:92:

```
Tyr Cys Ala Arg Ala Ser Leu Pro Ser Phe Asp Tyr Tyr Gly Met Asp
 1               5                  10                  15
Val Trp Gly Gln Gly Thr Thr Val Thr Val Ser Ser Ala Ser Thr Lys
            20                  25                  30
```

( 2 ) INFORMATION FOR SEQ ID NO:93:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:93:

```
Tyr Cys Ala Arg Arg Gly Gly Gly Leu Thr Thr Gly Ala Arg Glu Pro
 1               5                  10                  15
Trp Ser Pro Ser Pro Gln Gly Val His
            20                  25
```

( 2 ) INFORMATION FOR SEQ ID NO:94:

( i ) SEQUENCE CHARACTERISTICS:
        ( A ) LENGTH: 31 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:94:

```
Tyr Cys Val Pro Val Glu Thr Leu Leu Leu Leu Leu Arg Tyr Arg
1               5                   10                  15
Leu Gly Pro Arg Asp His Gly His Arg Leu leu Arg Glu Cys Ile
            20                  25                  30
```

( 2 ) INFORMATION FOR SEQ ID NO:95:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:95:

```
Tyr Cys Val Arg Asp Ile Leu Thr Gly Glx Arg Asp Tyr Trp Gly Gln
1               5                   10                  15
Gly Thr Leu Val Thr Val Ser Ser Gly Ser Ala Ser
            20                  25
```

( 2 ) INFORMATION FOR SEQ ID NO:96:

( i ) SEQUENCE CHARACTERISTICS:
        ( A ) LENGTH: 31 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:96:

```
Tyr Cys Ala Arg His Gly Ile Ala Ala Ala Gly Thr Ala Phe Asp Ile
1               5                   10                  15
Trp Gly Gln Gly Thr Met Val Thr Val Ser Ser Gly Ser Ala Ser
            20                  25                  30
```

( 2 ) INFORMATION FOR SEQ ID NO:97:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:97:

```
Tyr Cys Val Arg Ser Thr Gly Val Asp Ala Phe Asp Ile Trp Gly Gln
1               5                   10                  15
Gly Thr Met Val Thr Val Ser Ser Gly Ser Ala Ser
            20                  25
```

( 2 ) INFORMATION FOR SEQ ID NO:98:

( i ) SEQUENCE CHARACTERISTICS:
        ( A ) LENGTH: 28 amino acids (B) TYPE: amino acid
(C) STRANDEDNESS: single
(D) TOPOLOGY: linear (ii) MOLECULE TYPE: peptide (xi) SEQUENCE DESCRIPTION: SEQ ID NO:98:

Tyr Cys Ala Glu Ile Ala Ala Ala Ala Leu Leu Glx Leu Leu Gly Pro
1               5                   10                  15

Gly Met Pro Gly His Arg Leu Leu Arg Glu Cys Ile
            20              25

(2) INFORMATION FOR SEQ ID NO:99:

(i) SEQUENCE CHARACTERISTICS:
    (A) LENGTH: 29 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:99:

Tyr Cys Val Cys Ile Ala Ala Ala Gly Asn Gly Asn Gly Tyr Trp Gly
1               5                   10                  15

Gln Gly Thr Leu Val Thr Val Ser Ser Gly Ser Ala Ser
            20              25

(2) INFORMATION FOR SEQ ID NO:100:

(i) SEQUENCE CHARACTERISTICS:
    (A) LENGTH: 25 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:100:

Tyr Cys Ala Arg Gln Met Met Gly Asp Tyr Trp Gly Gln Gly Thr Leu
1               5                   10                  15

Val Thr Val Ser Ser Gly Ser Ala Ser
            20              25

(2) INFORMATION FOR SEQ ID NO:101:

(i) SEQUENCE CHARACTERISTICS:
    (A) LENGTH: 39 base pairs
    (B) TYPE: nucleic acid
    (C) STRANDEDNESS: single
    (D) TOPOLOGY: linear (ii) MOLECULE TYPE: DNA (primer)

(xi) SEQUENCE DESCRIPTION: SEQ ID NO:101:

CTAGCTCGAG TCCAAGGAGT CTGTGCCGAG GTGCAGCTG                    39

(2) INFORMATION FOR SEQ ID NO:102:

(i) SEQUENCE CHARACTERISTICS:
    (A) LENGTH: 39 base pairs
    (B) TYPE: nucleic acid
    (C) STRANDEDNESS: single
    (D) TOPOLOGY: linear (ii) MOLECULE TYPE: DNA (primer)

(xi) SEQUENCE DESCRIPTION: SEQ ID NO:102:

GTTGCTCGAG TGAAAGGTGT CCAGTGTGAG GTGCAGCTG                    39

( 2 ) INFORMATION FOR SEQ ID NO:103:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:103:

GGCGCTCGAG TTCCACGACA CCGTCACCGG TTC                          33

( 2 ) INFORMATION FOR SEQ ID NO:104:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:104:

CCTGCTCGAG GCAGCCAACG GCCACGCTGC TCG                          33

( 2 ) INFORMATION FOR SEQ ID NO:105:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:105:

TCAGTGAAGG TTTCCTGCAA GGCATCTGGA TACACCTTCA CC                42

( 2 ) INFORMATION FOR SEQ ID NO:106:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:106:

TCCCTGAGAC TCTCCTGTGC AGCCTCTGGA TTCACCTTCA GT                42

( 2 ) INFORMATION FOR SEQ ID NO:107:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:107:

GGCCGCATCC CGGGTCTCGA GGTCGACAAG CTTTCGAGGA TCCGC             45

( 2 ) INFORMATION FOR SEQ ID NO:108:

( i ) SEQUENCE CHARACTERISTICS:
    ( A ) LENGTH: 45 base pairs
    ( B ) TYPE: nucleic acid
    ( C ) STRANDEDNESS: single
    ( D ) TOPOLOGY: linear ( i i ) MOLECULE TYPE: DNA (primer)

( x i ) SEQUENCE DESCRIPTION: SEQ ID NO:108:

GGCCGCGGAT CCTCGAAAGC TTGTCGACCT CGAGACCCGG GATGC    45

( 2 ) INFORMATION FOR SEQ ID NO:109:

( i ) SEQUENCE CHARACTERISTICS:
    ( A ) LENGTH: 39 base pairs
    ( B ) TYPE: nucleic acid
    ( C ) STRANDEDNESS: single
    ( D ) TOPOLOGY: linear ( i i ) MOLECULE TYPE: DNA (primer)

( x i ) SEQUENCE DESCRIPTION: SEQ ID NO:109:

GGCCGCTGTC GACAAGCTTA TCGATGGATC CTCGAGTGC    39

( 2 ) INFORMATION FOR SEQ ID NO:110:

( i ) SEQUENCE CHARACTERISTICS:
    ( A ) LENGTH: 39 base pairs
    ( B ) TYPE: nucleic acid
    ( C ) STRANDEDNESS: single
    ( D ) TOPOLOGY: linear ( i i ) MOLECULE TYPE: DNA (primer)

( x i ) SEQUENCE DESCRIPTION: SEQ ID NO:110:

GGCCGCACTC GAGGATCCAT CGATAAGCTT GTCGACAGC    39

( 2 ) INFORMATION FOR SEQ ID NO:111:

( i ) SEQUENCE CHARACTERISTICS:
    ( A ) LENGTH: 42 base pairs
    ( B ) TYPE: nucleic acid
    ( C ) STRANDEDNESS: single
    ( D ) TOPOLOGY: linear ( i i ) MOLECULE TYPE: DNA (primer)

( x i ) SEQUENCE DESCRIPTION: SEQ ID NO:111:

CACCTTCGGC CAAGGGACAC GACTGGAGAT TAAACGTAAG CA    42

( 2 ) INFORMATION FOR SEQ ID NO:112:

( i ) SEQUENCE CHARACTERISTICS:
    ( A ) LENGTH: 48 base pairs
    ( B ) TYPE: nucleic acid
    ( C ) STRANDEDNESS: single
    ( D ) TOPOLOGY: linear ( i i ) MOLECULE TYPE: DNA (primer)

( x i ) SEQUENCE DESCRIPTION: SEQ ID NO:112:

AGGTTCAGTG GCAGTGGGTC TGGGACAGAC TTCACTCTCA CCATCAGC    48

( 2 ) INFORMATION FOR SEQ ID NO:113:

( i ) SEQUENCE CHARACTERISTICS:
    ( A ) LENGTH: 12 base pairs
    ( B ) TYPE: nucleic acid
    ( C ) STRANDEDNESS: single
    ( D ) TOPOLOGY: linear ( i i ) MOLECULE TYPE: DNA (primer)

( x i ) SEQUENCE DESCRIPTION: SEQ ID NO:113:

AATTGCGGCC GC                                                                                   12

( 2 ) INFORMATION FOR SEQ ID NO:114:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:114:

GATCCTCGAG ACCAGGTACC AGATCTTGTG AATTCG                                                         36

( 2 ) INFORMATION FOR SEQ ID NO:115:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:115:

TCGACGAATT CACAAGATCT GGTACCTGGT CTCGAG                                                         36

( 2 ) INFORMATION FOR SEQ ID NO:116:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:116:

CGCGGTACCG AGAGTCAGTC CTTCCCAAAT GTC                                                            33

( 2 ) INFORMATION FOR SEQ ID NO:117:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:117:

CGCCTCGAGA CAGCTGGAAT GGGCACATGC AGA                                                            33

( 2 ) INFORMATION FOR SEQ ID NO:118:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:118:

CGCGGTACCG CTGATGCTGC ACCAACTGTA TCC    33

( 2 ) INFORMATION FOR SEQ ID NO:119:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:119:

CGCCTCGAGC TAACACTCAT TCCTGTTGAA GCT    33

( 2 ) INFORMATION FOR SEQ ID NO:120:

( i ) SEQUENCE CHARACTERISTICS:
        ( A ) LENGTH: 3699 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:120:

```
AATTAGCGGC CGCCTCGAGA TCACTATCGA TTAATTAAGG ATCCAGATAT CAGTACCTGA    60
AACAGGGCTT GCTCACAACA TCTCTCTCTC TGTCTCTCTG TCTCTGTGTG TGTGTCTCTC   120
TCTGTCTCTG TCTCTCTCTG TCTCTCTGTC TCTGTGTGTG TCTCTCTCTG TCTCTCTCTC   180
TGTCTCTCTG TCTCTCTGTC TGTCTCTGTC TCTGTCTCTG TCTCTCTCTC TCTCTCTCTC   240
TCTCTCTCTC TCTCTCTCAC ACACACACAC ACACACACAC ACACCTGC  CGAGTGACTC     300
ACTCTGTGCA GGGTTGGCCC TCGGGCACA  TGCAAATGGA TGTTTGTTCC ATGCAGAAAA    360
ACATGTTTCT CATTCTCTGA GCCAAAAATA GCATCAATGA TTCCCCACC  CTGCAGCTGC    420
AGGTTCACCC CACCTGGCCA GGTTGACCAG CTTTGGGGAT GGGGCTGGGG GTTCCATGAC    480
CCCTAACGGT GACATTGAAT TCAGTGTTTT CCCATTTATC GACACTGCTG GAATCTGACC    540
CTAGGAGGGA ATGACAGGAG ATAGGCAAGG TCCAAACACC CCAGGGAAGT GGGAGAGACA    600
GGAAGGCTGT GTGTGCTCCA GGTCCTGTGC ATGCTGCAGA TCTGAATTCC CGGGTACCAA    660
GCTTGCGGCC GCAGTATGCA AAAAAAGCC  CGCTCATTAG GCGGGCTCTT GGCAGAACAT    720
ATCCATCGCG TCCGCCATCT CCAGCAGCCG CACGCGGCGC ATCTCGGGCA GCGTTGGGTC    780
CTGGCCACGG GTGCGCATGA TCGTGCTCCT GTCGTTGAGG ACCCGGCTAG GCTGGCGGGG    840
TTGCCTTACT GGTTAGCAGA ATGAATCACC GATACGCGAG CGAACGTGAA GCGACTGCTG    900
CTGCAAAACG TCTGCGACCT GAGCAACAAC ATGAATGGTC TTCGGTTTCC GTGTTTCGTA    960
AAGTCTGGAA ACGCGGAAGT CAGCGCCCTG CACCATTATG TTCCGGATCT GCATCGCAGG   1020
ATGCTGCTGG CTACCCTGTG GAACACCTAC ATCTGTATTA ACGAAGCGCT GGCATTGACC   1080
CTGAGTGATT TTCTCTGGT  CCCGCCGCAT CCATACCGCC AGTTGTTTAC CCTCACAACG   1140
TTCCAGTAAC CGGGCATGTT CATCATCAGT AACCCGTATC GTGAGCATCC TCTCTCGTTT   1200
CATCGGTATC ATTACCCCCA TGAACAGAAA TTCCCCCTTA CACGGAGGCA TCAAGTGACC   1260
AAACAGGAAA AAACCGCCCT TAACATGGCC CGCTTTATCA GAAGCCAGAC ATTAACGCTT   1320
CTGGAGAAAC TCAACGAGCT GGACGCGGAT GAACAGGCAG ACATCTGTGA ATCGCTTCAC   1380
GACCACGCTG ATGAGCTTTA CCGCAGCTGC CTCGCGCGTT TCGGTGATGA CGGTGAAAAC   1440
CTCTGACACA TGCAGCTCCC GGAGACGGTC ACAGCTTGTC TGTAAGCGGA TGCCGGGAGC   1500
```

-continued

| | | | | | |
|---|---|---|---|---|---|
| AGACAAGCCC | GTCAGGGCGC | GTCAGCGGGT | GTTGGCGGGT | GTCGGGGCGC | AGCCATGACC | 1560
| CAGTCACGTA | GCGATAGCGG | AGTGTATACT | GGCTTAACTA | TGCGGCATCA | GAGCAGATTG | 1620
| TACTGAGAGT | GCACCATATG | CGGTGTGAAA | TACCGCACAG | ATGCGTAAGG | AGAAAATACC | 1680
| GCATCAGGCG | CTCTTCCGCT | TCCTCGCTCA | CTGACTCGCT | GCGCTCGGTC | GTTCGGCTGC | 1740
| GGCGAGCGGT | ATCAGCTCAC | TCAAAGGCGG | TAATACGGTT | ATCCACAGAA | TCAGGGGATA | 1800
| ACGCAGGAAA | GAACATGTGA | GCAAAAGGCC | AGCAAAAGGC | CAGGAACCGT | AAAAAGGCCG | 1860
| CGTTGCTGGC | GTTTTCCAT | AGGCTCCGCC | CCCTGACGA | GCATCACAAA | AATCGACGCT | 1920
| CAAGTCAGAG | GTGGCGAAAC | CCGACAGGAC | TATAAAGATA | CCAGGCGTTT | CCCCCTGGAA | 1980
| GCTCCCTCGT | GCGCTCTCCT | GTTCCGACCC | TGCCGCTTAC | CGGATACCTG | TCCGCCTTTC | 2040
| TCCCTTCGGG | AAGCGTGGCG | CTTTCTCATA | GCTCACGCTG | TAGGTATCTC | AGTTCGGTGT | 2100
| AGGTCGTTCG | CTCCAAGCTG | GGCTGTGTGC | ACGAACCCCC | CGTTCAGCCC | GACCGCTGCG | 2160
| CCTTATCCGG | TAACTATCGT | CTTGAGTCCA | ACCCGGTAAG | ACACGACTTA | TCGCCACTGG | 2220
| CAGCAGCCAC | TGGTAACAGG | ATTAGCAGAG | CGAGGTATGT | AGGCGGTGCT | ACAGAGTTCT | 2280
| TGAAGTGGTG | GCCTAACTAC | GGCTACACTA | GAAGGACAGT | ATTTGGTATC | TGCGCTCTGC | 2340
| TGAAGCCAGT | TACCTTCGGA | AAAAGAGTTG | GTAGCTCTTG | ATCCGGCAAA | CAAACCACCG | 2400
| CTGGTAGCGG | TGGTTTTTTT | GTTTGCAAGC | AGCAGATTAC | GCGCAGAAAA | AAAGGATCTC | 2460
| AAGAAGATCC | TTTGATCTTT | TCTACGGGGT | CTGACGCTCA | GTGGAACGAA | AACTCACGTT | 2520
| AAGGGATTTT | GGTCATGAGA | TTATCAAAAA | GGATCTTCAC | CTAGATCCTT | TTAAATTAAA | 2580
| AATGAAGTTT | TAAATCAATC | TAAAGTATAT | ATGAGTAAAC | TTGGTCTGAC | AGTTACCAAT | 2640
| GCTTAATCAG | TGAGGCACCT | ATCTCAGCGA | TCTGTCTATT | TCGTTCATCC | ATAGTTGCCT | 2700
| GACTCCCCGT | CGTGTAGATA | ACTACGATAC | GGGAGGGCTT | ACCATCTGGC | CCCAGTGCTG | 2760
| CAATGATACC | GCGAGACCCA | CGCTCACCGG | CTCCAGATTT | ATCAGCAATA | AACCAGCCAG | 2820
| CCGGAAGGGC | CGAGCGCAGA | AGTGGTCCTG | CAACTTTATC | CGCCTCCATC | CAGTCTATTA | 2880
| ATTGTTGCCG | GGAAGCTAGA | GTAAGTAGTT | CGCCAGTTAA | TAGTTTGCGC | AACGTTGTTG | 2940
| CCATTGCTGC | AGGCATCGTG | GTGTCACGCT | CGTCGTTTGG | TATGGCTTCA | TTCAGCTCCG | 3000
| GTTCCCAACG | ATCAAGGCGA | GTTACATGAT | CCCCCATGTT | GTGCAAAAAA | GCGGTTAGCT | 3060
| CCTTCGGTCC | TCCGATCGTT | GTCAGAAGTA | AGTTGGCCGC | AGTGTTATCA | CTCATGGTTA | 3120
| TGGCAGCACT | GCATAATTCT | CTTACTGTCA | TGCCATCCGT | AAGATGCTTT | TCTGTGACTG | 3180
| GTGAGTACTC | AACCAAGTCA | TTCTGAGAAT | AGTGTATGCG | GCGACCGAGT | TGCTCTTGCC | 3240
| CGGCGTCAAC | ACGGGATAAT | ACCGCGCCAC | ATAGCAGAAC | TTTAAAAGTG | CTCATCATTG | 3300
| GAAAACGTTC | TTCGGGGCGA | AAACTCTCAA | GGATCTTACC | GCTGTTGAGA | TCCAGTTCGA | 3360
| TGTAACCCAC | TCGTGCACCC | AACTGATCTT | CAGCATCTTT | TACTTTCACC | AGCGTTTCTG | 3420
| GGTGAGCAAA | AACAGGAAGG | CAAAATGCCG | CAAAAAAGGG | AATAAGGGCG | ACACGGAAAT | 3480
| GTTGAATACT | CATACTCTTC | CTTTTTCAAT | ATTATTGAAG | CATTTATCAG | GGTTATTGTC | 3540
| TCATGAGCGG | ATACATATTT | GAATGTATTT | AGAAAAATAA | ACAAATAGGG | GTTCCGCGCA | 3600
| CATTTCCCCG | AAAAGTGCCA | CCTGACGTCT | AAGAAACCAT | TATTATCATG | ACATTAACCT | 3660
| ATAAAAATAG | GCGTATCACG | AGGCCCTTTC | GTCTTCAAG | | | 3699

(2) INFORMATION FOR SEQ ID NO:121:

(i) SEQUENCE CHARACTERISTICS:
(A) LENGTH: 87 base pairs
(B) TYPE: nucleic acid (C) STRANDEDNESS: single
(D) TOPOLOGY: linear (ii) MOLECULE TYPE: DNA (genomic)

(xi) SEQUENCE DESCRIPTION: SEQ ID NO:121:

TACTGTGCGA GACGGCTAAC TGGGGTTGAT GCTTTTGATA TCTGGGGCCA AGGGACAATG 60

GTCACCGTCT CTTCAGCCTC CACCAAG 87

(2) INFORMATION FOR SEQ ID NO:122:

(i) SEQUENCE CHARACTERISTICS:
(A) LENGTH: 87 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:122:

TACTGTGCGA GACACCGTAT AGCAGCAGCT GGCTTTGACT ACTGGGGCCA GGGAACCCTG 60

GTCACCGTCT CCTCAGCCTC CACCAAG 87

(2) INFORMATION FOR SEQ ID NO:123:

(i) SEQUENCE CHARACTERISTICS:
(A) LENGTH: 86 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:123:

TACTGTGCGA GAATTACTAC TACTACTACG GTATGGACGT CTGGGGCCAA GGGACCACGG 60

TCACCGTCTC CTCAGCCTCC ACCAAG 86

(2) INFORMATION FOR SEQ ID NO:124:

(i) SEQUENCE CHARACTERISTICS:
(A) LENGTH: 102 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:124:

TACTGTGCGA GAATTACGAT ATTTTGACTG GTCTACTACT ACTACGGTAT GGACGTCTGG 60

GGCCAAGGGA CCACGGTCAC CGTCTCCTCA GCCTCCACCA AG 102

(2) INFORMATION FOR SEQ ID NO:125:

(i) SEQUENCE CHARACTERISTICS:
(A) LENGTH: 84 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:125:

TACTATGGTT CGGGGAGTTA TTATAACGTC TTTGACTACT GGGGCCAGGG AACCCTGGTC 60

ACCGTCTCCT CAGCCTCCAC CAAG 84

( 2 ) INFORMATION FOR SEQ ID NO:126:

( i ) SEQUENCE CHARACTERISTICS:
        ( A ) LENGTH: 85 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:126:

```
TACTATGGTT CGCGGGGGGT GTCTGATGCT TTTGATATCT GGGGCCAAGG GACAATGGTC    60

ACCGTCTCTT CAGGCCTCCA CCAAG                                          85
```

( 2 ) INFORMATION FOR SEQ ID NO:127:

( i ) SEQUENCE CHARACTERISTICS:
        ( A ) LENGTH: 79 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:127:

```
TACTATGGTT CGGCAACTGG CGCTTTTGAT ATCTGGGGCC AAGGGACAAT GGTCACCGTC    60

TCTTCAGGGG AGTGCATCC                                                 79
```

( 2 ) INFORMATION FOR SEQ ID NO:128:

( i ) SEQUENCE CHARACTERISTICS:
        ( A ) LENGTH: 95 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:128:

```
TACTATGGTT CGTCGGCTAA CTGGGGATCC TACTACTACT ACGGACGTCT GGGGCCAAGG    60

GACCACGGTC ACCGTCTCCT CAGCGGAGTG CATCC                               95
```

( 2 ) INFORMATION FOR SEQ ID NO:129:

( i ) SEQUENCE CHARACTERISTICS:
        ( A ) LENGTH: 69 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:129:

```
TACTATGGTT CGTACTTCCA GCACTGGGGC CAGGGCACCC TGGTCACCGT CTCCTCAGGG    60

AGTGCATCC                                                            69
```

( 2 ) INFORMATION FOR SEQ ID NO:130:

( i ) SEQUENCE CHARACTERISTICS:
        ( A ) LENGTH: 81 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:130:

-continued

```
TACTATGGTT CGCACGTAGC TAACTCTTTT GACTACTGGG GCCAGGGAAC CCTGGTCACC    60

GTCTCCTCAG GGAGTGCATC C                                              81
```

( 2 ) INFORMATION FOR SEQ ID NO:131:

( i ) SEQUENCE CHARACTERISTICS:
        ( A ) LENGTH: 90 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:131:

```
TACTGTGCGA GAATTACTAT GGTTCGGGGA GTTCCCTTTG ACTACTGGGG CCAGGGAACC    60

CTGGTCACCG TCTCCTCAGG GAGTGCATCC                                     90
```

( 2 ) INFORMATION FOR SEQ ID NO:132:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:132:

```
TACTGTGCGA GCAAATACTT CCAGCACTGG GGCCAGGGCA CCCTGGTCAC CGTCTCCTCA    60

GGGAGTGCAT CC                                                        72
```

( 2 ) INFORMATION FOR SEQ ID NO:133:

( i ) SEQUENCE CHARACTERISTICS:
        ( A ) LENGTH: 93 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:133:

```
TACTGTGCGA GACAAACTGG GGACTACTAC TACTACGGTA TGGACGTCTG GGGCCAAGGG    60

ACCACGGTCA CCGTCTCCTC AGGGAGTGCA TCC                                 93
```

( 2 ) INFORMATION FOR SEQ ID NO:134:

( i ) SEQUENCE CHARACTERISTICS:
        ( A ) LENGTH: 108 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:134:

```
TACTGTGCGA GACATTACTA TGGTTCGGGG AGTTATGACT ACTACTACTA CGGTATGGAC    60

GTCTGGGGCC AAGGGACCAC GGTCACCGTC TCCTCAGGGA GTGCATCC                108
```

( 2 ) INFORMATION FOR SEQ ID NO:135:

( i ) SEQUENCE CHARACTERISTICS:
        ( A ) LENGTH: 64 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:135:

| TACTGTGCGA | GACAGGGAGT | GGGGCCAGGG | AACCCTGGTC | ACCGTCTCCT | CAGCCTCCAC | 60 |
| CAAG | | | | | | 64 |

( 2 ) INFORMATION FOR SEQ ID NO:136:

( i ) SEQUENCE CHARACTERISTICS:
    ( A ) LENGTH: 80 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:136:

| TACTGTGTGA | GATTCTGGGA | GACTGGTTCG | ACCCCTGGGG | CCAGGGAACC | CTGGTCACCG | 60 |
| TCTCCTCAGG | GAGTGCATCC | | | | | 80 |

( 2 ) INFORMATION FOR SEQ ID NO:137:

( i ) SEQUENCE CHARACTERISTICS:
    ( A ) LENGTH: 102 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:137:

| TACTGTGCGA | GACGGAGGTA | CTATGGTTCG | GGGAGTTATT | ATAACGTCTT | TGACTACTGG | 60 |
| GGCCAGGGAA | CCCTGGTCAC | CGTCTCCTCA | GCCTCCACCA | AG | | 102 |

( 2 ) INFORMATION FOR SEQ ID NO:138:

( i ) SEQUENCE CHARACTERISTICS:
    ( A ) LENGTH: 78 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:138:

| TACTGTGCGA | GACAAACCTG | GGGAGGAGAC | TACTGGGGCC | AGGGAACCCT | GGTCACCGTC | 60 |
| TCCTCAGCCT | CCACCAAG | | | | | 78 |

( 2 ) INFORMATION FOR SEQ ID NO:139:

( i ) SEQUENCE CHARACTERISTICS:
    ( A ) LENGTH: 99 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:139:

| TACTGTGCGA | GAGGATATAG | TGGCTACGAT | AACTACTACT | ACGGTATGGA | CGTCTGGGGC | 60 |
| CAAGGGACCA | CGGTCACCGT | CTCCTCAGCC | TCCACCAAG | | | 99 |

( 2 ) INFORMATION FOR SEQ ID NO:140:

( i ) SEQUENCE CHARACTERISTICS:
    ( A ) LENGTH: 84 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:140:

```
TACTGTGCGA GACAAACTGG GGAGGACTAC TTTGACTACT GGGGCCAGGG AACCCTGGTC        60
ACCGTCTCCT CAGGGAGTGC ATCC                                               84
```

( 2 ) INFORMATION FOR SEQ ID NO:141:

( i ) SEQUENCE CHARACTERISTICS:
    ( A ) LENGTH: 94 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:141:

```
TACTGTGCGA GATATAGTGG CTACGATTAC CTACTGGTAC TTCGATCTCT GGGGCCGTGG        60
CACCCTGGTC ACTGTCTCCT CAGCCTCCAC CGAG                                    94
```

( 2 ) INFORMATION FOR SEQ ID NO:142:

( i ) SEQUENCE CHARACTERISTICS:
    ( A ) LENGTH: 96 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:142:

```
TACTGTGCGA GAGCATCCCT CCCCTCCTTT GACTACTACG GTATGGACGT CTGGGGCCAA        60
GGGACCACGG TCACCGTCTC CTCAGCCTCC ACCAAG                                  96
```

( 2 ) INFORMATION FOR SEQ ID NO:143:

( i ) SEQUENCE CHARACTERISTICS:
    ( A ) LENGTH: 77 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:143:

```
TACTGTGCGA GACGGGGTGG GGGTTTGACT ACTGGGGCCA GGGAACCCTG GTCACCGTCT        60
CCTCAGGGAG TGCATCC                                                       77
```

( 2 ) INFORMATION FOR SEQ ID NO:144:

( i ) SEQUENCE CHARACTERISTICS:
    ( A ) LENGTH: 94 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:144:

```
TACTGTGTGC CGGTCGAAAC TTTACTACTA CTACTACGGT ATGGACGTCT GGGGCCAAGG        60
```

```
GACCACGGTC  ACCGTCTCCT  CAGGGAGTGC  ATCC                                              9 4
```

( 2 ) INFORMATION FOR SEQ ID NO:145:

( i ) SEQUENCE CHARACTERISTICS:
    ( A ) LENGTH: 84 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:145:

```
TACTGTGTGA  GAGATATTTT  GACTGGTTAA  CGTGACTACT  GGGGCCAGGG  AACCCTGGTC    60

ACCGTCTCCT  CAGGGAGTGC  ATCC                                              84
```

( 2 ) INFORMATION FOR SEQ ID NO:146:

( i ) SEQUENCE CHARACTERISTICS:
    ( A ) LENGTH: 93 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:146:

```
TACTGTGCGA  GACATGGTAT  AGCAGCAGCT  GGTACTGCTT  TTGATATCTG  GGGCCAAGGG    60

ACAATGGTCA  CCGTCTCTTC  AGGGAGTGCA  TCC                                   93
```

( 2 ) INFORMATION FOR SEQ ID NO:147:

( i ) SEQUENCE CHARACTERISTICS:
    ( A ) LENGTH: 84 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:147:

```
TACTGTGTGA  GATCAACTGG  GGTTGATGCT  TTTGATATCT  GGGGCCAAGG  GACAATGGTC    60

ACCGTCTCTT  CAGGGAGTGC  ATCC                                              84
```

( 2 ) INFORMATION FOR SEQ ID NO:148:

( i ) SEQUENCE CHARACTERISTICS:
    ( A ) LENGTH: 85 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:148:

```
TACTGTGCGG  AAATAGCAGC  AGCTGCCCTA  CTTTGACTAC  TGGGGCCAGG  GAACCCTGGT    60

CACCGTCTCC  TCAGGGAGTG  CATCC                                             85
```

( 2 ) INFORMATION FOR SEQ ID NO:149:

( i ) SEQUENCE CHARACTERISTICS:
    ( A ) LENGTH: 87 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:149:

TACTGTGTGT GTATAGCAGC AGCTGGTAAA GGAAACGGCT ACTGGGGCCA GGGAACCCTG    60

GTCACCGTCT CCTCAGGGAG TGCATCC    87

( 2 ) INFORMATION FOR SEQ ID NO:150:

( i ) SEQUENCE CHARACTERISTICS:
       ( A ) LENGTH: 75 base pairs
       ( B ) TYPE: nucleic acid
       ( C ) STRANDEDNESS: single
       ( D ) TOPOLOGY: linear ( i i ) MOLECULE TYPE: DNA (genomic)

( x i ) SEQUENCE DESCRIPTION: SEQ ID NO:150:

TACTGTGCGA GACAAAACTG GGGTGACTAC TGGGGCCAGG GAACCCTGGT CACCGTCTCC    60

TCAGGGAGTG CATCC    75

TRANSGENIC NON-HUMAN ANIMALS FOR PRODUCING HETEROLOGOUS ANTIBODIES

CROSS-REFERENCE TO RELATED APPLICATION

This application is a continuation in part of U.S. Ser. No. 07/834,539, filed Feb. 5, 1992, now U.S. Pat. No. 5,633,425, which is continuation-in-part of U.S. Ser. No. 07/810,279 filed Dec. 17, 1991 now U.S. Pat. No. 5,569,825 which is a continuation-in-part of U.S. Ser. No 07/575,962 filed Aug. 31, 1990 now abandoned, which is a continuation-in-part of U.S. Ser. No. 07/574,748 filed Jul. 9, 1990 now abandoned. This application claims foreign priority benefits under Title 35, United States Code, Section 119, to PCT Application No. PCT/US91/06185 which corresponds to U.S. Ser. No. 07/834,539 filed Feb. 5, 1992.

TECHNICAL FIELD

The invention relates to transgenic non-human animals capable of producing heterologous antibodies, transgenes used to produce such transgenic animals, transgenes capable of functionally rearranging a heterologous D gene, immortalized B-cells capable of producing heterologous antibodies, methods and transgenes for producing heterologous antibodies of multiple isotypes, methods and transgenes for inactivating or suppressing expression of endogenous immunoglobulin loci.

BACKGROUND OF THE INVENTION

One of the major impediments facing the development of in vivo therapeutic and diagnostic applications for monoclonal antibodies in humans is the intrinsic immunogenicity of non-human immunoglobulins. For example, when immunocompetent human patients are administered therapeutic doses of rodent monoclonal antibodies, the patients produce antibodies against the rodent immunoglobulin sequences; these human anti-mouse antibodies (HAMA) neutralize the therapeutic antibodies and can cause acute toxicity. Hence, it is desirable to produce human immunoglobulins that are reactive with specific human antigens that are promising therapeutic and/or diagnostic targets. However, producing human immunoglobulins that bind specifically with human antigens is problematic.

The present technology for generating monoclonal antibodies involves pre-exposing, or priming, an animal (usually a rat or mouse) with antigen, harvesting B-cells from that animal, and generating a library of hybridoma clones. By screening a hybridoma population for antigen binding specificity (idiotype) and also screening for immunoglobulin class (isotype), it is possible to select hybridoma clones that secrete the desired antibody.

However, when present methods for generating monoclonal antibodies are applied for the purpose of generating human antibodies that have binding specificities for human antigens, obtaining B-lymphocytes which produce human immunoglobulins a serious obstacle, since humans will typically not make immune responses against self-antigens.

Hence, present methods of generating human monoclonal antibodies that are specifically reactive with human antigens are clearly insufficient. It is evident that the same limitations on generating monoclonal antibodies to authentic self antigens apply where non-human species are used as the source of B-cells for making the hybridoma.

The construction of transgenic animals harboring a functional heterologous immunoglobulin transgene are a method by which antibodies reactive with self antigens may be produced. However, in order to obtain expression of therapeutically useful antibodies, or hybridoma clones producing such antibodies, the transgenic animal must produce transgenic B cells that are capable of maturing through the B lymphocyte development pathway. Such maturation requires the presence of surface IgM on the transgenic B cells, however isotypes other than IgM are desired for therapeutic uses. Thus, there is a need for transgenes and animals harboring such transgenes that are able to undergo functional V-D-J rearrangement to generate recombinational diversity and junctional diversity. Further, such transgenes and transgenic animals preferably include cis-acting sequences that facilitate isotype switching from a first isotype that is required for B cell maturation to a subsequent isotype that has superior therapeutic utility.

A number of experiments have reported the use of transfected cell lines to determine the specific DNA sequences required for Ig gene rearrangement (reviewed by Lewis and Gellert (1989), *Cell*, 59, 585–588). Such reports have identified putative sequences and concluded that the accessibility of these sequences to the recombinase enzymes used for rearrangement is modulated by transcription (Yancopoulos and Alt (1985), *Cell*, 40, 271–281). The sequences for V(D)J joining are reportedly a highly conserved, near-palindromic heptamer and a less well conserved AT-rich nanomer separated by a spacer of either 12 or 23 bp (Tonegawa (1983), *Nature*, 302, 575–581; Hesse, et al. (1989), *Genes in Dev.*, 3, 1053–1061). Efficient recombination reportedly occurs only between sites containing recombination signal sequences with different length spacer regions.

Ig gene rearrangement, though studied in tissue culture cells, has not been extensively examined in transgenic mice. Only a handful of reports have been published describing rearrangement test constructs introduced into mice [Buchini, et al. (1987), *Nature*, 326, 409–411 (unrearranged chicken λ transgene); Goodhart, et al. (1987), *Proc. Natl. Acad. Sci. USA*, 84, 4229–4233) (unrearranged rabbit κ gene); and Bruggemann, et al. (1989), *Proc. Natl. Acad. Sci. USA*, 86, 6709–6713 (hybrid mouse-human heavy chain)]. The results of such experiments, however, have been variable, in some cases, producing incomplete or minimal rearrangement of the transgene.

Further, a variety of biological functions of antibody molecules are exerted by the Fc portion of molecules, such as the interaction with mast cells or basophils through Fcε, and binding of complement by Fcμ or Fcγ, it further is desirable to generate a functional diversity of antibodies of a given specificity by variation of isotype.

Although transgenic animals have been generated that incorporate transgenes encoding one or more chains of a heterologous antibody, there have been no reports of heterologous transgenes that undergo successful isotype switching. Transgenic animals that cannot switch isotypes are limited to producing heterologous antibodies of a single isotype, and more specifically are limited to producing an isotype that is essential for B cell maturation, such as IgM and possibly IgD, which may be of limited therapeutic utility. Thus, there is a need for heterologous immunoglobulin transgenes and transgenic animals that are capable of switching from an isotype needed for B cell development to an isotype that has a desired characteristic for therapeutic use.

Based on the foregoing, it is clear that a need exists for methods of efficiently producing heterologous antibodies, e.g. antibodies encoded by genetic sequences of a first species that are produced in a second species. More particularly, there is a need in the art for heterologous immunoglobulin transgenes and transgenic animals that are capable of undergoing functional V-D-J gene rearrangement that incorporates all or a portion of a D gene segment which contributes to recombinational diversity. Further, there is a need in the art for transgenes and transgenic animals that can support V-D-J recombination and isotype switching so that (1) functional B cell development may occur, and (2) therapeutically useful heterologous antibodies may be produced. There is also a need for a source of B cells which can be used to make hybridomas that produce monoclonal antibodies for therapeutic or diagnostic use in the particular species for which they are designed. A heterologous immunoglobulin transgene capable of functional V-D-J recombination and/or capable of isotype switching could fulfill these needs.

In accordance with the foregoing object transgenic nonhuman animals are provided which are capable of producing a heterologous antibody, such as a human antibody.

Further, it is an object to provide B-cells from such transgenic animals which are capable of expressing heterologous antibodies wherein such B-cells are immortalized to provide a source of a monoclonal antibody specific for a particular antigen.

In accordance with this foregoing object, it is a further object of the invention to provide hybridoma cells that are capable of producing such heterologous monoclonal antibodies.

Still further, it is an object herein to provide heterologous unrearranged and rearranged immunoglobulin heavy and light chain transgenes useful for producing the aforementioned non-human transgenic animals.

Still further, it is an object herein to provide methods to disrupt endogenous immunoglobulin loci in the transgenic animals.

Still further, it is an object herein to provide methods to induce heterologous antibody production in the aforementioned transgenic non-human animal.

A further object of the invention is to provide methods to generate an immunoglobulin variable region gene segment repertoire that is used to construct one or more transgenes of the invention.

The references discussed herein are provided solely for their disclosure prior to the filing date of the present application. Nothing herein is to be construed as an admission that the inventors are not entitled to antedate such disclosure by virtue of prior invention.

SUMMARY OF THE INVENTION

Transgenic nonhuman animals are provided which are capable of producing a heterologous antibody, such as a human antibody. Such heterologous antibodies may be of various isotypes, including: IgG1, IgG2, IgG3, IgG4, IgM, IgA1, IgA2, IgA$_{sec}$, IgD, of IgE. In order for such transgenic nonhuman animals to make an immune response, it is necessary for the transgenic B cells and pre-B cells to produce surface-bound immunoglobulin, particularly of the IgM (or possibly IgD) isotype, in order to effectuate B cell development and antigen-stimulated maturation. Such expression of an IgM (or IgD) surface-bound immunoglobulin is only required during the antigen-stimulated maturation phase of B cell development, and mature B cells may produce other isotypes, although only a single switched isotype may be produced at a time.

Typically, a cell of the B-cell lineage will produce only a single isotype at a time, although cis or trans alternative RNA splicing, such as occurs naturally with the $\mu_S$ (secreted $\mu$) and $\mu_M$ (membrane-bound $\mu$) forms, and the $\mu$ and $\delta$ immunoglobulin chains, may lead to the contemporaneous expression of multiple isotypes by a single cell. Therefore, in order to produce heterologous antibodies of multiple isotypes, specifically the therapeutically useful IgG, IgA, and IgE isotypes, it is necessary that isotype switching occur. Such isotype switching may be classical class-switching or may result from one or more non-classical isotype switching mechanisms.

The invention provides heterologous immunoglobulin transgenes and transgenic nonhuman animals harboring such transgenes, wherein the transgenic animal is capable of producing heterologous antibodies of multiple isotypes by undergoing isotype switching. Classical isotype switching occurs by recombination events which involve at least one switch sequence region in the transgene. Non-classical isotype switching may occur by, for example, homologous recombination between human $\sigma_\mu$ and human $\Sigma_\mu$ sequences ($\delta$-associated deletion). Alternative non-classical switching mechanisms, such as intertransgene and/or interchromosomal recombination, among others, may occur and effectuate isotype switching. Such transgenes and transgenic nonhuman animals produce a first immunoglobulin isotype that is necessary for antigen-stimulated B cell maturation and can switch to encode and produce one or more subsequent heterologous isotypes that have therapeutic and/or diagnostic utility. Transgenic nonhuman animals of the invention are thus able to produce, in one embodiment, IgG, IgA, and/or IgE antibodies that are encoded by human immunoglobulin genetic sequences and which also bind specific human antigens with high affinity.

The invention also encompasses B-cells from such transgenic animals that are capable of expressing heterologous antibodies of various isotypes, wherein such B-cells are immortalized to provide a source of a monoclonal antibody specific for a particular antigen. Hybridoma cells that are derived from such B-cells can serve as one source of such heterologous monoclonal antibodies.

The invention provides heterologous unrearranged and rearranged immunoglobulin heavy and light chain transgenes capable of undergoing isotype switching in vivo in the aforementioned non-human transgenic animals or in explanted lymphocytes of the B-cell lineage from such transgenic animals. Such isotype switching may occur spontaneously or be induced by treatment of the transgenic animal or explanted B-lineage lymphocytes with agents that promote isotype switching, such as T-cell-derived lymphokines (e.g., IL-4 and IFN$_\gamma$)

Still further, the invention includes methods to induce heterologous antibody production in the aforementioned transgenic non-human animal, wherein such antibodies may be of various isotypes. These methods include producing an antigen-stimulated immune response in a transgenic nonhuman animal for the generation of heterologous antibodies, particularly heterologous antibodies of a switched isotype (i.e., IgG, IgA, and IgE).

This invention provides methods whereby the transgene contains sequences that effectuate isotype switching, so that the heterologous immunoglobulins produced in the transgenic animal and monoclonal antibody clones derived from the B-cells of said animal may be of various isotypes.

This invention further provides methods that facilitate isotype switching of the transgene, so that switching between particular isotypes may occur at much higher or lower frequencies or in different temporal orders than typically occurs in germline immunoglobulin loci. Switch regions may be grafted from various $C_H$ genes and ligated to other $C_H$ genes in a transgene construct; such grafted switch sequences will typically function independently of the associated $C_H$ gene so that switching in the transgene construct will typically be a function of the origin of the associated switch regions. Alternatively, or in combination with switch sequences, δ-associated deletion sequences may be linked to various $C_H$ genes to effect non-classical switching by deletion of sequences between two δ-associated deletion sequences. Thus, a transgene may be constructed so that a particular $C_H$ gene is linked to a different switch sequence and thereby is switched to more frequently than occurs when the naturally associated switch region is used.

This invention also provides methods to determine whether isotype switching of transgene sequences has occurred in a transgenic animal containing an immunoglobulin transgene.

The invention provides immunoglobulin transgene constructs and methods for producing immunoglobulin transgene constructs, some of which contain a subset of germline immunoglobulin loci sequences (which may include deletions). The invention includes a specific method for facilitated cloning and construction of immunoglobulin transgenes, involving a vector that employs unique XhoI and SalI restriction sites flanked by two unique NotI sites. This method exploits the complementary termini of XhoI and SalI restrictions sites and is useful for creating large constructs by ordered concatemerization of restriction fragments in a vector.

The transgenes of the invention include a heavy chain transgene comprising DNA encoding at least one variable gene segment, one diversity gene segment, one joining gene segment and one constant region gene segment. The immunoglobulin light chain transgene comprises DNA encoding at least one variable gene segment, one joining gene segment and one constant region gene segment. The gene segments encoding the light and heavy chain gene segments are heterologous to the transgenic non-human animal in that they are derived from, or correspond to, DNA encoding immunoglobulin heavy and light chain gene segments from a species not consisting of the transgenic non-human animal. In one aspect of the invention, the transgene is constructed such that the individual gene segments are unrearranged, i.e., not rearranged so as to encode a functional immunoglobulin light or heavy chain. Such unrearranged transgenes permit recombination of the gene segments (functional rearrangement) and expression of the resultant rearranged immunoglobulin heavy and/or light chains within the transgenic non-human animal when said animal is exposed to antigen.

In one aspect of the invention, heterologous heavy and light immunoglobulin transgenes comprise relatively large fragments of unrearranged heterologous DNA. Such fragments typically comprise a substantial portion of the C, J (and in the case of heavy chain, D) segments from a heterologous immunoglobulin locus. In addition, such fragments also comprise a substantial portion of the variable gene segments.

In one embodiment, such transgene constructs comprise regulatory sequences, e.g. promoters, enhancers, class switch regions, recombination signals and the like, corresponding to sequences derived from the heterologous DNA. Alternatively, such regulatory sequences may be incorporated into the transgene from the same or a related species of the non-human animal used in the invention. For example, human immunoglobulin gene segments may be combined in a transgene with a rodent immunoglobulin enhancer sequence for use in a transgenic mouse.

In a method of the invention, a transgenic non-human animal containing germline unrearranged light and heavy immunoglobulin transgenes—that undergo VDJ joining during B-cell differentiation—is contacted with an antigen to induce production of a heterologous antibody in a secondary repertoire B-cell.

Also included in the invention are vectors and methods to disrupt the endogenous immunoglobulin loci in the non-human animal to be used in the invention. Such vectors and methods utilize a transgene, preferably positive-negative selection vector, which is constructed such that it targets the functional disruption of a class of gene segments encoding a heavy and/or light immunoglobulin chain endogenous to the non-human animal used in the invention. Such endogenous gene segments include diversity, joining and constant region gene segments. In this aspect of the invention, the positive-negative selection vector is contacted with at least one embryonic stem cell of a non-human animal after which cells are selected wherein the positive-negative selection vector has integrated into the genome of the non-human animal by way of homologous recombination. After transplantation, the resultant transgenic non-human animal is substantially incapable of mounting an immunoglobulin-mediated immune response as a result of homologous integration of the vector into chromosomal DNA. Such immune deficient non-human animals may thereafter be used for study of immune deficiencies or used as the recipient of heterologous immunoglobulin heavy and light chain transgenes.

The invention also provides vectors, methods, and compositions useful for suppressing the expression of one or more species of immunoglobulin chain(s), without disrupting an endogenous immunoglobulin locus. Such methods are useful for suppressing expression of one or more endogenous immunoglobulin chains while permitting the expression of one or more transgene-encoded immunoglobulin chains. Unlike genetic disruption of an endogenous immunoglobulin chain locus, suppression of immunoglobulin chain expression does not require the time-consuming breeding that is needed to establish transgenic animals homozygous for a disrupted endogenous Ig locus. An additional advantage of suppression as compared to engognous Ig gene disruption is that, in certain embodiments, chain suppression is reversible within an individual animal. For example, Ig chain suppression may be accomplished with: (1) transgenes encoding and expressing antisense RNA that specifically hybridizes to an endogenous Ig chain gene sequence, (2) antisense oligonucleotides that specifically hybridize to an endogenous Ig chain gene sequence, and (3) immunoglobulins that bind specifically to an endogenous Ig chain polypeptide.

The references discussed herein are provided solely for their disclosure prior to the filing date of the present application. Nothing herein is to be construed as an admission that the inventors are not entitled to antedate such disclosure by virtue of prior invention.

BRIEF DESCRIPTION OF THE FIGURES

FIGS. 21a through f depict the structure of a mouse heavy chain targeting vector.

Figure 1:
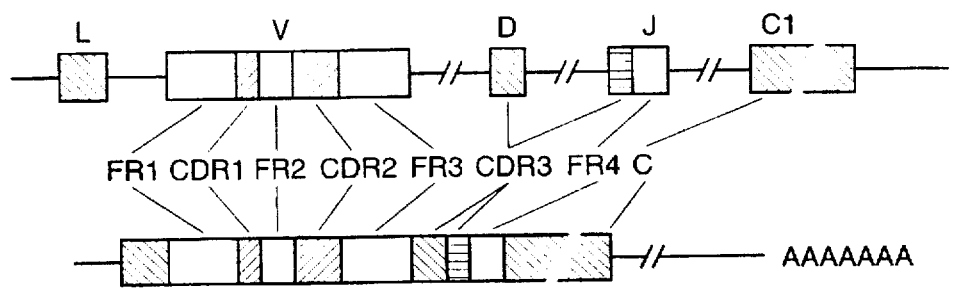
FIG. 1 depicts the complementarity determining regions CDR1, CDR2 and CDR3 and framework regions FR1, FR2, FR3 and FR4 in unrearranged genomic DNA and mRNA expressed from a rearranged immunoglobulin heavy chain gene.
Figure 2:
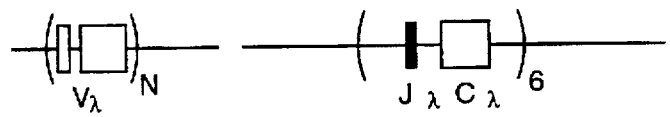
FIG. 2 depicts the human λ chain locus.
Figure 3:
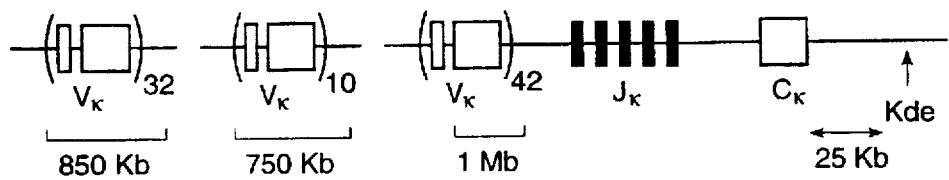
FIG. 3 depicts the human κ chain locus.

Table 1 depicts the sequence of vector pGPe.

Table 2 depicts the sequence of gene V$_H$49.8.

Table 3 depicts the detection of human IgM and IgG in the serum of transgenic mice of this invention.

Table 4 depicts sequences of VDJ joints.

Table 5 depicts the distribution of J segments incorporated into pHC1 transgene encoded transcripts to J segments found in adult human peripheral blood lymphocytes (PBL).

Table 6 depicts the distribution of D segments incorporated into pHC1 transgene encoded transcripts to D segments found in adult human peripheral blood lymphocytes (PBL).

Table 7 depicts the length of the CDR3 peptides from transcripts with in-frame VDJ joints in the pHC1 transgenic mouse and in human PBL.

Table 8 depicts the predicted amino acid sequences of the VDJ regions from 30 clones analyzed from a pHC1 transgenic.

DETAILED DESCRIPTION

As has been discussed supra, it is desirable to produce human immunoglobulins that are reactive with specific human antigens that are promising therapeutic and/or diagnostic targets. However, producing human immunoglobulins that bind specifically with human antigens is problematic.

First, the immunized animal that serves as the source of B cells must make an immune response against the presented antigen. In order for an animal to make an immune response, the antigen presented must be foreign and the animal must not be tolerant to the antigen. Thus, for example, if it is desired to produce a human monoclonal antibody with an idiotype that binds to a human protein, self-tolerance will prevent an immunized human from making a substantial immune response to the human protein, since the only epitopes of the antigen that may be immunogenic will be those that result from polymorphism of the protein within the human population (allogeneic epitopes).

Second, if the animal that serves as the source of B-cells for forming a hybridoma (a human in the illustrative given example) does make an immune response against an authentic self antigen, a severe autoimmune disease may result in the animal. Where humans would be used as a source of B-cells for a hybridoma, such autoimmunization would be considered unethical by contemporary standards.

One methodology that can be used to obtain human antibodies that are specifically reactive with human antigens is the production of a transgenic mouse harboring the human immunoglobulin transgene constructs of this invention. Briefly, transgenes containing all or portions of the human immunoglobulin heavy and light chain loci, or transgenes containing synthetic "miniloci" (described infra, and in copending applications U.S. Ser. No. 07/574,748 filed Aug. 29, 1990, U.S. Ser. No. 07/575,962 filed Aug. 31, 1990, and PCT/US91/06185 filed Aug. 28, 1991) which comprise essential functional elements of the human heavy and light chain loci, are employed to produce a transgenic nonhuman animal. Such a transgenic nonhuman animal will have the capacity to produce immunoglobulin chains that are encoded by human immunoglobulin genes, and additionally will be capable of making an immune response against human antigens. Thus, such transgenic animals can serve as a source of immune sera reactive with specified human antigens, and B-cells from such transgenic animals can be fused with myeloma cells to produce hybridomas that secrete monoclonal antibodies that are encoded by human immunoglobulin genes and which are specifically reactive with human antigens.

The production of transgenic mice containing various forms of immunoglobulin genes has been reported previously. Rearranged mouse immunoglobulin heavy or light chain genes have been used to produce transgenic mice. In addition, functionally rearranged human Ig genes including the µ or γ1 constant region have been expressed in transgenic mice. However, experiments in which the transgene comprises unrearranged (V-D-J or V-J not rearranged) immunoglobulin genes have been variable, in some cases, producing incomplete or minimal rearrangement of the transgene. However, there are no published examples of either rearranged or unrearranged immunoglobulin transgenes which undergo successful isotype switching between $C_H$ genes within a transgene.

Definitions

As used herein, the term "antibody" refers to a glycoprotein comprising at least two light polypeptide chains and two heavy polypeptide chains. Each of the heavy and light polypeptide chains contains a variable region (generally the amino terminal portion of the polypeptide chain) which contains a binding domain which interacts with antigen. Each of the heavy and light polypeptide chains also comprises a constant region of the polypeptide chains (generally the carboxyl terminal portion) which may mediate the binding of the immunoglobulin to host tissues or factors including various cells of the immune system, some phagocytic cells and the first component (Clq) of the classical complement system.

As used herein, a "heterologous antibody" is defined in relation to the transgenic non-human organism producing such an antibody. It is defined as an antibody having an amino acid sequence or an encoding DNA sequence corresponding to that found in an organism not consisting of the transgenic non-human animal.

As used herein, a "heterohybrid antibody" refers to an antibody having a light and heavy chains of different organismal origins. For example, an antibody having a human heavy chain associated with a murine light chain is a heterohybrid antibody.

As used herein, "isotype" refers to the antibody class (e.g., IgM or IgG$_1$) that is encoded by heavy chain constant region genes.

As used herein, "isotype switching" refers to the phenomenon by which the class, or isotype, of an antibody changes from one Ig class to one of the other Ig classes.

As used herein, "nonswitched isotype" refers to the isotypic class of heavy chain that is produced when no isotype switching has taken place; the $C_H$ gene encoding the nonswitched isotype is typically the first $C_H$ gene immediately downstream from the functionally rearranged VDJ gene.

As used herein, the term "switch sequence" refers to those DNA sequences responsible for switch recombination. A "switch donor" sequence, typically a µ switch region, will be 5' (i.e., upstream) of the construct region to be deleted during the switch recombination. The "switch acceptor" region will be between the construct region to be deleted and the replacement constant region (e.g., γ, ε, etc.). As there is no specific site where recombination always occurs, the final gene sequence will typically not be predictable from the construct.

As used herein, "glycosylation pattern" is defined as the pattern of carbohydrate units that are covalently attached to a protein, more specifically to an immunoglobulin protein. A glycosylation pattern of a heterologous antibody can be characterized as being substantially similar to glycosylation patterns which occur naturally on antibodies produced by the species of the nonhuman transgenic animal, when one of ordinary skill in the art would recognize the glycosylation pattern of the heterologous antibody as being more similar to said pattern of glycosylation in the species of the non-human transgenic animal than to the species from which the $C_H$ genes of the transgene were derived.

Transgenic Nonhuman Animals Capable of Producing Heterologous Antibodies

The design of a transgenic non-human animal that responds to foreign antigen stimulation with a heterologous antibody repertoire, requires that the heterologous immunoglobulin transgenes contained within the transgenic animal function correctly throughout the pathway of B-cell development. In a preferred embodiment, correct function of a heterologous heavy chain transgene includes isotype switching. Accordingly, the transgenes of the invention are constructed so as to produce isotype switching and one or more of the following: (1) high level and cell-type specific expression, (2) functional gene rearrangement, (3) activation of and response to allelic exclusion, (4) expression of a sufficient primary repertoire, (5) signal transduction, (6) somatic hypermutation, and (7) domination of the transgene antibody locus during the immune response.

As will be apparent from the following disclosure, not all of the foregoing criteria need be met. For example, in those embodiments wherein the endogenous immunoglobulin loci of the transgenic animal are functionally disrupted, the transgene need not activate allelic exclusion. Further, in those embodiments wherein the transgene comprises a functionally rearranged heavy and/or light chain immunoglobulin gene, the second criteria of functional gene rearrangement is unnecessary, at least for that transgene which is already rearranged. For background on molecular immunology, see, *Fundamental Immunology*, 2nd edition (1989), Paul William E., ed. Raven Press, N.Y., which is incorporated herein by reference.

In one aspect of the invention, transgenic non-human animals are provided that contain rearranged, unrearranged or a combination of rearranged and unrearranged heterologous immunoglobulin heavy and light chain transgenes in the germline of the transgenic animal. Each of the heavy chain transgenes comprises at least one $C_H$ gene. In addition, the heavy chain transgene may contain functional isotype switch sequences, which are capable of supporting isotype switching of a heterologous transgene encoding multiple $C_H$ genes in B-cells of the transgenic animal. Such switch sequences may be those which occur naturally in the germline immunoglobulin locus from the species that serves as the source of the transgene $C_H$ genes, or such switch sequences may be derived from those which occur in the species that is to receive the transgene construct (the transgeneic animal). For example, a human transgene construct that is used to produce a transgenic mouse may produce a higher frequency of isotype switching events if it incorporates switch sequences similar to those that occur naturally in the mouse heavy chain locus, as presumably the mouse switch sequences are optimized to function with the mouse switch recombinase enzyme system, whereas the human switch sequences are not. Switch sequences made be isolated and cloned by conventional cloning methods, or may be synthesized de novo from overlapping synthetic oligonucleotides designed on the basis of published sequence information relating to immunoglobulin switch region sequences (Mills et al., *Nucl. Acids Res.* 18: 7305–7316 (1991); Sideras et al., *Intl. Immunol.* 1: 631–642 (1989), which are incorporated herein by reference).

For each of the foregoing transgenic animals, functionally rearranged heterologous heavy and light chain immunoglobulin transgenes are found in a significant fraction of the B-cells of the transgenic animal (at least 10 percent).

The transgenes of the invention include a heavy chain transgene comprising DNA encoding at least one variable gene segment, one diversity gene segment, one joining gene segment and at least one constant region gene segment. The immunoglobulin light chain transgene comprises DNA encoding at least one variable gene segment, one joining gene segment and at least one constant region gene segment. The gene segments encoding the light and heavy chain gene segments are heterologous to the transgenic non-human animal in that they are derived from, or correspond to, DNA encoding immunoglobulin heavy and light chain gene segments from a species not consisting of the transgenic non-human animal. In one aspect of the invention, the transgene is constructed such that the individual gene segments are unrearranged, i.e., not rearranged so as to encode a functional immunoglobulin light or heavy chain. Such unrearranged transgenes support recombination of the V, D, and J gene segments (functional rearrangement) and preferably support incorporation of all or a portion of a D region gene segment in the resultant rearranged immunoglobulin heavy chain within the transgenic non-human animal when exposed to antigen.

In an alternate embodiment, the transgenes comprise an unrearranged "mini-locus". Such transgenes typically comprise a substantial portion of the C, D, and J segments as well as a subset of the V gene segments. In such transgene constructs, the various regulatory sequences, e.g. promoters, enhancers, class switch regions, splice-donor and splice-acceptor sequences for RNA processing, recombination signals and the like, comprise corresponding sequences derived from the heterologous DNA. Such regulatory sequences may be incorporated into the transgene from the same or a related species of the non-human animal used in the invention. For example, human immunoglobulin gene segments may be combined in a transgene with a rodent immunoglobulin enhancer sequence for use in a transgenic mouse. Alternatively, synthetic regulatory sequences may be incorporated into the transgene, wherein such synthetic regulatory sequences are not homologous to a functional DNA sequence that is known to occur naturally in the genomes of mammals. Synthetic regulatory sequences are designed according to consensus rules, such as, for example, those specifying the permissible sequences of a splice-acceptor site or a promoter/enhancer motif.

The invention also includes transgenic animals containing germ line cells having a heavy and light transgene wherein one of the said transgenes contains rearranged gene segments with the other containing unrearranged gene segments. In the preferred embodiments, the rearranged transgene is a light chain immunoglobulin transgene and the unrearranged transgene is a heavy chain immunoglobulin transgene.

The Structure and Generation of Antibodies

The basic structure of all immunoglobulins is based upon a unit consisting of two light polypeptide chains and two heavy polypeptide chains. Each light chain comprises two regions known as the variable light chain region and the constant light chain region. Similarly, the immunoglobulin heavy chain comprises two regions designated the variable heavy chain region and the constant heavy chain region.

The constant region for the heavy or light chain is encoded by genomic sequences referred to as heavy or light constant region gene ($C_H$) segments. The use of a particular heavy chain gene segment defines the class of immunoglobulin. For example, in humans, the μ constant region gene segments define the IgM class of antibody whereas the use of a γ, γ2, γ3 or γ4 constant region gene segment defines the IgG class of antibodies as well as the IgG subclasses IgG1 through IgG4. Similarly, the use of a $α_1$ or α2 constant region gene segment defines the IgA class of antibodies as well as the subclasses IgA1 and IgA2. The δ and ε constant region gene segments define the IgD and IgE antibody classes, respectively.

The variable regions of the heavy and light immunoglobulin chains together contain the antigen binding domain of the antibody. Because of the need for diversity in this region of the antibody to permit binding to a wide range of antigens, the DNA encoding the initial or primary repertoire variable region comprises a number of different DNA segments derived from families of specific variable region gene segments. In the case of the light chain variable region, such families comprise variable (V) gene segments and joining (J) gene segments. Thus, the initial variable region of the light chain is encoded by one V gene segment and one J gene segment each selected from the family of V and J gene segments contained in the genomic DNA of the organism. In the case of the heavy chain variable region, the DNA encoding the initial or primary repertoire variable region of the heavy chain comprises one heavy chain V gene segment, one heavy chain diversity (D) gene segment and one J gene segment, each selected from the appropriate V, D and J families of immunoglobulin gene segments in genomic DNA.

In order to increase the diversity of sequences that contribute to forming antibody binding sites, it is preferable that a heavy chain transgene include cis-acting sequences that support functional V-D-J rearrangement that can incorporate all or part of a D region gene sequence in a rearranged V-D-J gene sequence. Typically, at least about 1 percent of expressed transgene-encoded heavy chains (or mRNAs) include recognizable D region sequences in the V region. Preferably, at least about 10 percent of transgene-encoded V regions include recognizable D region sequences, more preferably at least about 30 percent, and most preferably more than 50 percent include recognizable D region sequences.

A recognizable D region sequence is generally at least about eight consecutive nucleotides corresponding to a sequence present in a D region gene segment of a heavy chain transgene and/or the amino acid sequence encoded by such D region nucleotide sequence. For example, if a transgene includes the D region gene DHQ52, a transgene-encoded mRNA containing the sequence 5'-TAACTGGG-3' located in the V region between a V gene segment sequence and a J gene segment sequence is recognizable as containing a D region sequence, specifically a DHQ52 sequence. Similarly, for example, if a transgene includes the D region gene DHQ52, a transgene-encoded heavy chain polypeptide containing the amino acid sequence —DAF— located in the V region between a V gene segment amino acid sequence and a J gene segment amino acid sequence is recognizable as containing a D region sequence, specifically a DHQ52 sequence.

However, because of somatic mutation and N-region addition, some D region sequences may be recognizable but may not correspond identically to a consecutive D region sequence in the transgene. For example, a nucleotide sequence 5'CTAAXTGGGG-3'(SEQ ID NO:1), where X is A, T, or G, and which is located in a heavy chain V region and flanked by a V region gene sequence and a J region gene sequence, can be recognized as corresponding to the DHQ52 sequence 5'-CTAACTGGG-3'. Similarly, for example, the polypeptide sequences —DAFDI— (SEQ ID NO:2), —DYFDY—(SEQ ID NO:3), or —GAFDI— (SEQ ID NO:4) located in a V region and flanked on the amino-terminal side by an amino acid sequence encoded by a transgene V gene sequence and flanked on the carboxyter-minal side by an amino acid sequence encoded by a transgene J gene sequence is recognizable as a D region sequence.

Therefore, because somatic mutation and N-region addition can produce mutations in sequences derived from a transgene D region, the following definition is provided as a guide for determining the presence of a recognizable D region sequence. An amino acid sequence or nucleotide sequence is recognizable as a D region sequence if: (1) the sequence is located in a V region and is flanked on one side by a V gene sequence (nucleotide sequence or deduced amino acid sequence) and on the other side by a J gene sequence (nucleotide sequence or deduced amino acid sequence) and (2) the sequence is substantially identical or substantially similar to a known D gene sequence (nucleotide sequence or encoded amino acid sequence).

The term "substantial identity" as used herein denotes a characteristic of a polypeptide sequence or nucleic acid sequence, wherein the polypeptide sequence has at least 50 percent sequence identity compared to a reference sequence, and the nucleic acid sequence has at least 70 percent sequence identity compared to a reference sequence. The percentage of sequence identity is calculated excluding small deletions or additions which total less than 35 percent of the reference sequence. The reference sequence may be a subset of a larger sequence, such as an entire D gene; however, the reference sequence is at least 8 nucleotides long in the case of polynucleotides, and at least 3 amino residues long in the case of a polypeptide. Typically, the reference sequence is at least 8 to 12 nucleotides or at least 3 to 4 amino acids, and preferably the reference sequence is 12 to 15 nucleotides or more, or at least 5 amino acids.

The term "substantial similarity" denotes a characteristic of an polypeptide sequence, wherein the polypeptide sequence has at least 80 percent similarity to a reference sequence. The percentage of sequence similarity is calculated by scoring identical amino acids or positional conservative amino acid substitutions as similar. A positional conservative amino acid substitution is one that can result from a single nucleotide substitution; a first amino acid is replaced by a second amino acid where a codon for the first amino acid and a codon for the second amino acid can differ by a single nucleotide substitution. Thus, for example, the sequence -Lys-Glu-Arg-Val- (SEG ID NO:5) is substantially similar to the sequence -Asn-Asp-Ser-Val- (SEG ID NO:6), since the codon sequence -AAA-GAA-AGA-GUU- (SEG ID NO:7) can be mutated to -AAC-GAC-AGC-GUU- (SEG ID NO:8) by introducing only 3 substitution mutations, single nucleotide substitutions in three of the four original codons.

The reference sequence may be a subset of a larger sequence, such as an entire D gene; however, the reference sequence is at least 4 amino residues long. Typically, the reference sequence is at least 5 amino acids, and preferably the reference sequence is 6 amino acids or more.

The Primary Repertoire

The process for generating DNA encoding the heavy and light chain immunoglobulin genes occurs primarily in developing B-cells. Prior to the joining of various immunoglobulin gene segments, the V, D, J and constant (C) gene segments are found, for the most part, in clusters of V, D, J and C gene segments in the precursors of primary repertoire B-cells. Generally, all of the gene segments for a heavy or light chain are located in relatively close proximity on a single chromosome. Such genomic DNA prior to recombination of the various immunoglobulin gene segments is referred to herein as "unrearranged" genomic DNA. During B-cell differentiation, one of each of the appropriate family members of the V, D, J (or only V and J in the case of light chain genes) gene segments are recombined to form functionally rearranged heavy and light immunoglobulin genes. Such functional rearrangement is of the variable region segments to form DNA encoding a functional variable region. This gene segment rearrangement process appears to be sequential. First, heavy chain D-to-J joints are made, followed by heavy chain V-to-DJ joints and light chain V-to-J joints. The DNA encoding this initial form of a functional variable region in a light and/or heavy chain is referred to as "functionally rearranged DNA" or "rearranged DNA". In the case of the heavy chain, such DNA is referred to as "rearranged heavy chain DNA" and in the case of the light chain, such DNA is referred to as "rearranged light chain DNA". Similar language is used to describe the functional rearrangement of the transgenes of the invention.

The recombination of variable region gene segments to form functional heavy and light chain variable regions is mediated by recombination signal sequences (RSS's) that flank recombinationally competent V, D and J segments. RSS's necessary and sufficient to direct recombination, comprise a dyad-symmetric heptamer, an AT-rich nonamer and an intervening spacer region of either 12 or 23 base pairs. These signals are conserved among the different loci and species that carry out D-J (or V-J) recombination and are functionally interchangeable. See Oettinger, et al. (1990), *Science*, 248, 1517–1523 and references cited therein. The heptamer comprises the sequence CACAGTG or its analogue followed by a spacer of unconserved sequence and then a nonamer having the sequence ACAAAAACC or its analogue. These sequences are found on the J, or downstream side, of each V and D gene segment. Immediately preceding the germline D and J segments are again two recombination signal sequences, first the nonamer and then the heptamer again separated by an unconserved sequence. The heptameric and nonameric sequences following a $V_L$, $V_H$ or D segment are complementary to those preceding the $J_L$, D or $J_H$ segments with which they recombine. The spacers between the heptameric and nonameric sequences are either 12 base pairs long or between 22 and 24 base pairs long.

In addition to the rearrangement of V, D and J segments, further diversity is generated in the primary repertoire of immunoglobulin heavy and light chain by way of variable recombination between the V and J segments in the light chain and between the D and J segments of the heavy chain. Such variable recombination is generated by variation in the exact place at which such segments are joined. Such variation in the light chain typically occurs within the last codon of the V gene segment and the first codon of the J segment. Similar imprecision in joining occurs on the heavy chain chromosome between the D and $J_H$ segments and may extend over as many as 10 nucleotides. Furthermore, several nucleotides may be inserted between the D and $J_H$ and between the $V_H$ and D gene segments which are not encoded by genomic DNA. The addition of these nucleotides is known as N-region diversity.

After VJ and/or VDJ rearrangement, transcription of the rearranged variable region and one or more constant region gene segments located downstream from the rearranged variable region produces a primary RNA transcript which upon appropriate RNA splicing results in an mRNA which encodes a full length heavy or light immunoglobulin chain. Such heavy and light chains include a leader signal sequence to effect secretion through and/or insertion of the immunoglobulin into the transmembrane region of the B-cell. The DNA encoding this signal sequence is contained within the first exon of the V segment used to form the variable region of the heavy or light immunoglobulin chain. Appropriate regulatory sequences are also present in the mRNA to control translation of the mRNA to produce the encoded heavy and light immunoglobulin polypeptides which upon proper association with each other form an antibody molecule.

The net effect of such rearrangements in the variable region gene segments and the variable recombination which may occur during such joining, is the production of a primary antibody repertoire. Generally, each B-cell which has differentiated to this stage, produces a single primary repertoire antibody. During this differentiation process, cellular events occur which suppress the functional rearrangement of gene segments other than those contained within the functionally rearranged Ig gene. The process by which diploid B-cells maintain such mono-specificity is termed allelic exclusion.

The Secondary Repertoire

B-cell clones expressing immunoglobulins from within the set of sequences comprising the primary repertoire are immediately available to respond to foreign antigens. Because of the limited diversity generated by simple VJ and VDJ joining, the antibodies produced by the so-called primary response are of relatively low affinity. Two different types of B-cells make up this initial response: precursors of primary antibody-forming cells and precursors of secondary repertoire B-cells (Linton et al., *Cell* 59: 1049–1059 (1989)). The first type of B-cell matures into IgM-secreting plasma cells in response to certain antigens. The other B-cells respond to initial exposure to antigen by entering a T-cell dependent maturation pathway.

During the T-cell dependent maturation of antigen stimulated B-cell clones, the structure of the antibody molecule on the cell surface changes in two ways: the constant region switches to a non-IgM subtype and the sequence of the variable region can be modified by multiple single amino acid substitutions to produce a higher affinity antibody molecule.

As previously indicated, each variable region of a heavy or light Ig chain contains an antigen binding domain. It has been determined by amino acid and nucleic acid sequencing that somatic mutation during the secondary response occurs throughout the V region including the three complementary determining regions (CDR1, CDR2 and CDR3) also referred to as hypervariable regions 1, 2 and 3. The CDR1 and CDR2 are located within the variable gene segment whereas the CDR3 is largely the result of recombination between V and J gene segments or V, D and J gene segments. Those portions of the variable region which do not consist of CDR1, 2 or 3 are commonly referred to as framework regions designated FR1, FR2, FR3 and FR4. See FIG. 1. During hypermutation, the rearranged DNA is mutated to give rise to new clones with altered Ig molecules. Those clones with higher affinities for the foreign antigen are selectively expanded by helper T-cells, giving rise to affinity maturation of the expressed antibody. Clonal selection typically results in expression of clones containing new mutation within the CDR1, 2 and/or 3 regions. However, mutations outside these regions also occur which influence the specificity and affinity of the antigen binding domain.

Transgenic Non-Human Animals Capable of Producing Heterologous Antibody

Transgenic non-human animals in one aspect of the invention are produced by introducing at least one of the immunoglobulin transgenes of the invention (discussed hereinafter) into a zygote or early embryo of a non-human animal. The non-human animals which are used in the invention generally comprise any mammal which is capable of rearranging immunoglobulin gene segments to produce a primary antibody response. Such nonhuman transgenic animals may include, for example, transgenic pigs, transgenic rabbits, transgenic cattle, and other transgenic animal species, particularly mammalian species. A particularly preferred non-human animal is the mouse or other members of the rodent family.

However, the invention is not limited to the use of mice. Rather, any non-human mammal which is capable of mounting a primary and secondary antibody response may be used. Such animals include non-human primates, such as chimpanzee, bovine, ovine and porcine species, other members of the rodent family, e.g. rat, as well as rabbit and guinea pig. Particular preferred animals are mouse, rat, rabbit and guinea pig, most preferably mouse.

In one embodiment of the invention, various gene segments from the human genome are used in heavy and light chain transgenes in an unrearranged form. In this embodiment, such transgenes are introduced into mice. The unrearranged gene segments of the light and/or heavy chain transgene have DNA sequences unique to the human species which are distinguishable from the endogenous immunoglobulin gene segments in the mouse genome. They may be readily detected in unrearranged form in the germ line and somatic cells not consisting of B-cells and in rearranged form in B-cells.

In an alternate embodiment of the invention, the transgenes comprise rearranged heavy and/or light immunoglobulin transgenes. Specific segments of such transgenes corresponding to functionally rearranged VDJ or VJ segments, contain immunoglobulin DNA sequences which are also clearly distinguishable from the endogenous immunoglobulin gene segments in the mouse.

Such differences in DNA sequence are also reflected in the amino acid sequence encoded by such human immunoglobulin transgenes as compared to those encoded by mouse B-cells. Thus, human immunoglobulin amino acid sequences may be detected in the transgenic non-human animals of the invention with antibodies specific for immunoglobulin epitopes encoded by human immunoglobulin gene segments.

Transgenic B-cells containing unrearranged transgenes from human or other species functionally recombine the appropriate gene segments to form functionally rearranged light and heavy chain variable regions. It will be readily apparent that the antibody encoded by such rearranged transgenes has a DNA and/or amino acid sequence which is heterologous to that normally encountered in the nonhuman animal used to practice the invention.

Unrearranged Transgenes

As used herein, an "unrearranged immunoglobulin heavy chain transgene" comprises DNA encoding at least one variable gene segment, one diversity gene segment, one joining gene segment and one constant region gene segment. Each of the gene segments of said heavy chain transgene are derived from, or has a sequence corresponding to, DNA encoding immunoglobulin heavy chain gene segments from a species not consisting of the non-human animal into which said transgene is introduced. Similarly, as used herein, an "unrearranged immunoglobulin light chain transgene" comprises DNA encoding at least one variable gene segment, one joining gene segment and at least one constant region gene segment wherein each gene segment of said light chain transgene is derived from, or has a sequence corresponding to, DNA encoding immunoglobulin light chain gene segments from a species not consisting of the non-human animal into which said light chain transgene is introduced.

Such heavy and light chain transgenes in this aspect of the invention contain the above-identified gene segments in an unrearranged form. Thus, interposed between the V, D and J segments in the heavy chain transgene and between the V and J segments on the light chain transgene are appropriate recombination signal sequences (RSS's). In addition, such transgenes also include appropriate RNA splicing signals to join a constant region gene segment with the VJ or VDJ rearranged variable region.

In order to facilitate isotype switching within a heavy chain transgene containing more than one C region gene segment, e.g. Cµ and Cγ1 from the human genome, as explained below "switch regions" are incorporated upstream from each of the constant region gene segments and downstream from the variable region gene segments to permit recombination between such constant regions to allow for immunoglobulin class switching, e.g. from IgM to IgG. Such heavy and light immunoglobulin transgenes also contain transcription control sequences including promoter regions situated upstream from the variable region gene segments which typically contain TATA motifs. A promoter region can be defined approximately as a DNA sequence that, when operably linked to a downstream sequence, can produce transcription of the downstream sequence. Promoters may require the presence of additional linked cis-acting sequences in order to produce efficient transcription. In addition, other sequences that participate in the transcription of sterile transcripts are preferably included. Examples of sequences that participate in expression of sterile transcripts can be found in the published literature, including Rothman et al., Intl. Immunol. 2: 621–627 (1990); Reid et al., Proc. Natl. Acad. Sci. USA 86: 840–844 (1989); Stavnezer et al., Proc. Natl. Acad. Sci. USA 85: 7704–7708 (1988); and Mills et al., Nucl. Acids Res. 18: 305–7316 (1991), each of which is incorporated herein by reference. These sequences typically include about at least 50 bp immediately upstream of a switch region, preferably about at least 200 bp upstream of a switch region; and more preferably about at least 200–1000 bp or more upstream of a switch region. Suitable sequences occur immediately upstream of the human $S_{\gamma 1}$, $S_{\gamma 2}$, $S_{\gamma 3}$, $S_{\gamma 4}$, $S_{\alpha 1}$, $S_{\alpha 2}$ and $S_\epsilon$ switch regions, although the sequences immediately upstream of the human $S_{\gamma 1}$, and $S_{\gamma 3}$ switch regions are preferable. In particular, interferon (IFN) inducible transcriptional regulatory elements, such as IFN-inducible enhancers, are preferably included immediately upstream of transgene switch sequences.

In addition to promoters, other regulatory sequences which function primarily in B-lineage cells are used. Thus, for example, a light chain enhancer sequence situated preferably between the J and constant region gene segments on the light chain transgene is used to enhance transgene expression, thereby facilitating allelic exclusion. In the case of the heavy chain transgene, regulatory enhancers and also employed. Such regulatory sequences are used to maximize the transcription and translation of the transgene so as to induce allelic exclusion and to provide relatively high levels of transgene expression.

Although the foregoing promoter and enhancer regulatory control sequences have been generically described, such regulatory sequences may be heterologous to the nonhuman animal being derived from the genomic DNA from which the heterologous transgene immunoglobulin gene segments are obtained. Alternately, such regulatory gene segments are derived from the corresponding regulatory sequences in the genome of the non-human animal, or closely related species, which contains the heavy and light transgene.

In the preferred embodiments, gene segments are derived from human beings. The transgenic non-human animals harboring such heavy and light transgenes are capable of mounting an Ig-mediated immune response to a specific antigen administered to such an animal. B-cells are produced within such an animal which are capable of producing heterologous human antibody. After immortalization, and the selection for an appropriate monoclonal antibody (Mab), e.g. a hybridoma, a source of therapeutic human monoclonal antibody is provided. Such human Mabs have significantly reduced immunogenicity when therapeutically administered to humans.

Although the preferred embodiments disclose the construction of heavy and light transgenes containing human gene segments, the invention is not so limited. In this regard, it is to be understood that the teachings described herein may be readily adapted to utilize immunoglobulin gene segments from a species other than human beings. For example, in addition to the therapeutic treatment of humans with the antibodies of the invention, therapeutic antibodies encoded by appropriate gene segments may be utilized to generate monoclonal antibodies for use in the veterinary sciences.

Rearranged Transgenes

In an alternative embodiment, transgenic nonhuman animals contain functionally at least one rearranged heterologous heavy chain immunoglobulin transgene in the germline of the transgenic animal. Such animals contain primary repertoire B-cells that express such rearranged heavy transgenes. Such B-cells preferably are capable of undergoing somatic mutation when contacted with an antigen to form a heterologous antibody having high affinity and specificity for the antigen. Said rearranged transgenes will contain at least two $C_H$ genes and the associated sequences required for isotype switching.

The invention also includes transgenic animals containing germ line cells having heavy and light transgenes wherein one of the said transgenes contains rearranged gene segments with the other containing unrearranged gene segments. In such animals, the heavy chain transgenes shall have at least two $C_H$ genes and the associated sequences required for isotype switching.

The invention further includes methods for generating a synthetic variable region gene segment repertoire to be used in the transgenes of the invention. The method comprises generating a population of immunoglobulin V segment DNAs wherein each of the V segment DNAs encodes an immunoglobulin V segment and contains at each end a cleavage recognition site of a restriction endonuclease. The population of immunoglobulin V segment DNAs is thereafter concatenated to form the synthetic immunoglobulin V segment repertoire. Such synthetic variable region heavy chain transgenes shall have at least two $C_H$ genes and the associated sequences required for isotype switching.

Isotype Switching

In the development of a B lymphocyte, the cell initially produces IgM with a binding specificity determined by the productively rearranged $V_H$ and $V_L$ regions. Subsequently, each B cell and its progeny cells synthesize antibodies with the same L and H chain V regions, but they may switch the isotype of the H chain.

The use of μ or δ constant regions is largely determined by alternate splicing, permitting IgM and IgD to be coexpressed in a single cell. The other heavy chain isotypes (γ, α, and ε) are only expressed natively after a gene rearrangement event deletes the Cμ and Cδ exons. This gene rearrangement process, termed isotype switching, typically occurs by recombination between so called switch segments located immediately upstream of each heavy chain gene (except δ). The individual switch segments are between 2 and 10 kb in length, and consist primarily of short repeated sequences. The exact point of recombination differs for individual class switching events. Investigations which have used solution hybridization kinetics or Southern blotting with cDNA-derived $C_H$ probes have confirmed that switching can be associated with loss of $C_H$ sequences from the cell.

The switch (S) region of the μ gene, $S_\mu$, is located about 1 to 2 kb 5' to the coding sequence and is composed of numerous tandem repeats of sequences of the form $(GAGCT)_n(GGGGT)$, where n is usually 2 to 5 but can range as high as 17. (See T. Nikaido et al. *Nature* 292: 845–848 (1981))

Similar internally repetitive switch sequences spanning several kilobases have been found 5' of the other $C_H$ genes. The Sα region has been sequenced and found to consist of tandemly repeated 80-bp homology units, whereas $S_{\gamma2a}$, $S_{\gamma2b}$, and $S_{\gamma3}$ all contain repeated 49-bp homology units very similar to each other. (See P. Szurek et al., *J. Immunol* 135: 620–626 (1985) and T. Nikaido et al., *J. Biol. Chem.* 257: 7322–7329 (1982), which are incorporated herein by reference.) All the sequenced S regions include numerous occurrences of the pentamers GAGCT and GGGGT that are the basic repeated elements of the $S_\mu$ gene (T. Nikaido et al., *J. Biol. Chem.* 257: 7322–7329 (1982) which is incorporated herein by reference); in the other S regions these pentamers are not precisely tandemly repeated as in $S_\mu$, but instead are embedded in larger repeat units. The $S_{\gamma1}$ region has an additional higher-order structure: two direct repeat sequences flank each of two clusters of 49-bp tandem repeats. (See M. R. Mowatt et al., *J. Immunol.* 136: 2674–2683 (1986), which is incorporated herein by reference).

Switch regions of human H chain genes have been found to be very similar to their mouse homologs. Indeed, similarity between pairs of human and mouse clones 5' to the $C_H$ genes has been found to be confined to the S regions, a fact that confirms the biological significance of these regions.

A switch recombination between μ and α genes produces a composite $S_\mu$–$S_\alpha$ sequence. Typically, there is no specific site, either in $S_\mu$ or in any other S region, where the recombination always occurs.

Generally, unlike the enzymatic machinery of V-J recombination, the switch machinery can apparently accommodate different alignments of the repeated homologous regions of germline S precursors and then join the sequences at different positions within the alignment. (See, T. H. Rabbits et al., *Nucleic Acids Res.* 9: 4509–4524 (1981) and J. Ravetch et al., *Proc. Natl. Acad. Sci. USA* 77: 6734–6738 (1980), which are incorporated herein by reference.)

The exact details of the mechanism(s) of selective activation of switching to a particular isotype are unknown. Although exogenous influences such as lymphokines and cytokines might upregulate isotype-specific recombinases, it is also possible that the same enzymatic machinery catalyzes switches to all isotypes and that specificity lies in targeting this machinery to specific switch regions.

The T-cell-derived lymphokines IL-4 and $IFN_\gamma$ have been shown to specifically promote the expression of certain isotypes: IL-4 decreases IgM, IgG2a, IgG2b, and IgG3 expression and increases IgE and IgG1 expression; while $IFN_\gamma$ selectively stimulates IgG2a expression and antagonizes the IL-4-induced increase in IgE and IgG1 expression (Coffman et al., *J. Immunol.* 136: 949–954 (1986) and Snapper et al., *Science* 236: 944–947 (1987), which are incorporated herein by reference). A combination of IL-4 and IL-5 promotes IgA expression (Coffman et al., *J. Immunol.* 139: 3685–3690 (1987), which is incorporated herein by reference).

Most of the experiments implicating T-cell effects on switching have not ruled out the possibility that the observed increase in cells with particular switch recombinations might reflect selection of preswitched or precommitted cells; but the most likely explanation is that the lymphokines actually promote switch recombination.

Induction of class switching appears to be associated with sterile transcripts that initiate upstream of the switch segments (Lutzker et al., *Mol. Cell. Biol.* 8: 1849 (1988); Stavnezer et al., *Proc. Natl. Acad. Sci. USA* 85: 7704 (1988); Esser and Radbruch, *EMBO J.* 8: 483 (1989); Berton et al., *Proc. Natl. Acad. Sci. USA* 86: 2829 (1989); Rothman et al., *Int. Immunol.* 2: 621 (1990), each of which is incorporated by reference). For example, the observed induction of the γ1 sterile transcript by IL-4 and inhibition by IFN-γ correlates with the observation that IL-4 promotes class switching to γ1 in B-cells in culture, while IFN-γ inhibits γ1 expression. Therefore, the inclusion of regulatory sequences that affect the transcription of sterile transcripts may also affect the rate of isotype switching. For example, increasing the transcription of a particular sterile transcript typically can be expected to enhance the frequency of isotype switch recombination involving adjacent switch sequences.

For these reasons, it is preferable that transgenes incorporate transcriptional regulatory sequences within about 1–2 kb upstream of each switch region that is to be utilized for isotype switching. These transcriptional regulatory sequences preferably include a promoter and an enhancer element, and more preferably include the 5' flanking (i.e., upstream) region that is naturally associated (i.e., occurs in germline configuration) with a switch region. This 5' flanking region is typically about at least 50 nucleotides in length, preferably about at least 200 nucleotides in length, and more preferably at least 500–1000 nucleotides.

Although a 5' flanking sequence from one switch region can be operably linked to a different switch region for transgene construction (e.g., the 51 flanking sequence from the human $S_{\gamma1}$ switch can be grafted immediately upstream of the $S_{\alpha1}$ switch), in some embodiments it is preferred that each switch region incorporated in the transgene construct have the 5' flanking region that occurs immediately upstream in the naturally occurring germline configuration.

The Transgenic Primary Repertoire

A. The Human Immunoglobulin Loci

An important requirement for transgene function is the generation of a primary antibody repertoire that is diverse enough to trigger a secondary immune response for a wide range of antigens. The rearranged heavy chain gene consists of a signal peptide exon, a variable region exon and a tandem array of multi-domain constant region regions, each of which is encoded by several exons. Each of the constant region genes encode the constant portion of a different class of immunoglobulins. During B-cell development. V region proximal constant regions are deleted leading to the expression of new heavy chain classes. For each heavy chain class, alternative patterns of RNA splicing give rise to both transmembrane and secreted immunoglobulins.

The human heavy chain locus consists of approximately 200 V gene segments spanning 2 Mb, approximately 30 D gene segments spanning about 40 kb, six J segments clustered within a 3 kb span, and nine constant region gene segments spread out over approximately 300 kb. The entire locus spans approximately 2.5 Mb of the distal portion of the long arm of chromosome 14.

B. Gene Fragment Transgenes

1. Heavy Chain Transgene

In a preferred embodiment, immunoglobulin heavy and light chain transgenes comprise unrearranged genomic DNA from humans. In the case of the heavy chain, a preferred transgene comprises a NotI fragment having a length between 670 to 830 kb. The length of this fragment is ambiguous because the 3' restriction site has not been accurately mapped. It is known, however, to reside between the α1 and Ωα gene segments. This fragment contains members of all six of the known $V_H$ families, the D and J gene segments, as well as the μ, δ, γ3, γ1 and α1 constant regions (Berman et al., *EMBO J.* 7: 727–738 (1988), which is incorporated herein by reference). A transgenic mouse line containing this transgene correctly expresses a heavy chain class required for B-cell development (IgM) and at least one switched heavy chain class ($IgG_1$), in conjunction with a sufficiently large repertoire of variable regions to trigger a secondary response for most antigens.

2. Light Chain Transgene

A genomic fragment containing all of the necessary gene segments and regulatory sequences from a human light chain locus may be similarly constructed. Such transgenes are constructed as described in the Examples and in copending application, entitled "Transgenic Non-Human Animals Capable of Producing Heterologous Antibodies," filed Aug. 29, 1990, under U.S. Ser. No. 07/574,748.

C. Transgenes Generated Intracellularly by In Vivo Recombination

It is not necessary to isolate the all or part of the heavy chain locus on a single DNA fragment. Thus, for example, the 670–830 kb NotI fragment from the human immunoglobulin heavy chain locus may be formed in vivo in the non-human animal during transgenesis. Such in vivo transgene construction is produced by introducing two or more overlapping DNA fragments into an embryonic nucleus of the non-human animal. The overlapping portions of the DNA fragments have DNA sequences which are substantially homologous. Upon exposure to the recombinases contained within the embryonic nucleus, the overlapping DNA fragments homologously recombined in proper orientation to form the 670–830 kb NotI heavy chain fragment.

In vivo transgene construction can be used to form any number of immunoglobulin transgenes which because of their size are otherwise difficult, or impossible, to make or manipulate by present technology. Thus, in vivo transgene construction is useful to generate immunoglobulin transgenes which are larger than DNA fragments which may be manipulated by YAC vectors (Murray and Szostak, *Nature* 305: 189–193 (1983)). Such in vivo transgene construction may be used to introduce into a non-human animal substantially the entire immunoglobulin loci from a species not consisting of the transgenic non-human animal.

In addition to forming genomic immunoglobulin transgenes, in vivo homologous recombination may also be utilized to form "mini-locus" transgenes as described in the Examples.

In the preferred embodiments utilizing in vivo transgene construction, each overlapping DNA fragment preferably has an overlapping substantially homologous DNA sequence between the end portion of one DNA fragment and the end portion of a second DNA fragment. Such overlapping portions of the DNA fragments preferably comprise about 500 bp to about 2000 bp, most preferably 1.0 kb to 2.0 kb. Homologous recombination of overlapping DNA fragments to form transgenes in vivo is further described in commonly assigned U.S. patent application entitled "Intracellular Generation of DNA by Homologous Recombination of DNA Fragments" filed Aug. 29, 1990, under U.S. Ser. No. 07/574,747.

D. Minilocus Transgenes

As used herein, the term "immunoglobulin minilocus" refers to a DNA sequence (which may be within a longer sequence), usually of less than about 150 kb, typically between about 25 and 100 kb, containing at least one each of the following: a functional variable (V) gene segment, a functional joining (J) region segment, at least one functional constant (C) region gene segment, and—if it is a heavy chain minilocus—a functional diversity (D) region segment, such that said DNA sequence contains at least one substantial discontinuity (e.g., a deletion, usually of at least about 2 to 5 kb, preferably 10–25 kb or more, relative to the homologous genomic DNA sequence). A light chain minilocus transgene will be at least 25 kb in length, typically 50 to 60 kb. A heavy chain transgene will typically be about 70 to 80 kb in length, preferably at least about 60 kb with two constant regions operably linked to switch regions. Furthermore, the individual elements of the minilocus are preferably in the germline configuration and capable of undergoing gene rearrangement in the pre-B cell of a transgenic animal so as to express functional antibody molecules with diverse antigen specificities encoded entirely by the elements of the minilocus. Further, a heavy chain minilocus comprising at least two $C_H$ genes and the requisite switching sequences is typically capable of undergoing isotype switching, so that functional antibody molecules of different immunoglobulin classes will be generated. Such isotype switching may occur in vivo in B-cells residing within the transgenic nonhuman animal, or may occur in cultured cells of the B-cell lineage which have been explanted from the transgenic nonhuman animal.

In an alternate preferred embodiment, immunoglobulin heavy chain transgenes comprise one or more of each of the $V_H$, D, and $J_H$ gene segments and two or more of the $C_H$ genes. At least one of each appropriate type gene segment is incorporated into the minilocus transgene. With regard to the $C_H$ segments for the heavy chain transgene, it is preferred that the transgene contain at least one μ gene segment and at least one other constant region gene segment, more preferably a γ gene segment, and most preferably γ3 or γ1. This preference is to allow for class switching between IgM and IgG forms of the encoded immunoglobulin and the production of a secretable form of high affinity non-IgM immunoglobulin. Other constant region gene segments may also be used such as those which encode for the production of IgD, IgA and IgE.

Those skilled in the art will also construct transgenes wherein the order of occurrence of heavy chain $C_H$ genes will be different from the naturally-occurring spatial order found in the germline of the species serving as the donor of the $C_H$ genes.

Additionally, those skilled in the art can select $C_H$ genes from more than one individual of a species (e.g., allogeneic $C_H$ genes) and incorporate said genes in the transgene as supernumerary $C_H$ genes capable of undergoing isotype switching; the resultant transgenic nonhuman animal may then, in some embodiments, make antibodies of various classes including all of the allotypes represented in the species from which the transgene $C_H$ genes were obtained.

Still further, those skilled in the art can select $C_H$ genes from different species to incorporate into the transgene. Functional switch sequences are included with each $C_H$ gene, although the switch sequences used are not necessarily those which occur naturally adjacent to the $C_H$ gene. Interspecies $C_H$ gene combinations will produce a transgenic nonhuman animal which may produce antibodies of various classes corresponding to $C_H$ genes from various species. Transgenic nonhuman animals containing interspecies $C_H$ transgenes may serve as the source of B-cells for constructing hybridomas to produce monoclonals for veterinary uses.

The heavy chain J region segments in the human comprise six functional J segments and three pseudo genes clustered in a 3 kb stretch of DNA. Given its relatively compact size and the ability to isolate these segments together with the μ gene and the 5' portion of the δ gene on a single 23 kb SFiI/SpeI fragment (Sado et al., *Biochem. Biophys. Res. Comm.* 154: 264271 (1988), which is incorporated herein by reference), it is preferred that all of the J region gene segments be used in the mini-locus construct. Since this fragment spans the region between the μ and δ genes, it is likely to contain all of the 3' cis-linked regulatory elements required for μ expression. Furthermore, because this fragment includes the entire J region, it contains the heavy chain enhancer and the μ switch region (Mills et al., *Nature* 306: 809 (1983); Yancopoulos and Alt, *Ann. Rev. Immunol.* 4: 339–368 (1986), which are incorporated herein by reference). It also contains the transcription start sites which trigger VDJ joining to form primary repertoire B-cells (Yancopoulos and Alt, *Cell* 40: 271–281 (1985), which is incorporated herein by reference). Alternatively, a 36 kb BssHII/SpeII fragment, which includes part on the D region, may be used in place of the 23 kb SfiI/SpeII fragment. The use of such a fragment increases the amount of 5' flanking sequence to facilitate efficient D-to-J joining.

Figure 4:
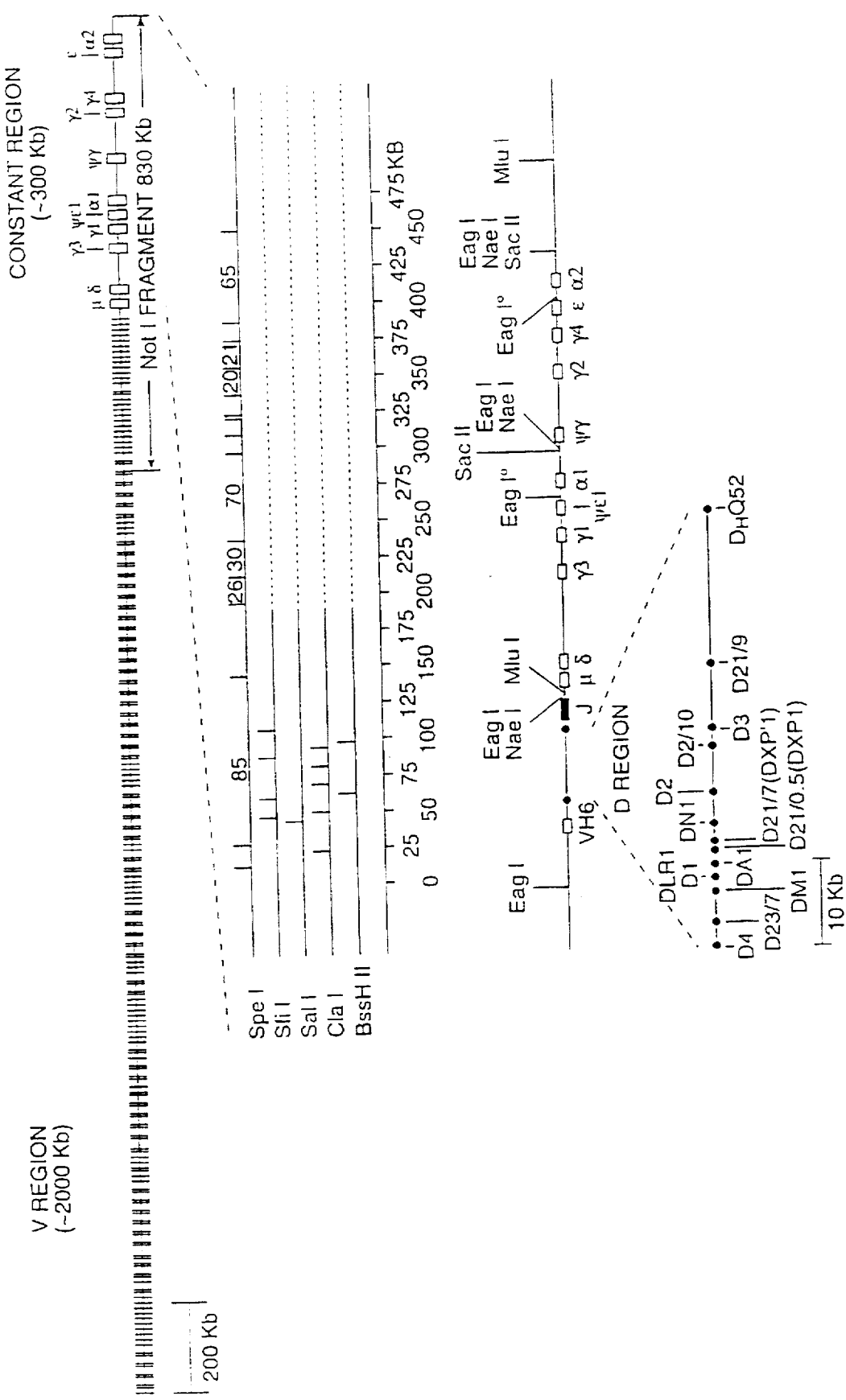
FIG. 4 depicts the human heavy chain locus.
Figure 5:
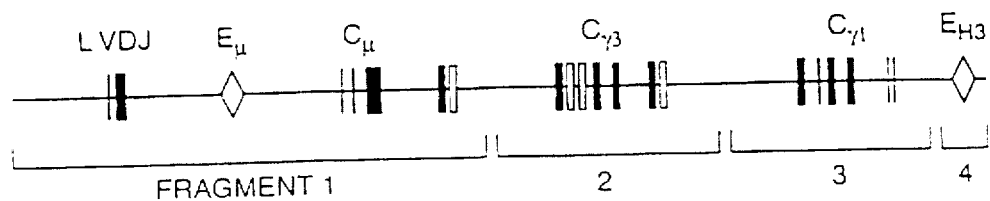
FIG. 5 depicts a transgene construct containing a rearranged IgM gene ligated to a 25 kb fragment that contains human γ3 and γ1 constant regions followed by a 700 bp fragment containing the rat chain 3' enhancer sequence.
Figure 6:
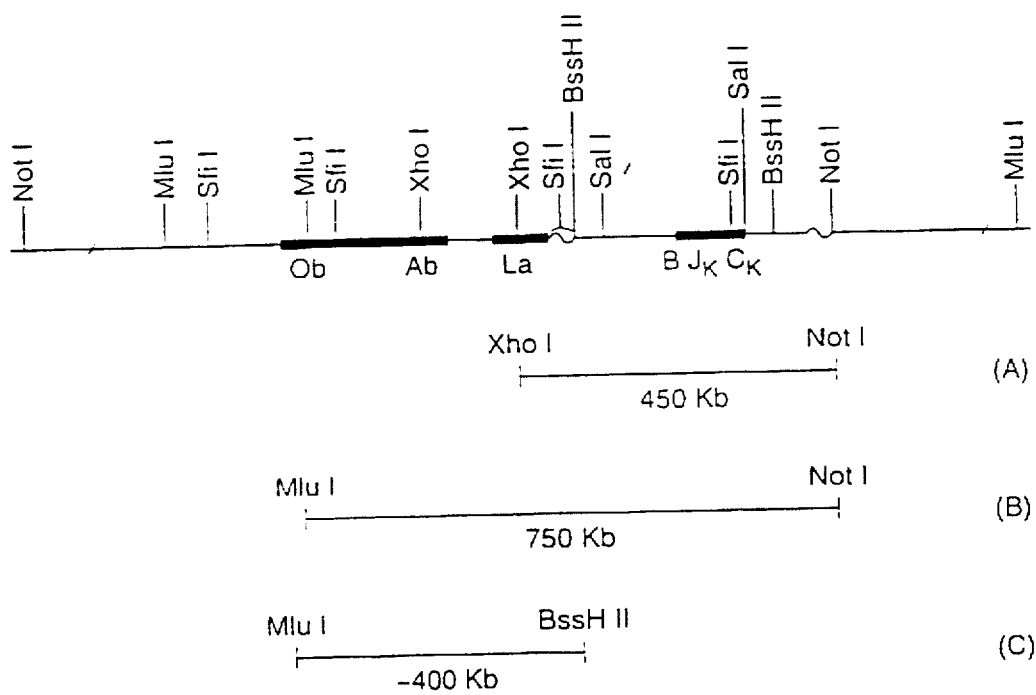
FIG. 6 is a restriction map of the human κ chain locus depicting the fragments to be used to form a light chain transgene by way of in vivo homologous recombination.
Figure 7:
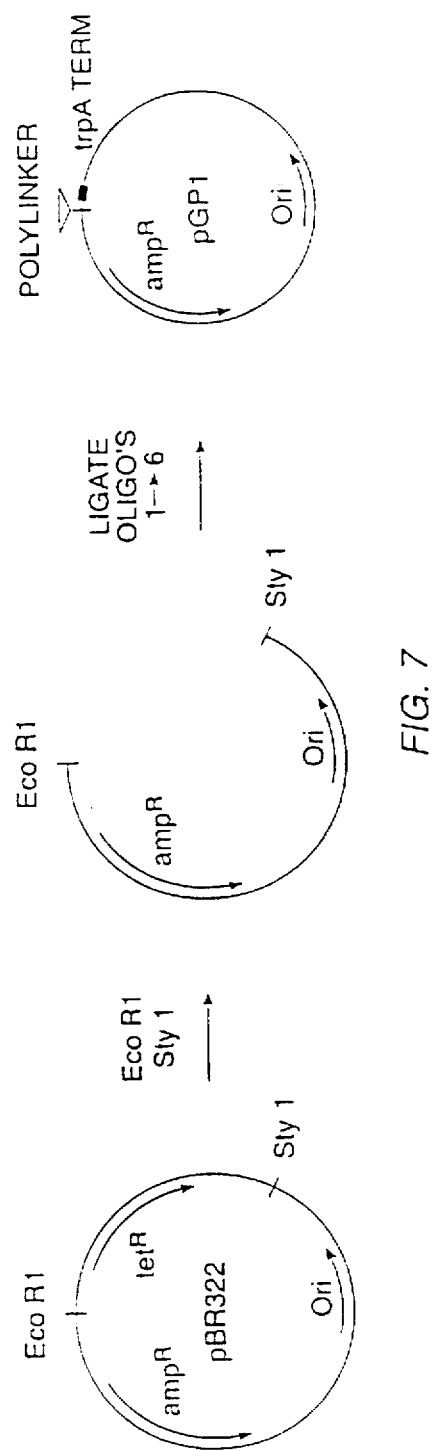
FIG. 7 depicts the construction of pGP1.

The human D region consists of 4 or 5 homologous 9 kb subregions, linked in tandem (Siebenlist, et al. (1981), *Nature*, 294, 631–635). Each subregion contains up to 10 individual D segments. Some of these segments have been mapped and are shown in FIG. 4. Two different strategies are used to generate a mini-locus D region. The first strategy involves using only those D segments located in a short contiguous stretch of DNA that includes one or two of the repeated D subregions. A candidate is a single 15 kb fragment that contains 12 individual D segments. This piece of DNA consists of 2 contiguous EcoRI fragments and has been completely sequenced (Ichihara, et al. (1988), *EMBO J.*, 7, 4141–4150). Twelve D segments should be sufficient for a primary repertoire. However, given the dispersed nature of the D region, an alternative strategy is to ligate together several non-contiguous D-segment containing fragments, to produce a smaller piece of DNA with a greater number of segments. Additional D-segment genes can be identified, for example, by the presence of characteristic flanking nonamer and heptamer sequences, supra, and by reference to the literature.

At least one, and preferably more than one V gene segment is used to construct the heavy chain minilocus transgene. Rearranged or unrearranged V segments with or without flanking sequences can be isolated as described in copending applications, U.S. Ser. No. 07/574,748 filed Aug. 29, 1990, PCT/US91/06185 filed Aug. 28, 1991, and U.S. Ser. No. 07/810,279 filed Dec. 17, 1991, each of which is incorporated herein by reference.

Rearranged or unrearranged V segments, D segments, J segments, and C genes, with or without flanking sequences, can be isolated as described in copending applications U.S. Ser. No. 07/574,748 filed Aug. 29, 1990 and PCT/US91/06185 filed Aug. 28, 1991.

A minilocus light chain transgene may be similarly constructed from the human λ or κ immunoglobulin locus. Thus, for example, an immunoglobulin heavy chain minilocus transgene construct, e.g., of about 75 kb, encoding V, D, J and constant region sequences can be formed from a plurality of DNA fragments, with each sequence being substantially homologous to human gene sequences. Preferably, the sequences are operably linked to transcription regulatory sequences and are capable of undergoing rearrangement. With two or more appropriately placed constant region sequences (e.g., μ and γ) and switch regions, switch recombination also occurs. An exemplary light chain transgene construct can be formed similarly from a plurality of DNA fragments, substantially homologous to human DNA and capable of undergoing rearrangement, as described in copending application, U.S. Ser. No. 07/574,748 filed Aug. 29, 1990.

E. Transgene Constructs Capable of Isotype Switching

Ideally, transgene constructs that are intended to undergo class switching should include all of the cis-acting sequences necessary to regulate sterile transcripts. Naturally occurring switch regions and upstream promoters and regulatory sequences (e.g., IFN-inducible elements) are preferred cis-acting sequences that are included in transgene constructs capable of isotype switching. About at least 50 basepairs, preferably about at least 200 basepairs, and more preferably at least 500 to 1000 basepairs or more of sequence immediately upstream of a switch region, preferably a human γ1 switch region, should be operably linked to a switch sequence, preferably a human γ1 switch sequence. Further, switch regions can be linked upstream of (and adjacent to) $C_H$ genes that do not naturally occur next to the particular switch region. For example, but not for limitation, a human $\gamma_1$ switch region may be linked upstream from a human $\alpha_2$ $C_H$ gene, or a murine γ1 switch may be linked to a human $C_H$ gene.

An alternative method for obtaining non-classical isotype switching (e.g., δ-associated deletion) in transgenic mice involves the inclusion of the 400 bp direct repeat sequences (σμ and εμ) that flank the human μ gene (Yasui et al., *Eur. J. Immunol.* 19: 1399 (1989)). Homologous recombination between these two sequences deletes the μ gene in IgD-only B-cells. Heavy chain transgenes can be represented by the following formulaic description:

$(V_H)_x\text{-}(D)_y\text{-}(J_H)_z\text{-}(S_D)_m\text{-}(C_1)_n\text{-}[(T)\text{-}(S_A)_p\text{-}(C_2)]_q$ where:
- $V_H$ is a heavy chain variable region gene segment,
- D is a heavy chain D (diversity) region gene segment,
- $J_H$ is a heavy chain J (joining) region gene segment,
- $S_D$ is a donor region segment capable of participating in a recombination event with the $S_a$ acceptor region segments such that isotype switching occurs.

$C_1$ is a heavy chain constant region gene segment encoding an isotype utilized in for B cell development (e.g., μ or δ).

T is a cis-acting transcriptional regulatory region segment containing at least a promoter.

$S_A$ is an acceptor region segment capable of participating in a recombination event with selected $S_D$ donor region segments, such that isotype switching occurs.

$C_2$ is a heavy chain constant region gene segment encoding an isotype other than μ (e.g., $\gamma_1$, $\gamma_2$, $\gamma_3$, $\gamma_4$, $\alpha_1$, $\alpha_2$, ε).

x, y, z, m, n, p, and q are integers. x is 1–100, n is 0–10, y is 1–50, p is 1–10, z is 1–50, q is 0–50, m is 0–10. Typically, when the transgene is capable of isotype switching, q must be at least 1, m is at least 1, n is at least 1, and m is greater than or equal to n.

$V_H$, D, $J_H$, $S_D$, $C_1$, T, $S_A$, and $C_Z$ segments may be selected from various species, preferably mammalian species, and more preferably from human and murine germline DNA.

$V_H$ segments may be selected from various species, but are preferably selected from $V_H$ segments that occur naturally in the human germline, such as $V_{H105}$ and $V_{H251}$. Typically about 2 $V_H$ gene segments are included, preferably about 4 $V_H$ segments are included, and most preferably at least about 10 $V_H$ segments are included.

At least one D segment is typically included, although at least 10 D segments are preferably included, and some embodiments include more than ten D segments. Some preferred embodiments include human D segments.

Typically at least one $J_H$ segment is incorporated in the transgene, although it is preferable to include about six $J_H$ segments, and some preferred embodiments include more than about six $J_H$ segments. Some preferred embodiments include human $J_H$ segments, and further preferred embodiments include six human $J_H$ segments and no nonhuman $J_H$ segments.

$S_D$ segments are donor regions capable of participating in recombination events with the $S_A$ segment of the transgene. For classical isotype switching, $S_D$ and $S_A$ are switch regions such as $S_\mu$, $S_{\gamma1}$, $S_{\gamma2}$, $S_{\gamma3}$, $S_{\gamma4}$, $S_\alpha$, $S_{\alpha2}$, and $S_\epsilon$. Preferably the switch regions are murine or human, more preferably $S_D$ is a human or murine $S_\mu$ and $S_A$ is a human or murine $S_{\gamma1}$. For nonclassical isotype switching (δ-associated deletion), $S_D$ and $S_A$ are preferably the 400 basepair direct repeat sequences that flank the human μ gene.

$C_1$ segments are typically μ or δ genes, preferably a μ gene, and more preferably a human or murine μ gene.

T segments typically include 5' flanking sequences that are adjacent to naturally occurring (i.e., germline) switch regions. T segments typically at least about at least 50 nucleotides in length, preferably about at least 200 nucleotides in length, and more preferably at least 500–1000 nucleotides in length. Preferably T segments are 5' flanking sequences that occur immediately upstream of human or murine switch regions in a germline configuration. It is also evident to those of skill in the art that T segments may comprise cis-acting transcriptional regulatory sequences that do not occur naturally in an animal germline (e.g., viral enhancers and promoters such as those found in SV40, adenovirus, and other viruses that infect eukaryotic cells).

$C_2$ segments are typically a $\gamma_1$, $\gamma_2$, $\gamma_3$, $\gamma_4$, $\alpha_1$, $\alpha_2$, or $\epsilon C_H$ gene, preferably a human $C_H$ gene of these isotypes, and more preferably a human $\gamma_1$ or $\gamma_3$ gene. Murine $\gamma_{2a}$ and $\gamma_{2b}$ may also be used, as may downstream (i.e., switched) isotype genes form various species. Where the heavy chain transgene contains an immunoglobulin heavy chain minilocus, the total length of the transgene will be typically 150 kilo basepairs or less.

In general, the transgene will be other than a native heavy chain Ig locus. Thus, for example, deletion of unnecessary regions or substitutions with corresponding regions from other species will be present.

F. Methods for Determining Functional Isotype Switching in Ig Transgenes

The occurrence of isotype switching in a transgenic nonhuman animal may be identified by any method known to those in the art. Preferred embodiments include the following, employed either singly or in combination:

1. detection of mRNA transcripts that contain a sequence homologous to at least one transgene downstream $C_H$ gene other than δ and an adjacent sequence homologous to a transgene $V_H$-$D_H$-$J_H$ rearranged gene; such detection may be by Northern hybridization, $S_1$ nuclease protection assays, PCR amplification, cDNA cloning, or other methods;

2. detection in the serum of the transgenic animal, or in supernatants of cultures of hybridoma cells made from B-cells of the transgenic animal, of immunoglobulin proteins encoded by downstream $C_H$ genes, where such proteins can also be shown by immunochemical methods to comprise a functional variable region;

3. detection, in DNA from B-cells of the transgenic animal or in genomic DNA from hybridoma cells, of DNA rearrangements consistent with the occurrence of isotype switching in the transgene, such detection may be accomplished by Southern blot hybridization, PCR amplification, genomic cloning, or other method; or 4. identification of other indicia of isotype switching, such as production of sterile transcripts, production of characteristic enzymes involved in switching (e.g., "switch recombinase"), or other manifestations that may be detected, measured, or observed by contemporary techniques.

Because each transgenic line may represent a different site of integration of the transgene, and a potentially different tandem array of transgene inserts, and because each different configuration of transgene and flanking DNA sequences can affect gene expression, it is preferable to identify and use lines of mice that express high levels of human immunoglobulins, particularly of the IgG isotype, and contain the least number of copies of the transgene. Single copy transgenics minimize the potential problem of incomplete allelic expression. Transgenes are typically integrated into host chromosomal DNA, most usually into germline DNA and propagated by subsequent breeding of germline transgenic breeding stock animals. However, other vectors and transgenic methods known in the present art or subsequently developed may be substituted as appropriate and as desired by a practitioner.

G. Functional Disruption of Endogenous Immunoglobulin Loci

The expression of successfully rearranged immunoglobulin heavy and light transgenes is expected to have a dominant effect by suppressing the rearrangement of the endogenous immunoglobulin genes in the transgenic nonhuman animal. However, another way to generate a nonhuman that is devoid of endogenous antibodies is by mutating the endogenous immunoglobulin loci. Using embryonic stem cell technology and homologous recombination, the endogenous immunoglobulin repertoire can be readily eliminated. The following describes the functional description of the mouse immunoglobulin loci. The vectors and methods disclosed, however, can be readily adapted for use in other non-human animals.

Briefly, this technology involves the inactivation of a gene, by homologous recombination, in a pluripotent cell line that is capable of differentiating into germ cell tissue. A DNA construct that contains an altered, copy of a mouse immunoglobulin gene is introduced into the nuclei of embryonic stem cells. In a portion of the cells, the introduced DNA recombines with the endogenous copy of the mouse gene, replacing it with the altered copy. Cells containing the newly engineered genetic lesion are injected into a host mouse embryo, which is reimplanted into a recipient female. Some of these embryos develop into chimeric mice that possess germ cells entirely derived from the mutant cell line. Therefore, by breeding the chimeric mice it is possible to obtain a new line of mice containing the introduced genetic lesion (reviewed by Capecchi (1989), *Science*, 244, 1288–1292).

Because the mouse λ locus contributes to only 5% of the immunoglobulins, inactivation of the heavy chain and/or κ-light chain loci is sufficient. There are three ways to disrupt each of these loci, deletion of the J region, deletion of the J-C intron enhancer, and disruption of constant region coding sequences by the introduction of a stop codon. The last option is the most straightforward, in terms of DNA construct design. Elimination of the µ gene disrupts B-cell maturation thereby preventing class switching to any of the functional heavy chain segments. The strategy for knocking out these loci is outlined below.

To disrupt the mouse µ and κ genes, targeting vectors are used based on the design employed by Jaenisch and co-workers (Zijlstra, et al. (1989), *Nature*, 342, 435–438) for the successful disruption of the mouse β2-microglobulin gene. The neomycin resistance gene (neo), from the plasmid pMCIneo is inserted into the coding region of the target gene. The pMCIneo insert uses a hybrid viral promoter/enhancer sequence to drive neo expression. This promoter is active in embryonic stem cells. Therefore, neo can be used as a selectable marker for integration of the knock-out construct. The HSV thymidine kinase (tk) gene is added to the end of the construct as a negative selection marker against random insertion events (Zijlstra, et al., supra.).

A preferred strategy for disrupting the heavy chain locus is the elimination of the J region. This region is fairly compact in the mouse, spanning only 1.3 kb. To construct a gene targeting vector, a 15 kb KpnI fragment containing all of the secreted A constant region exons from mouse genomic library is isolated. The 1.3 kb J region is replaced with the 1.1 kb insert from pMCIneo. The HSV tk gene is then added to the 5' end of the KpnI fragment. Correct integration of this construct, via homologous recombination, will result in the replacement of the mouse $J_H$ region with the neo gene. Recombinants are screened by PCR, using a primer based on the neo gene and a primer homologous to mouse sequences 5' of the KpnI site in the D region.

Alternatively, the heavy-chain locus is knocked out by disrupting the coding region of the µ gene. This approach involves the same 15 kb KpnI fragment used in the previous approach. The 1.1 kb insert from pMCIneo is inserted at a unique BamHI site in exon II, and the HSV tk gene added to the 3' KpnI end. Double crossover events on either side of the neo insert, that eliminate the tk gene, are then selected for. These are detected from pools of selected clones by PCR amplification. One of the PCR primers is derived from neo sequences and the other from mouse sequences outside of the targeting vector. The functional disruption of the mouse immunoglobulin loci is presented in the Examples.

G. Suppressing Expression of Endogenous Immunoglobulin Loci

In addition to functional disruption of endogenous Ig loci, an alternative method for preventing the expression of an endogenous Ig locus is suppression. Suppression of endogenous Ig genes may be accomplished with antisense RNA produced from one or more integrated transgenes, by antisense oligonucleotides, and/or by administration of antisera specific for one or more endogenous Ig chains.

Antisense Polynucleotides

Antisense RNA transgenes can be employed to partially or totally knock-out expression of specific genes (Pepin et al. (1991) *Nature* 355: 725; Helene., C. and Toulme, J. (1990) *Biochimica Biophys. Acta* 1049: 99; Stout, J. and Caskey, T. (1990) *Somat. Cell Mol. Genet.* 16: 369; Munir et al. (1990) *Somat. Cell Mol. Genet.* 16: 383, each of which is incorporated herein by reference).

"Antisense polynucleotides" are polynucleotides that: (1) are complementary to all or part of a reference sequence, such as a sequence of an endogenous Ig $C_H$ or $C_L$ region, and (2) which specifically hybridize to a complementary target sequence, such as a chromosomal gene locus or a Ig mRNA. Such complementary antisense polynucleotides may include nucleotide substitutions, additions, deletions, or transpositions, so long as specific hybridization to the relevant target sequence is retained as a functional property of the polynucleotide. Complementary antisense polynucleotides include soluble antisense RNA or DNA oligonucleotides which can hybridize specifically to individual mRNA species and prevent transcription and/or RNA processing of the mRNA species and/or translation of the encoded polypeptide (Ching et al., *Proc. Natl. Acad. Sci. U.S.A.* 86: 10006–10010 (1989); Broder et al., *Ann. Int. Med.* 113: 604–618 (1990); Loreau et al., *FEBS Letters* 274: 53–56 (1990); Holcenberg et al., WO91/11535; U.S. Ser. No. 07/530,165 ("New human CRIPTO gene"); WO91/09865; WO91/04753; WO90/13641; and EP 386563, each of which is incorporated herein by reference). An antisense sequence is a polynucleotide sequence that is complementary to at least one immunoglobulin gene sequence of at least about 15 contiguous nucleotides in length, typically at least 20 to 30 nucleotides in length, and preferably more than about 30 nucleotides in length. However, in some embodiments, antisense sequences may have substitutions, additions, or deletions as compared to the complementary immunoglobulin gene sequence, so long as specific hybridization is retained as a property of the antisense polynucleotide. Generally, an antisense sequence is complementary to an endogenous immunoglobulin gene sequence that encodes, or has the potential to encode after DNA rearrangement, an immunoglobulin chain. In some cases, sense sequences corresponding to an immunoglobulin gene sequence may function to suppress expression, particularly by interfering with transcription.

The antisense polynucleotides therefore inhibit production of the encoded polypeptide(s). In this regard, antisense polynucleotides that inhibit transcription and/or translation of one or more endogenous Ig loci can alter the capacity and/or specificity of a non-human animal to produce immunoglobulin chains encoded by endogenous Ig loci.

Antisense polynucleotides may be produced from a heterologous expression cassette in a transfectant cell or transgenic cell, such as a transgenic pluripotent hematopoietic stem cell used to reconstitute all or part of the hematopoietic stem cell population of an individual, or a transgenic non-human animal. Alternatively, the antisense polynucleotides may comprise soluble oligonucleotides that are administered to the external milieu, either in culture medium in vitro or in the circulatory system or interstitial fluid in vivo. Soluble antisense polynucleotides present in the external milieu have been shown to gain access to the cytoplasm and inhibit translation of specific mRNA species. In some embodiments the antisense polynucleotides comprise methylphosphonate moieties, alternatively phosphorothiolates or O-methylribonucleotides may be used, and chimeric oligonucleotides may also be used (Dagle et al. (1990) *Nucleic Acids Res.* 18: 4751). For some applications, antisense oligonucleotides may comprise polyamide nucleic acids (Nielsen et al. (1991) *Science* 254: 1497). For general methods relating to antisense polynucleotides, see *Antisense RNA and DNA*, (1988), D. A. Melton, Ed., Cold Spring Harbor Laboratory, Cold Spring Harbor, N.Y.).

Antisense polynucleotides complementary to one or more sequences are employed to inhibit transcription, RNA processing, and/or translation of the cognate mRNA species and thereby effect a reduction in the amount of the respective encoded polypeptide. Such antisense polynucleotides can provide a therapeutic function by inhibiting the formation of one or more endogenous Ig chains in vivo.

Whether as soluble antisense oligonucleotides or as antisense RNA transcribed from an antisense transgene, the antisense polynucleotides of this invention are selected so as to hybridize preferentially to endogenous Ig sequences at physiological conditions in vivo. Most typically, the selected antisense polynucleotides will not appreciably hybridize to heterologous Ig sequences encoded by a heavy or light chain transgene of the invention (i.e., the antisense oligonucleotides will not inhibit transgene Ig expression by more than about 25 to 35 percent).

Antiserum Suppression

Partial or complete suppression of endogenous Ig chain expression can be produced by injecting mice with antisera against one or more endogenous Ig chains (Weiss et al. (1984) *Proc. Natl. Acad. Sci.* (U.S.A.) 81 211, which is incorporated herein by reference). Antisera are selected so as to react specifically with one or more endogenous Ig chains but to have minimal or no cross-reactivity with heterologous Ig chains encoded by an Ig transgene of the invention. Thus, administration of selected antisera according to a schedule as typified by that of Weiss et al. op.cit. will suppress endogenous Ig chain expression but permits expression of heterologous Ig chain(s) encoded by a transgene of the present invention.

Nucleic Acids

The nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98 to 99.5% of the nucleotides. Alternatively, substantial homology exists when the segments will hybridize under selective hybridization conditions, to the complement of the strand. The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. *Current Protocols in Molecular Biology*, Greene Publishing and Wiley-Interscience, New York (1987).

The nucleic acid compositions of the present invention, while often in a native sequence (except for modified restriction sites and the like), from either cDNA, genomic or mixtures may be mutated, thereof in accordance with standard techniques to provide gene sequences. For coding sequences, these mutations, may affect amino acid sequence as desired. In particular, DNA sequences substantially homologous to or derived from native V, D, J, constant, switches and other such sequences described herein are contemplated (where "derived" indicates that a sequence is identical or modified from another sequence).

A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

Specific Preferred Embodiments

A preferred embodiment of the invention is an animal containing at least one, typically 2–10, and sometimes 25–50 or more copies of the transgene described in Example 12 (e.g., pHC1 or pHC2) bred with an animal containing a single copy of a light chain transgene described in Examples 5, 6, 8, or 14, and the offspring bred with the $J_H$ deleted animal described in Example 10. Animals are bred to homozygosity for each of these three traits. Such animals have the following genotype: a single copy (per haploid set of chromosomes) of a human heavy chain unrearranged mini-locus (described in Example 12), a single copy (per haploid set of chromosomes) of a rearranged human κ light chain construct (described in Example 14), and a deletion at each endogenous mouse heavy chain locus that removes all of the functional $J_H$ segments (described in Example 10). Such animals are bred with mice that are homozygous for the deletion of the $J_H$ segments (Examples 10) to produce offspring that are homozygous for the $J_H$ deletion and hemizygous for the human heavy and light chain constructs. The resultant animals are injected with antigens and used for production of human monoclonal antibodies against these antigens.

B cells isolated from such an animal are monospecific with regard to the human heavy and light chains because they contain only a single copy of each gene. Furthermore, they will be monospecific with regards to human or mouse heavy chains because both endogenous mouse heavy chain gene copies are nonfunctional by virtue of the deletion spanning the $J_H$ region introduced as described in Example 9 and 12. Furthermore, a substantial fraction of the B cells will be monospecific with regards to the human or mouse light chains because expression of the single copy of the rearranged human κ light chain gene will allelically and isotypically exclude the rearrangement of the endogenous mouse κ and λ chain genes in a significant fraction of B-cells.

The transgenic mouse of the preferred embodiment will exhibit immunoglobulin production with a significant repertoire, ideally substantially similar to that of a native mouse. Thus, for example, in embodiments where the endogenous Ig genes have been inactivated, the total immunoglobulin levels will range from about 0.1 to 10 mg/ml of serum, preferably 0.5 to 5 mg/ml, ideally at least about 1.0 mg/ml. When a transgene capable of effecting a switch to IgG from IgM has been introduced into the transgenic mouse, the adult mouse ratio of serum IgG to IgM is preferably about 10:1. Of course, the IgG to IgM ratio will be much lower in the immature mouse. In general, greater than about 10%, preferably 40 to 80% of the spleen and lymph node B cells express exclusively human IgG protein.

The repertoire will ideally approximate that shown in a non-transgenic mouse, usually at least about 10% as high, preferably 25 to 50% or more. Generally, at least about a thousand different immunoglobulins (ideally IgG), preferably $10^4$ to $10^6$ or more, will be produced, depending primarily on the number of different V, J and D regions introduced into the mouse genome. These immunoglobulins will typically recognize about one-half or more of highly antigenic proteins, including, but not limited to: pigeon cytochrome C, chicken lysozyme, pokeweed mitogen, bovine serum albumin, keyhole limpit hemocyanin, influenza hemagglutinin, staphylococcus protein A, sperm whale myoglobin, influenza neuraminidase, and lambda repressor protein. Some of the immunoglobulins will exhibit an affinity for preselected antigens of at least about $10^7 M^{-1}$, preferably $10^8 M^{-1}$ to $10^9 M^{-1}$ or greater.

Thus, prior to rearrangement of a transgene containing various heavy or light chain gene segments, such gene segments may be readily identified, e.g. by hybridization or DNA sequencing, as being from a species of organism other than the transgenic animal.

Although the foregoing describes a preferred embodiment of the transgenic animal of the invention, other embodiments are defined by the disclosure herein and more particularly by the transgenes described in the Examples. Four categories of transgenic animal may be defined:

I. Transgenic animals containing an unrearranged heavy and rearranged light immunoglobulin transgene.

II. Transgenic animals containing an unrearranged heavy and unrearranged light immunoglobulin transgene III. Transgenic animal containing rearranged heavy and an unrearranged light immunoglobulin transgene, and IV. Transgenic animals containing rearranged heavy and rearranged light immunoglobulin transgenes.

Of these categories of transgenic animal, the preferred order of preference is as follows II>I>III>IV where the endogenous light chain genes (or at least the κ gene) have been knocked out by homologous recombination (or other method) and I>II>III>IV where the endogenous light chain genes have not been knocked out and must be dominated by allelic exclusion.

EXPERIMENTAL EXAMPLES

METHODS AND MATERIALS

Transgenic mice are derived according to Hogan, et al., "Manipulating the Mouse Embryo: A Laboratory Manual", Cold Spring Harbor Laboratory, which is incorporated herein by reference.

Embryonic stem cells are manipulated according to published procedures (Teratocarcinomas and embryonic stem cells: a practical approach, E. J. Robertson, ed., IRL Press, Washington, D.C., 1987; Zjilstra et al., Nature 342: 435–438 (1989); and Schwartzberg et al., Science 246: 799–803 (1989), each of which is incorporated herein by reference).

DNA cloning procedures are carried out according to J. Sambrook, et al. in Molecular Cloning: A Laboratory Manual, 2d ed., 1989, Cold Spring Harbor Laboratory Press, Cold Spring Harbor, N.Y., which is incorporated herein by reference.

Oligonucleotides are synthesized on an Applied Bio Systems oligonucleotide synthesizer according to specifications provided by the manufacturer.

Hybridoma cells and antibodies are manipulated according to "Antibodies: A Laboratory Manual", Ed Harlow and David Lane, Cold Spring Harbor Laboratory (1988), which is incorporated herein by reference.

EXAMPLE 1

Genomic Heavy Chain Human Ig Transgene

This Example describes the cloning and microinjection of a human genomic heavy chain immunoglobulin transgene which is microinjected into a murine zygote.

Nuclei are isolated from fresh human placental tissue as described by Marzluff et al., "Transcription and Translation: A Practical Approach", B. D. Hammes and S. J. Higgins, eds., pp. 89–129, IRL Press, Oxford (1985)). The isolated nuclei (or PBS washed human spermatocytes) are embedded in a low melting point agarose matrix and lysed with EDTA and proteinase κ to expose high molecular weight DNA, which is then digested in the agarose with the restriction enzyme NotI as described by M. Finney in Current Protocols in Molecular Biology (F. Ausubel, et al., eds. John Wiley & Sons, Supp. 4, 1988, Section 2.5.1).

The NotI digested DNA is then fractionated by pulsed field gel electrophoresis as described by Anand et al., Nucl. Acids Res. 17: 3425–3433 (1989). Fractions enriched for the NotI fragment are assayed by Southern hybridization to detect one or more of the sequences encoded by this fragment. Such sequences include the heavy chain D segments, J segments, μ and γ1 constant regions together with representatives of all 6 VH families (although this fragment is identified as 670 kb fragment from HeLa cells by Berman et al. (1988), supra., we have found it to be as 830 kb fragment from human placental an sperm DNA). Those fractions containing this NotI fragment (see FIG. 4) are pooled and cloned into the NotI site of the vector pYACNN in Yeast cells. Plasmid pYACNN is prepared by digestion of pYAC-4 Neo (Cook et al., Nucleic Acids Res. 16: 11817 (1988)) with EcoRI and ligation in the presence of the oligonucleotide 5'-AAT TGC GGC CGC - 3'(SEG ID NO:9).

YAC clones containing the heavy chain NotI fragment are isolated as described by Brownstein et al., Science 244: 1348–1351 (1989), and Green et al., Proc. Natl. Acad. Sci. USA 87: 1213–1217 (1990), which are incorporated herein by reference. The cloned NotI insert is isolated from high molecular weight yeast DNA by pulse field gel electrophoresis as described by M. Finney, op cit. The DNA is condensed by the addition of 1 mM spermine and microinjected directly into the nucleus of single cell embryos previously described.

EXAMPLE 2

Genomic κ Light Chain Human Ig Transgene Formed by In Vivo Homologous Recombination A map of the human κ light chain has been described in Lorenz et al., Nucl. Acids Res. 15: 9667–9677 (1987), which is incorporated herein by reference.

A 450 kb XhoI to NotI fragment that includes all of $C_\kappa$, the 3' enhancer, all J segments, and at least five different V segments is isolated and microinjected into the nucleus of single cell embryos as described in Example 1.

EXAMPLE 3

Genomic κ Light Chain Human Ig Transgene Formed by In Vivo Homologous Recombination A 750 kb MluI to NotI fragment that includes all of the above plus at least 20 more V segments is isolated as described in Example 1 and digested with BssHII to produce a fragment of about 400 kb.

The 450 kb XhoI to NotI fragment plus the approximately 400 kb MluI to BssHII fragment have sequence overlap defined by the BssHII and XhoI restriction sites. Homologous recombination of these two fragments upon microinjection of a mouse zygote results in a transgene containing at least an additional 15–20 V segments over that found in the 450 kb XhoI/NotI fragment (Example 2).

EXAMPLE 4

Construction of Heavy Chain Mini-Locus

Figure 8:
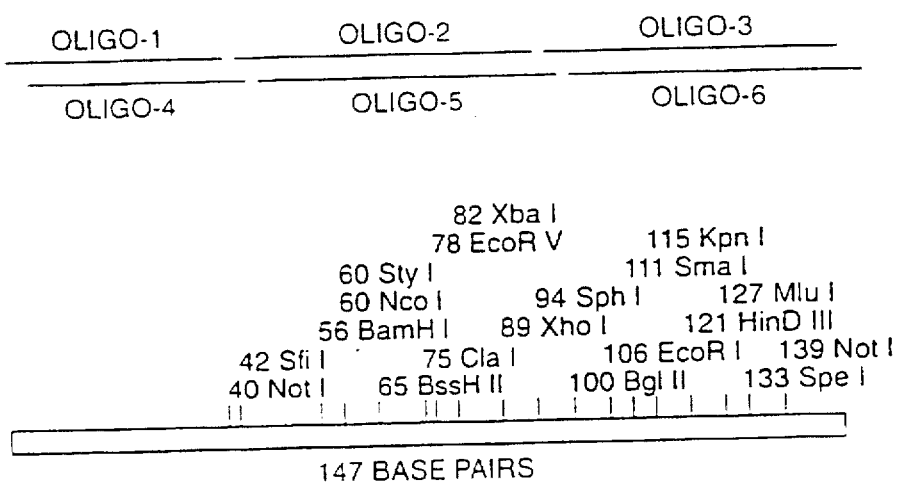
FIG. 8 depicts the construction of the polylinker contained in pGP1.
Figure 9:
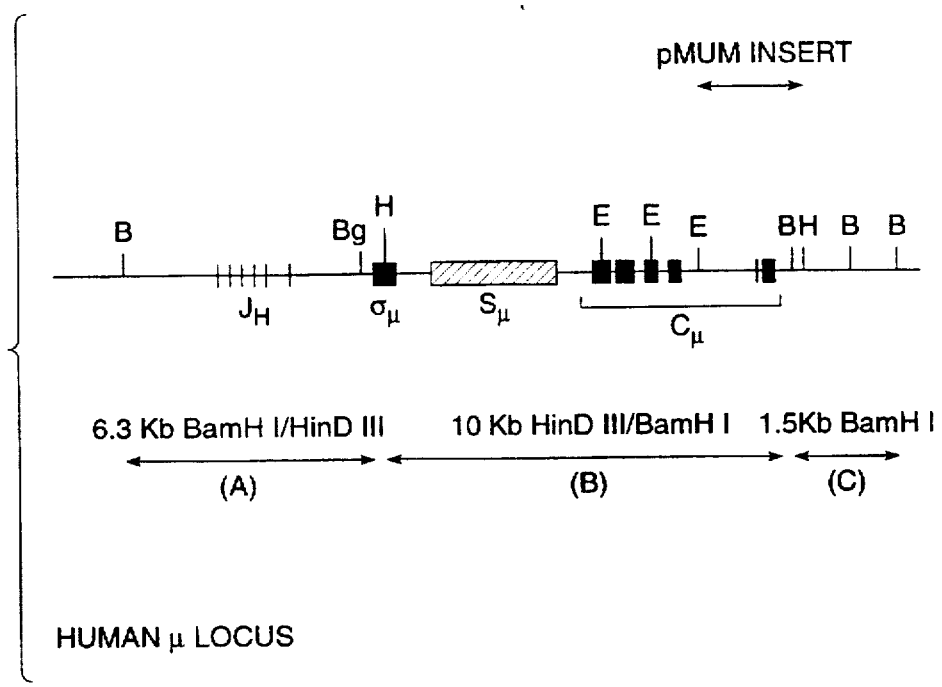
FIG. 9 depicts the fragments used to construct a human heavy chain transgene of the invention.

A. Construction of PGP1 and PGP2 pBR322 is digested with EcoRI and StyI and ligated with the following oligonucleotides to generate pGP1 which contains a 147 base pair insert containing the restriction sites shown in FIG. 8. The general overlapping of these oligos is also shown in FIG. 9.

The oligonucleotides are:
oligo-1 5'- CTT GAG CCC GCC TAA TGA GCG GGC TTT TTT TTG CAT ACT GCG GCC - 3'(SEG ID NO:10)
oligo-2 5'- GCA ATG GCC TGG ATC CAT GGC GCG CTA GCA TCG ATA TCT AGA GCT CGA GCA -3'(SEG ID NO:11)
oligo-3 5'- TGC AGA TCT GAA TTC CCG GGT ACC AAG CTT ACG CGT ACT AGT GCG GCC GCT -3'(SEG ID NO:12)
oligo-4 5'- AAT TAG CGG CCG CAC TAG TAC GCG TAA GCT TGG TAC CCG GGA ATT - 3'(SEG ID NO:13)
oligo-5 5'- CAG ATC TGC ATG CTC GAG CTC TAG ATA TCG ATG CTA GCG CGC CAT GGA TCC - 3'(SEG ID NO:14)
oligo-6 5'- AGG CCA TTG CGG CCG CAG TAT GCA AAA AAA AGC CCG CTC ATT AGG CGG GCT - 3'(SEG ID NO:15)

This plasmid contains a large polylinker flanked by rare cutting NotI sites for building large inserts that can be isolated from vector sequences for microinjection. The plasmid is based on pBR322 which is relatively low copy compared to the pUC based plasmids (pGP1 retains the pBR322 copy number control region near the origin of replication). Low copy number reduces the potential toxicity of insert sequences. In addition, pGP1 contains a strong transcription terminator sequence derived from trpA (Christie et al., Proc. Natl. Acad. Sci. USA 78: 4180 (1981)) inserted between the ampicillin resistance gene and the polylinker. This further reduces the toxicity associated with certain inserts by preventing readthrough transcription coming from the ampicillin promoters.

Plasmid pGP2 is derived from pGP1 to introduce an additional restriction site (SfiI) in the polylinker. pGP1 is digested with MluI and SpeI to cut the recognition sequences in the polylinker portion of the plasmid.

The following adapter oligonucleotides are ligated to the thus digested pGP1 to form pGP2.
5'CGC GTG GCC GCA ATG GCC A 3'(SEG ID NO:16)
5'CTA GTG GCC ATT GCG GCC A 3'(SEQ ID NO:17)

pGP2 is identical to pGP1 except that it contains an additional Sfi I site located between the MluI and SpeI sites. This allows inserts to be completely excised with SfiI as well as with NotI.

B. Construction of pRE3 (rat enhancer 3')

An enhancer sequence located downstream of the rat constant region is included in the heavy chain constructs.

The heavy chain region 3' enhancer described by Petterson et al., Nature 344: 165–168 (1990), which is incorporated herein by reference) is isolated and cloned. The rat IGH 3' enhancer sequence is PCR amplified by using the following oligonucleotides:
5'CAG GAT CCA GAT ATC AGT ACC TGA AAC AGG GCT TGC 3'(SEG ID NO:18)
5'GAG CAT GCA CAG GAC CTG GAG CAC ACA CAG CCT TCC 3'(SEG ID NO:19)

The thus formed double stranded DNA encoding the 3' enhancer is cut with BamHI and SphI and clone into BamHI/SphI cut pGP2 to yield pRE3 (rat enhancer 3').

C. Cloning of Human J-µ Region

A substantial portion of this region is cloned by combining two or more fragments isolated from phage lambda inserts. See FIG. 9.

A 6.3 kb BamHI/HindIII fragment that includes all human J segments (Matsuda et al., EMBO J., 7: 1047–1051 (1988); Ravetech et al.m Cell, 27: 583–591 (1981), which are incorporated herein by reference) is isolated from human genomic DNA library using the oligonucleotide GGA CTG TGT CCC TGT GTG ATG CTT TTG ATG TCT GGG GCC AAG (SEG ID NO:20).

An adjacent 10 kb HindIII/BamII fragment that contains enhancer, switch and constant region coding exons (Yasui et al., Eur. J. Immunol. 19: 1399–1403 (1989)) is similarly isolated using the oligonucleotide:
CAC CAA GTT GAC CTG CCT GGT CAC AGA CCT GAC CAC CTA TGA (SEG ID NO:21)

An adjacent 3' 1.5 kb BamHI fragment is similarly isolated using clone pMUM insert as probe (pMUM is 4 kb EcoRI/HindIII fragment isolated from human genomic DNA library with oligonucleotide:

CCT GTG GAC CAC CGC CTC CAC CTT CAT CGT CCT CTT CCT CCT (SEG ID NO:22)

mu membrane exon 1) and cloned into pUC19.

pGP1 is digested with BamHI and BglII followed by treatment with calf intestinal alkaline phosphatase.

Fragments (a) and (b) from FIG. 9 are cloned in the digested pGP1. A clone is then isolated which is oriented such that 5' BamHI site is destroyed by BamHI/Bgl fusion. It is identified as pMU (see FIG. 10). pMU is digested with BamHI and fragment (c) from FIG. 9 is inserted. The orientation is checked with HindIII digest. The resultant plasmid pHIG1 (FIG. 10) contains an 18 kb insert encoding J nd Cµ segments.

Figure 14:
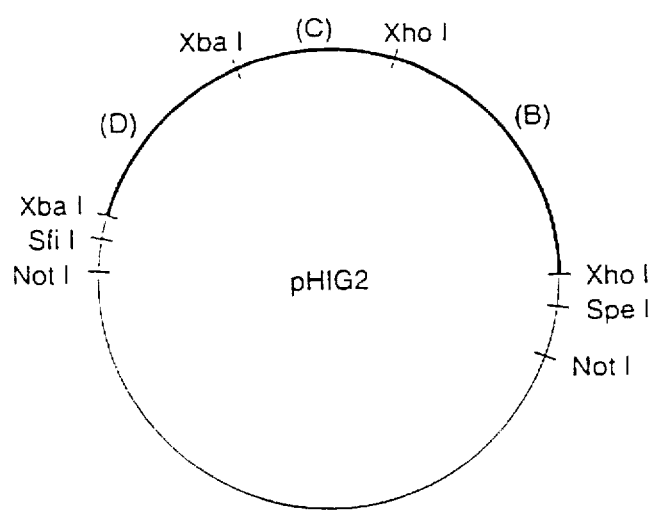
FIG. 14 depicts the construction of pHIG2 (D segment containing plasmid).
Figure 15:
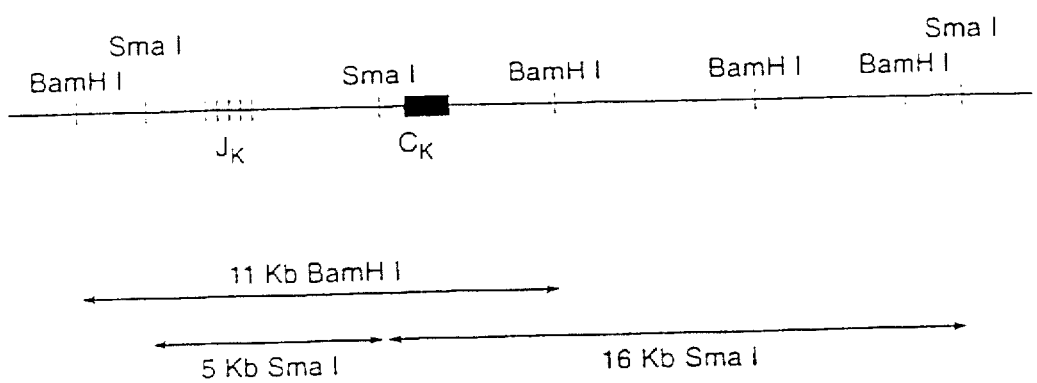
FIG. 15 depicts the fragments covering the human Jκ and human Cκ gene segments used in constructing a transgene of the invention.

D. Cloning of Cµ Region pGP1 is digested with BamHI and HindIII is followed by treatment with calf intestinal alkaline phosphatase (FIG. 14). The so treated fragment (b) of FIG. 14 and fragment (c) of FIG. 14 are cloned into the BamHI/HindIII cut pGP1. Proper orientation of fragment (c) is checked by HindIII digestion to form pCON1 containing a 12 kb insert encoding the Cµ region.

Whereas pHIG1 contains J segments, switch and µ sequences in its 18 kb insert with an SfiI 3' site and a SpeI 5' site in a polylinker flanked by NotI sites, will be used for rearranged VDJ segments. pCON1 is identical except that it lacks the J region and contains only a 12 kb insert. The use of pCON1 in the construction of fragment containing rearranged VDJ segments will be described hereinafter.

E. Cloning of γ-1 Constant Region (pREG2)

Figure 16:
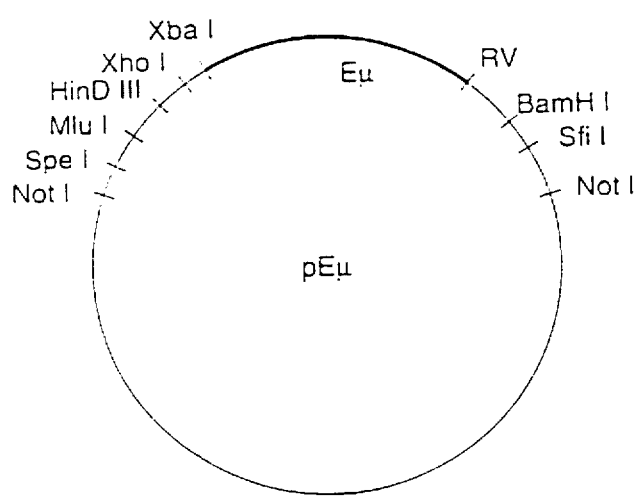
FIG. 16 depicts the structure of pEμ.
Figure 17:
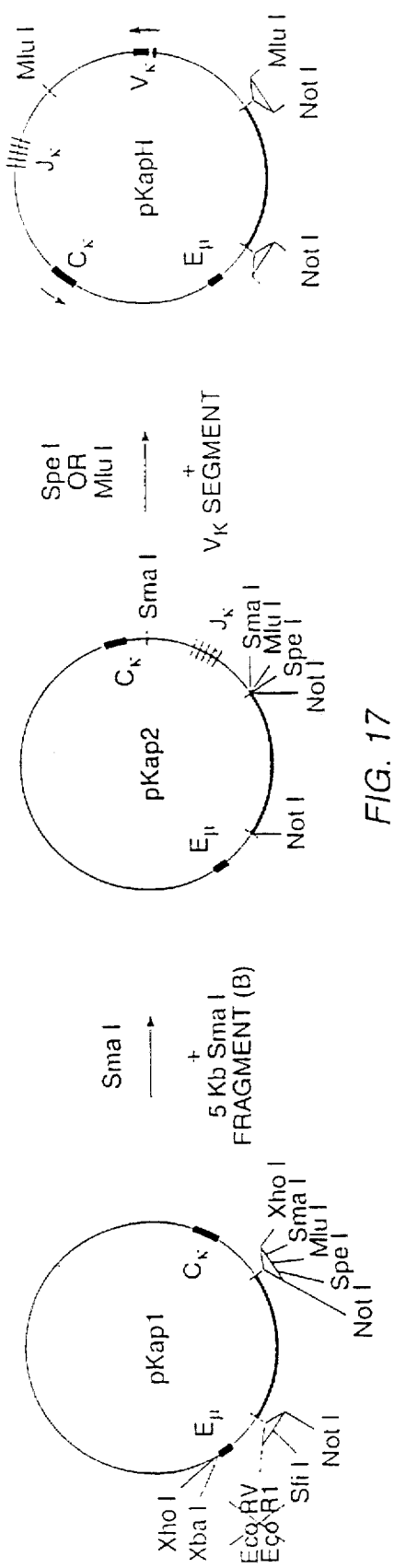
FIG. 17 depicts the construction of pKapH.
Figure 18A:
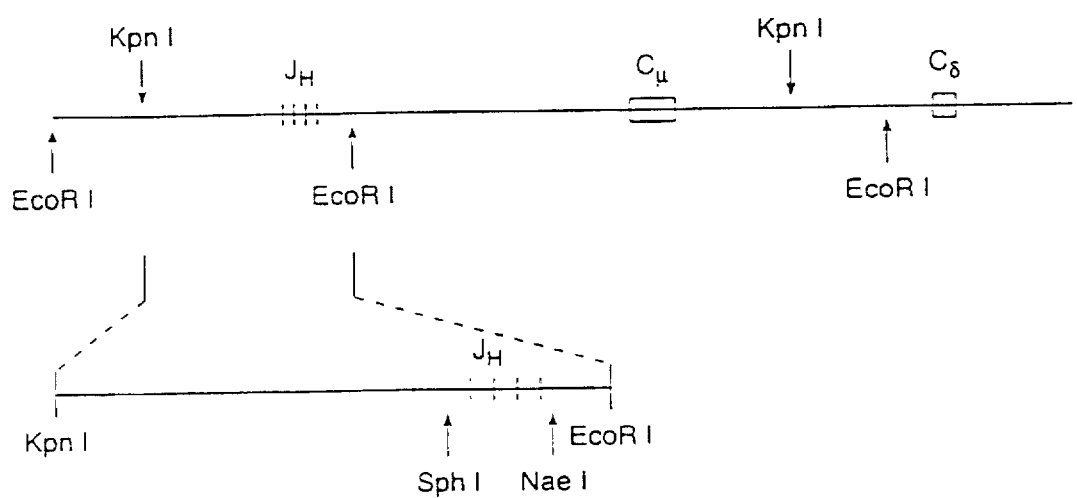
FIGS. 18A through 18D depict the construction of a positive-negative selection vector for functionally disrupting the endogenous heavy chain immunoglobulin locus of mouse.
Figure 18B:
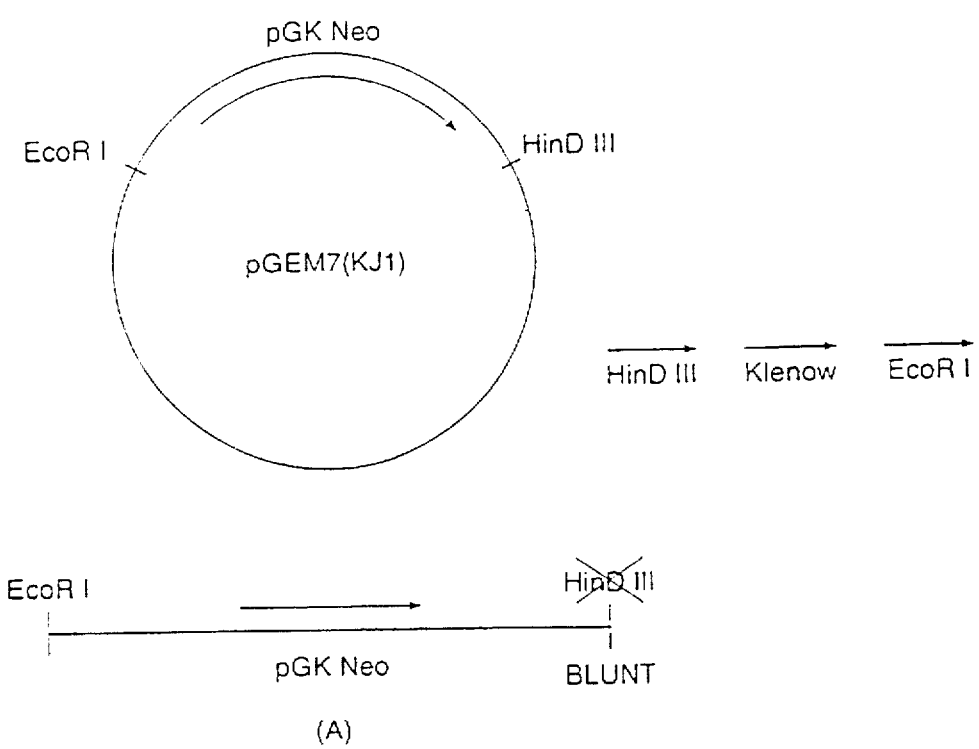
Figure 18C:
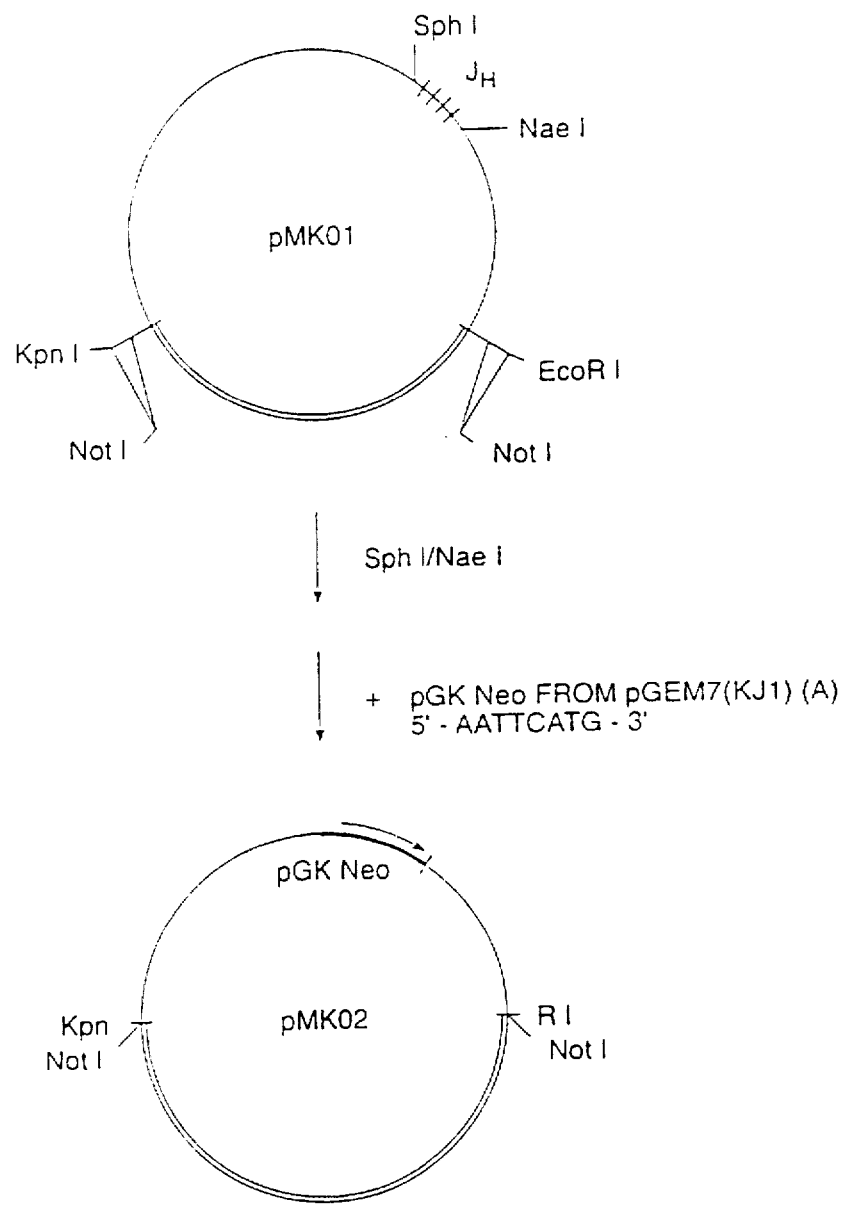
Figure 18D:
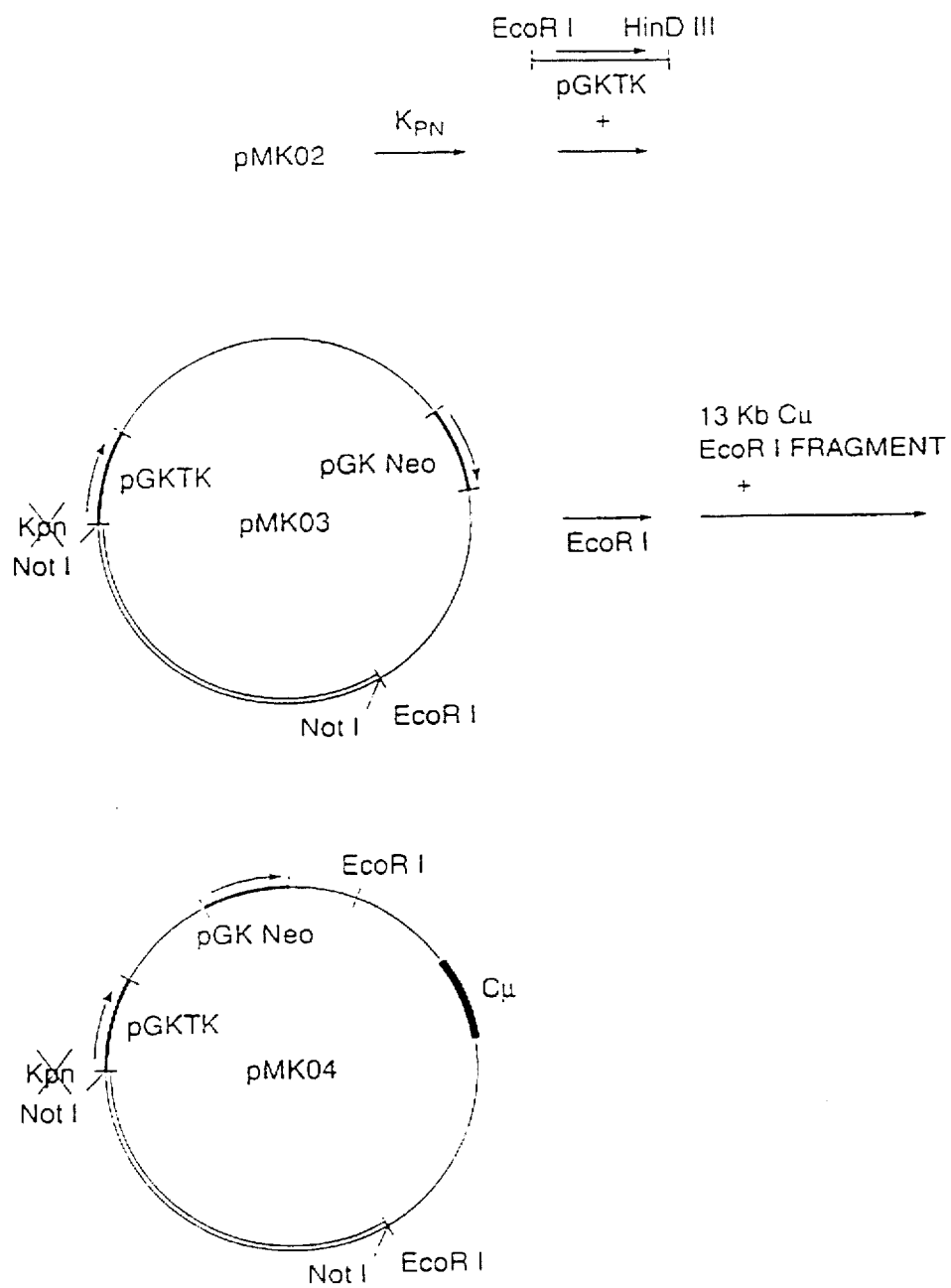
Figure 19A:
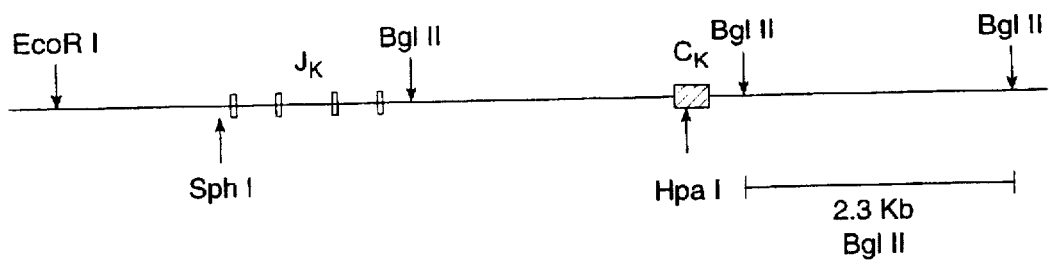
FIGS. 19A through 19C depict the construction of a positive-negative selection vector for functionally disrupting the endogenous immunoglobulin light chain loci in mouse.
Figure 19B:
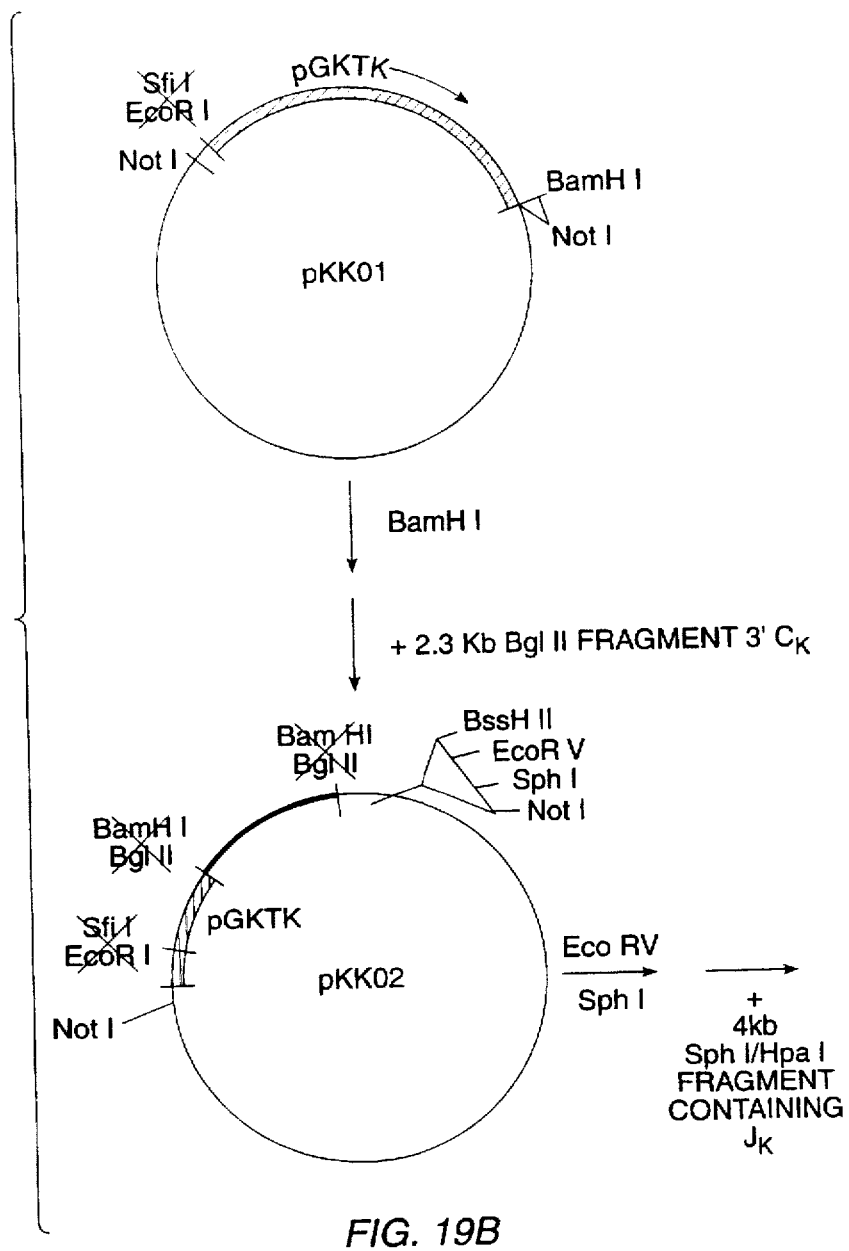
Figure 19C:
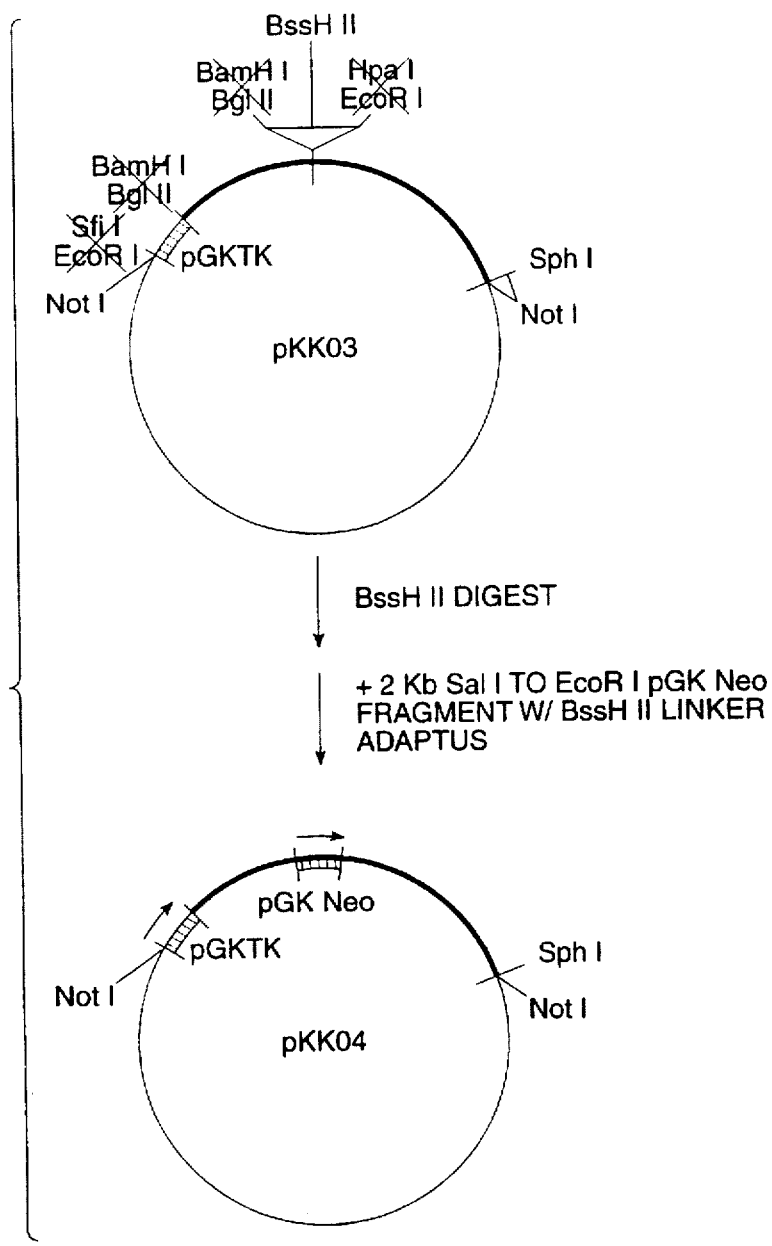

The cloning of the human γ-1 region is depicted in FIG. 16.

Yamamura et al., Proc. Natl. Acad. Sci. USA 83: 2152–2156 (1986) reported the expression of membrane bound human γ-1 from a transgene construct that had been partially deleted on integration. Their results indicate that the 3' BamHI site delineates a sequence that includes the transmembrane rearranged and switched copy of the gamma gene with a V-C intron of less than 5 kb. Therefore, in the unrearranged, unswitched gene, the entire switch region is included in a sequence beginning less than 5 kb from the 5' end of the first γ-1 constant exon. Therefore it is included in the 5' 5.3 kb HindIII fragment (Ellison et al., *Nucleic Acids Res.* 10: 4071–4079 (1982), which is incorporated herein by reference). Takahashi et al., *Cell* 29: 671–679 (1982), which is incorporated herein by reference, also reports that this fragment contains the switch sequence, and this fragment together with the 7.7 kb HindIII to BamHI fragment must include all of the sequences we need for the transgene construct. An intronic sequence is a nucleotide sequence of at least 15 contiguous nucleotides that occurs in an intron of a specified gene.

Phage clones containing the γ-1 region are identified and isolated using the following oligonucleotide which is specific for the third exon of γ-I (CH3).

5'TGA GCC ACG AAG ACC CTG AGG TCA AGT TCA ACT GGT ACG TGG 3'(SEG ID NO:25)

Figure 11:
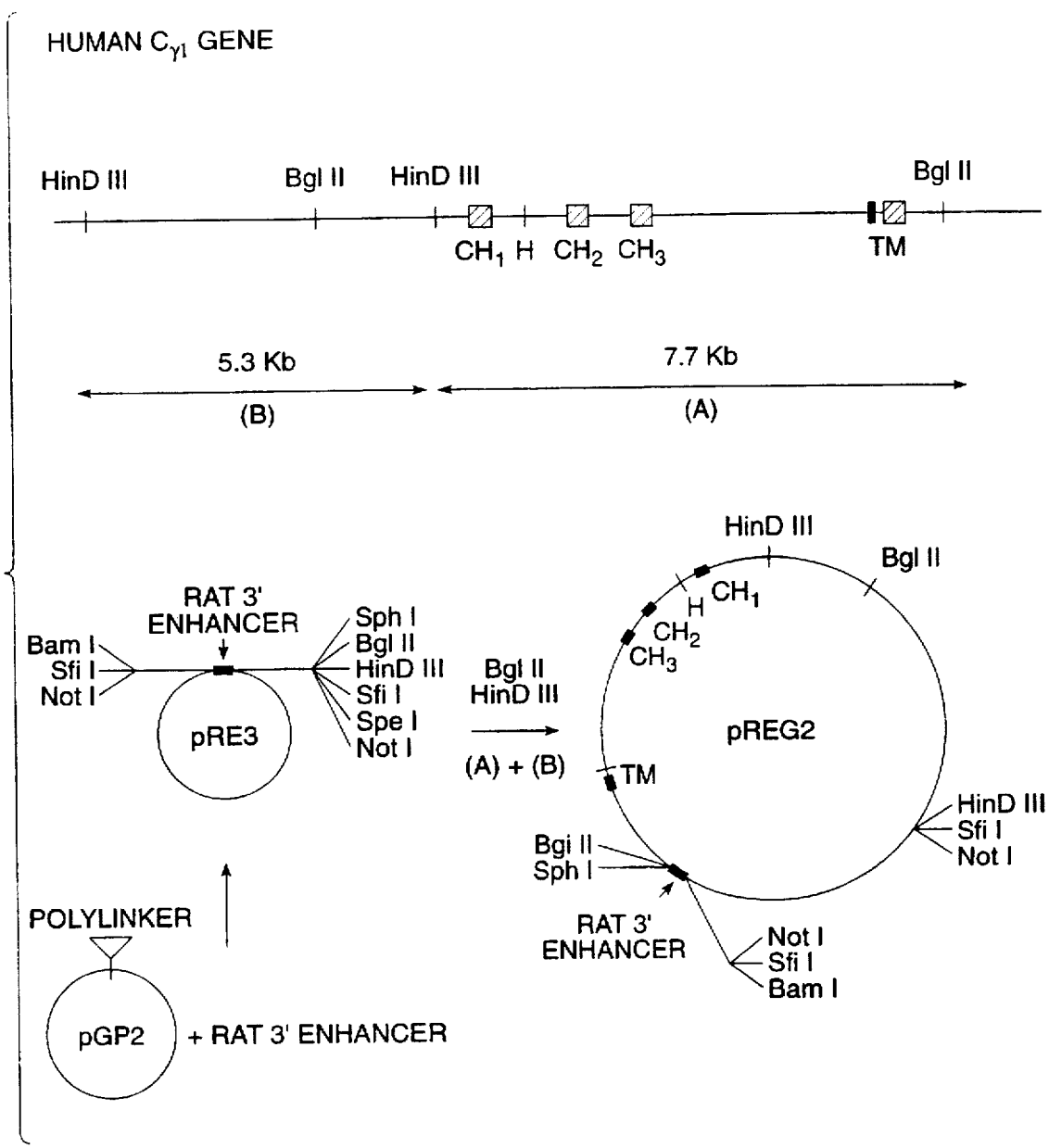
FIG. 11 depicts the human Cγ1 fragments which are inserted into pRE3 (rat enhancer 3') to form pREG2.

A 7.7 kb HindIII to BglII fragment (fragment (a) in FIG. 11) is cloned into HindIII/BglII cut pRE3 to form pREG1. The upstream 5.3 kb HindIII fragment (fragment (b) in FIG. 11) is cloned into HindIII digested pREG1 to form pREG2. Correct orientation is confirmed by BamHI/SpeI digestion.

F. Combining Cγ and Cμ

Figure 10:
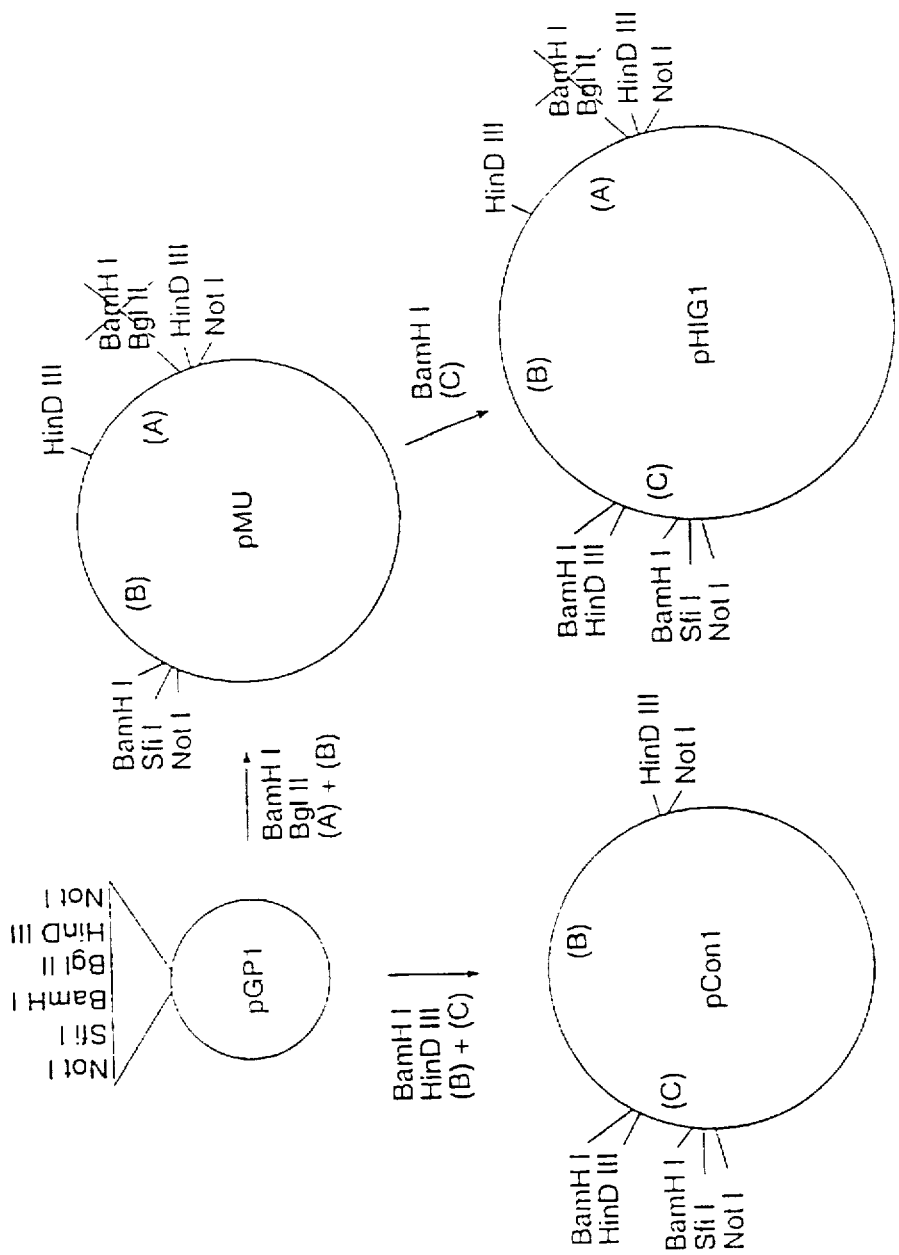
FIG. 10 depicts the construction of pHIG1 and pCON1.
Figure 12:
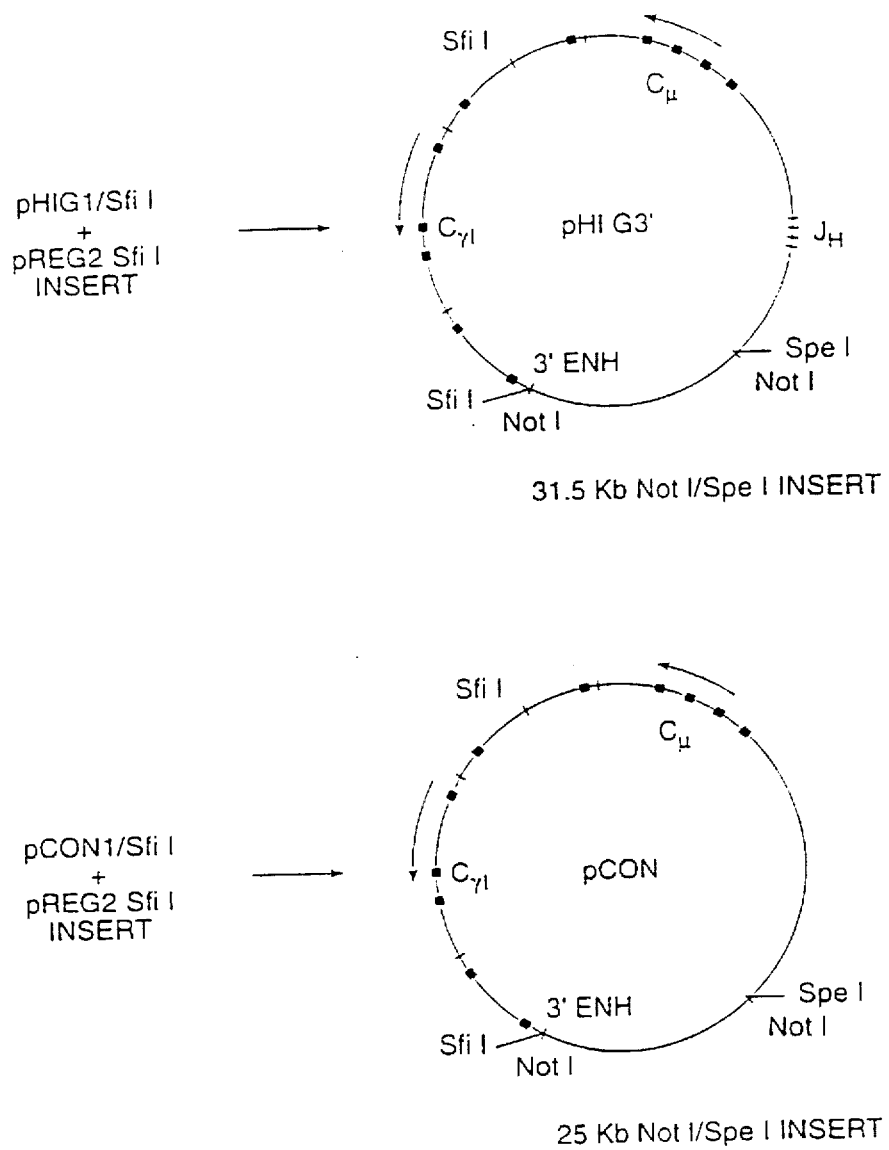
FIG. 12 depicts the construction of pHIG3' and PCON.

The previously described plasmid pHIG1 contains human J segments and the Cμ constant region exons. To provide a transgene containing the Cμ constant region gene segments, pHIG1 was digested with SfiI (FIG. 10). The plasmid pREG2 was also digested with SfiI to produce a 13.5 kb insert containing human Cγ exons and the rat 3I enhancer sequence. These sequences were combined to produce the plasmid pHIG3' (FIG. 12) containing the human J segments, the human Cμ constant region, the human Cγ1 constant region and the rat 3' enhancer contained on a 31.5 kb insert.

A second plasmid encoding human Cμ and human Cγ1 without J segments is constructed by digesting pCON1 with SfiI and combining that with the SfiI fragment containing the human Cγ region and the rat 3' enhancer by digesting pREG2 with SfiI. The resultant plasmid, PCON (FIG. 12) contains a 26 kb NotI/SpeI insert containing human Cμ, human γ1 and the rat 3' enhancer sequence.

G. Cloning of D Segment

Figure 13:
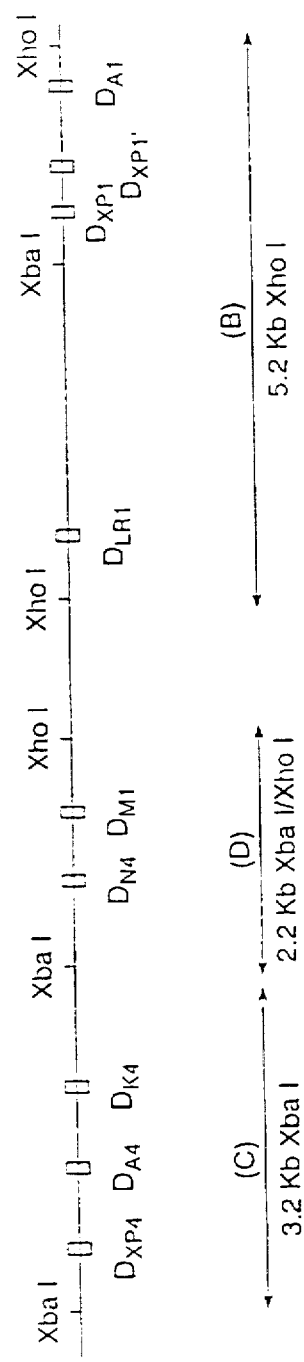
FIG. 13 depicts the fragment containing human D region segments used in construction of the transgenes of the invention.

The strategy for cloning the human D segments is depicted in FIG. 13. Phage clones from the human genomic library containing D segments are identified and isolated using probes specific for diversity region sequences (Ichihara et al., *EMBO J.* 7: 4141–4150 (1988)). The following oligonucleotides are used:

DXP1: 5'- TGG TAT TAC TAT GGT TCG GGG AGT TAT TAT AAC CAC AGT GTC - 3'(SEG ID NO:24)
DXP4: 5'- GCC TGA AAT GGA GCC TCA GGG CAC AGT GGG CAC GGA CAC TGT - 3'(SEG ID NO:25)
DN4: 5'- GCA GGG AGG ACA TGT TTA GGA TCT GAG GCC GCA CCT GAC ACC - 3'(SEG ID NO:26)

A 5.2 kb XhoI fragment (fragment (b) in FIG. 13) containing DLR1, DXP1, DXP'1, and DA1 is isolated from a phage clone identified with oligo DXP1.

A 3.2 kb XbaI fragment (fragment (c) in FIG. 13) containing DXP4, DA4 and DK4 is isolated from a phage clone identified with oligo DXP4.

Fragments (b), (c) and (d) from FIG. 13 are combined and cloned into the XbaI/XhoI site of pGP1 to form pHIG2 which contains a 10.6 kb insert.

This cloning is performed sequentially. First, the 5.2 kb fragment (b) in FIG. 13 and the 2.2 kb fragment (d) of FIG. 13 are treated with calf intestinal alkaline phosphatase and cloned into pGP1 digested with XhoI and XbaI. The resultant clones are screened with the 5.2 and 2.2 kb insert. Half of those clones testing positive with the 5.2 and 2.2 kb inserts have the 5.2 kb insert in the proper orientation as determined by BamHI digestion. The 3.2 kb XbaI fragment from FIG. 13 is then cloned into this intermediate plasmid containing fragments (b) and (d) to form pHIG2. This plasmid contains diversity segments cloned into the polylinker with a unique 5' SfiI site and unique 3' SpeI site. The entire polylinker is flanked by NotI sites.

H. Construction of Heavy Chain Minilocus

The following describes the construction of a human heavy chain mini-locus which contain one or more V segments.

An unrearranged V segment corresponding to that identified as the V segment contained in the hybridoma of Newkirk et al., *J. Clin. Invest.* 81: 1511–1518 (1988), which is incorporated herein by reference, is isolated using the following oligonucleotide:

5'- GAT CCT GGT TTA GTT AAA GAG GAT TTT ATT CAC CCC TGT GTC - 3' (SEQ ID NO:27)

A restriction map of the unrearranged V segment is determined to identify unique restriction sites which provide upon digestion a DNA fragment having a length approximately 2 kb containing the unrearranged V segment together with 5' and 3' flanking sequences. The 5' prime sequences will include promoter and other regulatory sequences whereas the 3' flanking sequence provides recombination sequences necessary for V-DJ joining. This approximately 3.0 kb V segment insert is cloned into the polylinker of pGB2 to form pVH1.

pVH1 is digested with SfiI and the resultant fragment is cloned into the SfiI site of pHIG2 to form a pHIG5'. Since pHIG2 contains D segments only, the resultant pHIG5' plasmid contains a single V segment together with D segments. The size of the insert contained in pHIG5 is 10.6 kb plus the size of the V segment insert.

The insert from pHIG5 is excised by digestion with NotI and SpeI and isolated. pHIG3' which contains J, Cμ and cγ1 segments is digested with SpeI and NotI and the 3' kb fragment containing such sequences and the rat 3' enhancer sequence is isolated. These two fragments are combined and ligated into NotI digested pGP1 to produce pHIG which contains insert encoding a V segment, nine D segments, six functional J segments, Cμ, Cγ and the rat 3' enhancer. The size of this insert is approximately 43 kb plus the size of the V segment insert.

I. Construction of Heavy Chain Minilocus by Homologous Recombination

As indicated in the previous section, the insert of PHIG is approximately 43 to 45 kb when a single V segment is employed. This insert size is at or near the limit of that which may be readily cloned into plasmid vectors. In order to provide for the use of a greater number of V segments, the following describes in vivo homologous recombination of overlapping DNA fragments which upon homologous recombination within a zygote or ES cell form a transgene containing the rat 3' enhancer sequence, the human Cμ, the human Cγ1, human J segments, human D segments and a multiplicity of human V segments.

A 6.3 kb BamHI/HindIII fragment containing human J segments (see fragment (a) in FIG. 9) is cloned into MluI/SpeI digested pHIG5' using the following adapters:

5'GAT CCA AGC AGT 3'(SEQ ID NO:28)
5'CTA GAC TGC TTG 3'(SEQ ID NO:29)
5'CGC GTC GAA CTA 3'(SEQ ID NO:30)
5'AGC TTA GTT CGA 3'(SEQ ID NO:31)

The resultant is plasmid designated pHIG5' (overlap). The insert contained in this plasmid contains human V, D and J segments. When the single V segment from pVH1 is used, the size of this insert is approximately 17 kb plus 2 kb. This insert is isolated and combined with the insert from pHIG3' which contains the human J, Cμ, γ1 and rat 3' enhancer sequences. Both inserts contain human J segments which provide for approximately 6.3 kb of overlap between the two DNA fragments. When coinjected into the mouse zygote, in vivo homologous recombination occurs generating a transgene equivalent to the insert contained in pHIG.

This approach provides for the addition of a multiplicity of V segments into the transgene formed in vivo.

For example, instead of incorporating a single V segment into pHIG5', a multiplicity of V segments contained on (1) isolated genomic DNA, (2) ligated DNA derived from genomic DNA, or (3) DNA encoding a synthetic V segment repertoire is cloned into pHIG2 at the SfiI site to generate pHIG5' $V_N$. The J segments fragment (a) of FIG. 9 is then cloned into pHIG5' $V_N$ and the insert isolated. This insert now contains a multiplicity of V segments and J segments which overlap with the J segments contained on the insert isolated from pHIG3'. When cointroduced into the nucleus of a mouse zygote, homologous recombination occurs to generate in vivo the transgene encoding multiple V segments and multiple J segments, multiple D segments, the Cμ region, the Cγ1 region (all from human) and the rat 3' enhancer sequence.

EXAMPLE 5

Construction of Light Chain Minilocus

A. Construction of pEμ1

The construction of pEμ1 is depicted in FIG. 16. The mouse heavy chain enhancer is isolated on the XbaI to EcoRI 678 bp fragment (Banerji et al., Cell 33: 729–740 (1983)) from phage clones using oligo:
5'GAA TGG GAG TGA GGC TCT CTC ATA CCC TAT TCA GAA CTG ACT 3'(SEQ ID NO:32)

This Eμ fragment is cloned into EcoRV/XbaI digested pGP1 by blunt end filling in EcoRI site. The resultant plasmid is designated pEmul.

B. Construction Of κ Light chain Minilocus

The κ construct contains at least one human $V_κ$ segment, all five human $J_κ$ segments, the human J-$C_κ$ enhancer, the human κ constant region exon, and, ideally, the human 3'κ enhancer (Meyer et al., EMBO J. 8: 1959–1964 (1989)). The κ enhancer in mouse is 9 kb downstream from $C_κ$. However, it is as yet unidentified in the human. In addition, the construct contains a copy of the mouse heavy chain J-Cμ enhancers.

The minilocus is constructed from four component fragments:

(a) A 16 kb SmaI fragment that contains the human $C_κ$ exon and the 3' human enhancer by analogy with the mouse locus;

(b) A 5' adjacent 5 kb SmaI fragment, which contains all five J segments;

(c) The mouse heavy chain intronic enhancer isolated from pEμ1 (this sequence is included to induce expression of the light chain construct as early as possible in B-cell development. Because the heavy chain genes are transcribed earlier than the light chain genes, this heavy chain enhancer is presumably active at an earlier stage than the intronic κ enhancer); and (d) A fragment containing one or more V segments.

The preparation of this construct is as follows. Human placental DNA is digested with SmaI and fractionated on agarose gel by electrophoresis. Similarly, human placental DNA is digested with BamHI and fractionated by electrophoresis. The 16 kb fraction is isolated from the SmaI digested gel and the 11 kb region is similarly isolated from the gel containing DNA digested with BamHI.

The 16 kb SmaI fraction is cloned into Lambda FIX II (Stratagene, La Jolla, Calif.) which has been digested with XhoI, treated with klenow fragment DNA polymerase to fill in the XhoI restriction digest product. Ligation of the 16 kb SmaI fraction destroys the SmaI sites and lases XhoI sites intact.

The 11 kb BamHI fraction is cloned into λ EMBL3 (Stratagene, La Jolla, Calif.) which is digested with BamHI prior to cloning.

Clones from each library were probed with the Cκ specific oligo:
5'GAA CTG TGG CTG CAC CAT CTG TCT TCA TCT TCC CGC CAT CTG 3'(SEQ ID NO:33)

A 16 kb XhoI insert that was subcloned into the XhoI cut pEμ1 so that Cκ is adjacent to the SmaI site. The resultant plasmid was designated pKap1.

Figure 20:
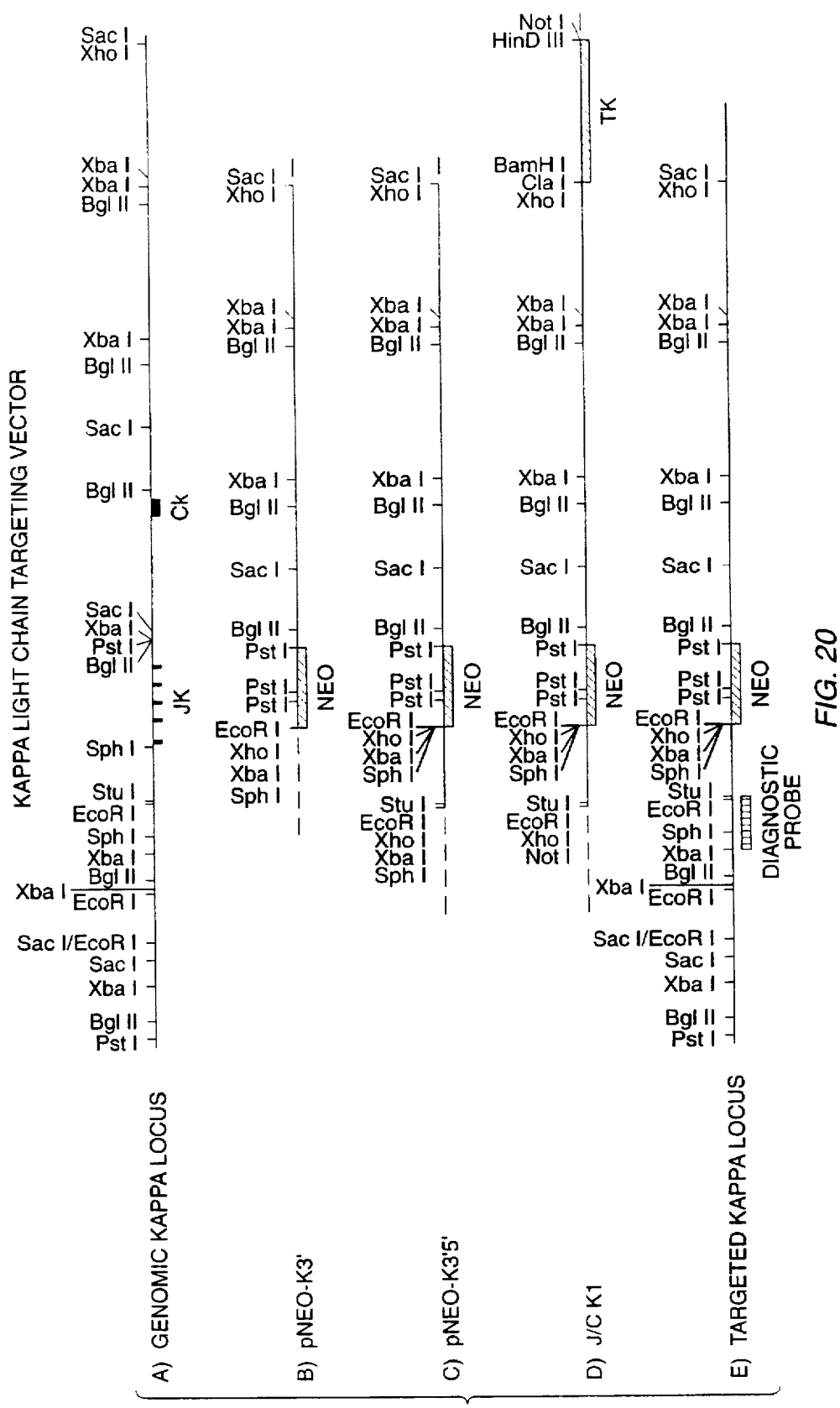
FIGS. 20a through e depict the structure of a kappa light chain targeting vector.

The above Cκ specific oligonucleotide is used to probe the λ EMBL3/BamHI library to identify an 11 kb clone. A 5 kb SmaI fragment (fragment (b) in FIG. 20) is subcloned and subsequently inserted into pKap1 digested with SmaI. Those plasmids containing the correct orientation of J segments, Cκ and the Eμ enhancer are designated pKap2.

One or more Vκ segments are thereafter subcloned into the MluI site of pKap2 to yield the plasmid pKapH which encodes the human Vκ segments, the human Jκ segments, the human Cκ segments and the human Eμ enhancer. This insert is excised by digesting pKapH with NotI and purified by agarose gel electrophoresis. The thus purified insert is microinjected into the pronucleus of a mouse zygote as previously described.

C. Construction of κ Light Chain Minilocus by In Vivo Homologous Recombination

The 11 kb BamHI fragment is cloned into BamHI digested pGP1 such that the 3' end is toward the SfiI site. The resultant plasmid is designated pKAPint. One or more Vκ segments is inserted into the polylinker between the BamHI and SpeI sites in pKAPint to form pKapHV. The insert of pKapHV is excised by digestion with NotI and purified. The insert from pKap2 is excised by digestion with NotI and purified. Each of these fragments contain regions of homology in that the fragment from pKapHV contains a 5 kb sequence of DNA that include the Jκ segments which is substantially homologous to the 5 kb SmaI fragment contained in the insert obtained from pKap2. As such, these inserts are capable of homologously recombining when microinjected into a mouse zygote to form a transgene encoding $V_κ$, $J_κ$ and $C_κ$.

EXAMPLE 6

Isolation of Genomic Clones Corresponding to Rearranged and Expressed Copies of Immunoglobulin κ Light Chain Genes This example describes the cloning of immunoglobulin κ light chain genes from cultured cells that express an immunoglobulin of interest. Such cells may contain multiple alleles of a given immunoglobulin gene. For example, a hybridoma might contain four copies of the κ light chain gene, two copies from the fusion partner cell line and two copies from the original B-cell expressing the immunoglobulin of interest. Of these four copies, only one encodes the immunoglobulin of interest, despite the fact that several of them may be rearranged. The procedure described in this example allows for the selective cloning of the expressed copy of the κ light chain.

A. Double Stranded cDNA

Cells from human hybridoma, or lymphoma, or other cell line that synthesizes either cell surface or secreted or both forms of IgM with a κ light chain are used for the isolation of polyA+ RNA. The RNA is then used for the synthesis of oligo dT primed cDNA using the enzyme reverse transcriptase. The single stranded cDNA is then isolated and G residues are added to the 3' end using the enzyme polynucleotide terminal transferase. The Gtailed single-stranded cDNA is then purified and used as template for second strand synthesis (catalyzed by the enzyme DNA polymerase) using the following oligonucleotide as a primer:

5'- GAG GTA CAC TGA CAT ACT GGC ATG CCC CCC CCC CCC -3'(SEQ ID NO:34)

The double stranded cDNA is isolated and used for determining the nucleotide sequence of the 5' end of the mRNAs encoding the heavy and light chains of the expressed immunoglobulin molecule. Genomic clones of these expressed genes are then isolated. The procedure for cloning the expressed light chain gene is outlined in part B below.

B. Light Chain

The double stranded cDNA described in part A is denatured and used as a template for a third round of DNA synthesis using the following oligonucleotide primer:

5'- GTA CGC CAT ATC AGC TGG ATG AAG TCA TCA GAT GGC GGG AAG ATG AAG ACA GAT GGT GCA -3'(SEQ ID NO:35)

This primer contains sequences specific for the constant portion of the κ light chain message (TCA TCA GAT GGC GGG AAG ATG AAG ACA GAT GGT GCA) (SEQ ID NO:36) as well as unique sequences that can be used as a primer for the PCR amplification of the newly synthesized DNA strand (GTA CGC CAT ATC AGC TGG ATG AAG) (SEQ ID NO:37). The sequence is amplified by PCR using the following two oligonucleotide primers:

5'- GAG GTA CAC TGA CAT ACT GGC ATG -3'(SEG ID NO:38)

5'- GTA CGC CAT ATC AGC TGG ATG AAG -3'(SEQ ID NO:39)

The PCR amplified sequence is then purified by gel electrophoresis and used as template for dideoxy sequencing reactions using the following oligonucleotide as a primer:

5'- GAG GTA CAC TGA CAT ACT GGC ATG -3'(SEQ ID NO:40)

The first 42 nucleotides of sequence will then be used to synthesize a unique probe for isolating the gene from which immunoglobulin message was transcribed. This synthetic 42 nucleotide segment of DNA will be referred to below as o-kappa.

A Southern blot of DNA, isolated from the Ig expressing cell line and digested individually and in pairwise combinations with several different restriction endonucleases including SmaI, is then probed with the 32-P labelled unique oligonucleotide o-kappa. A unique restriction endonuclease site is identified upstream of the rearranged V segment.

DNA from the Ig expressing cell line is then cut with SmaI and second enzyme (or BamHI or KpnI if there is SmaI site inside V segment). Any resulting non-blunted ends are treated with the enzyme T4 DNA polymerase to give blunt ended DNA molecules. Then add restriction site encoding linkers (BamHI, EcoRI or XhoI depending on what site does not exist in fragment) and cut with the corresponding linker enzyme to give DNA fragments with BamHI, EcoRI or XhoI ends. The DNA is then size fractionated by agarose gel electrophoresis, and the fraction including the DNA fragment covering the expressed V segment is cloned into lambda EMBL3 or Lambda FIX (Stratagene, La Jolla, Calif.). V segment containing clones are isolated using the unique probe o-kappa. DNA is isolated from positive clones and subcloned into the polylinker of pKap1. The resulting clone is called PRKL.

EXAMPLE 7

Isolation of Genomic Clones Corresponding to Rearranged Expressed Copies of Immunoglobulin Heavy Chain μ Genes This example describes the cloning of immunoglobulin heavy chain μ genes from cultured cells of expressed and immunoglobulin of interest. The procedure described in this example allows for the selective cloning of the expressed copy of a μ heavy chain gene.

Double-stranded cDNA is prepared and isolated as described herein before. The double-stranded cDNA is denatured and used as a template for a third round of DNA synthesis using the following oligonucleotide primer:

5'- GTA CGC CAT ATC AGC TGG ATG AAG ACA GGA GAC GAG GGG GAA AAG GGT TGG GGC GGA TGC - 3'(SEQ ID NO:41)

This primer contains sequences specific for the constant portion of the μ heavy chain message (ACA GGA GAC GAG GGG GAA AAG GGT TGG GGC GGA TGC) (SEQ ID NO:42) as well as unique sequences that can be used as a primer for the PCR amplification of the newly synthesized DNA strand (GTA CGC CAT ATC AGC TGG ATG AAG) (SEQ ID NO:43). The sequence is amplified by PCR using the following two oligonucleotide primers:

5'- GAG GTA CAC TGA CAT ACT GGC ATG - 3'(SEQ ID NO:44)

5'- GTA CTC CAT ATC AGC TGG ATG AAG - 3'(SEQ ID NO:45)

The PCR amplified sequence is then purified by gel electrophoresis and used as template for dideoxy sequencing reactions using the following oligonucleotide as a primer:

5'- GAG GTA CAC TGA CAT ACT GGC ATG - 3'(SEQ ID NO:46)

The first 42 nucleotides of sequence are then used to synthesize a unique probe for isolating the gene from which immunoglobulin message was transcribed. This synthetic 42 nucleotide segment of DNA will be referred to below as o-mu.

A Southern blot of DNA, isolated from the Ig expressing cell line and digested individually and in pairwise combinations with several different restriction endonucleases including MluI (MluI is a rare cutting enzyme that cleaves between the J segment and mu CH1), is then probed with the 32-P labelled unique oligonucleotide o-mu. A unique restriction endonuclease site is identified upstream of the rearranged V segment.

DNA from the Ig expressing cell line is then cut with MluI and second enzyme. MluI or SpeI adapter linkers are then ligated onto the ends and cut to convert the upstream site to MluI or SpeI. The DNA is then size fractionated by agarose gel electrophoresis, and the fraction including the DNA fragment covering the expressed V segment is cloned directly into the plasmid pGPI. V segment containing clones are isolated using the unique probe o-mu, and the insert is subcloned into MluI or MluI/SpeI cut plasmid pCON2. The resulting plasmid is called PRMGH.

EXAMPLE 8

Construction of Human κ Miniloci Transgenes Light Chain Minilocus A human genomic DNA phage library was screened with kappa light chain specific oligonucleotide probes and isolated clones spanning the $J_\kappa$-C region. A 5.7 kb ClaI/XhoI fragment containing JK1 together with a 13 kb XhoI fragment containing $J_\kappa 2$–5 and $C_\kappa$ into pGP1d was cloned and used to create the plasmid pKcor. This plasmid contains $J_\kappa 1$–5, the kappa intronic enhancer and $C_\kappa$ together with 4.5 kb of 5' and 9 kb of 3' flanking sequences. It also has a unique 5' XhoI site for cloning $V_\kappa$ segments and a unique 3' SalI site for inserting additional cis-acting regulatory sequences.

V kappa genes

A human genomic DNA phage library was screened with $V_\kappa$ light chain specific oligonucleotide probes and isolated clones containing human $V_\kappa$ segments. Functional V segments were identified by DNA sequence analysis. These clones contain TATA boxes, open reading frames encoding leader and variable peptides (including 2 cysteine residues), splice sequences, and recombination heptamer-12 bp spacer-nonamer sequences. Three of the clones were mapped and sequenced. Two of the clones, 65.5 and 65.8 appear to be functional, they contain TATA boxes, open reading frames encoding leader and variable peptides (including 2 cysteine residues), splice sequences, and recombination heptamer-12 bp spacer-nonamer sequences. The third clone, 65.4, appears to encode a $V_\kappa I$ pseudogene as it contains a non-canonical recombination heptamer.

One of the functional clones, Vk 65-8, which encodes a VkIII family gene, was used to build a light chain minilocus construct.

pKC1

Figure 32:
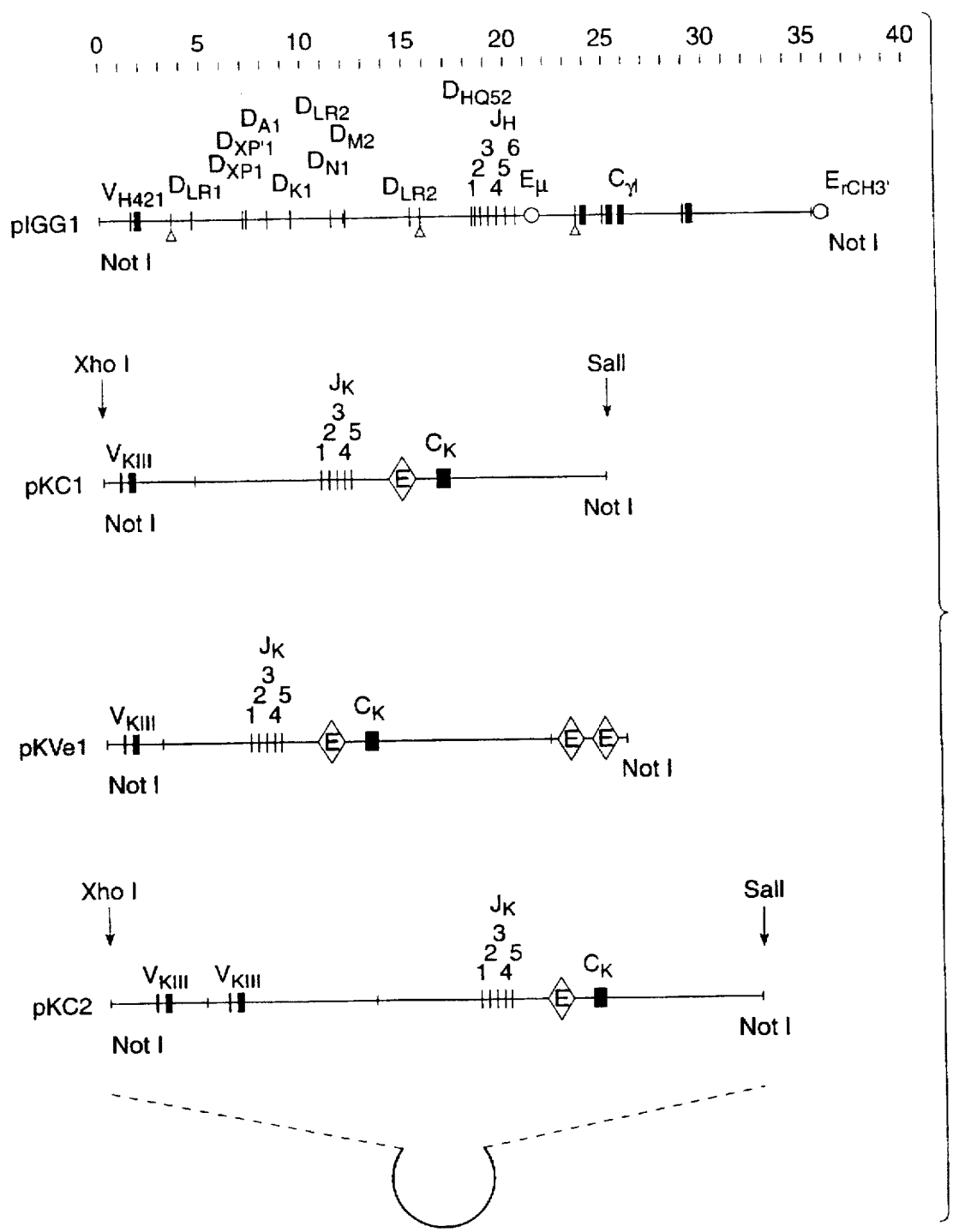
FIG. 32 is a schematic representation of the heavy chain minilocus construct pIGG1 and the κ light chain minilocus construct pKC1, pKVe1, and pKC2.

The kappa light chain minilocus transgene pKC1 (FIG. 32) was generated by inserting a 7.5 kb XhoI/SalI fragment containing $V_\kappa 65.8$ into the 5' XhoI site of pKcor. The transgene insert was isolated by digestion with NotI prior to injection.

The purified insert was microinjected into the pronuclei of fertilized (C57BL/6 × CBA)F2 mouse embryos and transferred the surviving embryos into pseudopregnant females as described by Hogan et al. (in Methods of Manipulating the Mouse Embryo, 1986, Cold Spring Harbor Laboratory, N.Y.). Mice that developed from injected embryos were analyzed for the presence of transgene sequences by Southern blot analysis of tail DNA. Transgene copy number was estimated by band intensity relative to control standards containing known quantities of cloned DNA. Serum was isolated from these animals and assayed for the presence of transgene encoded human Ig kappa protein by ELISA as described by Harlow and Lane (in Antibodies: A Laboratory Manual, 1988, Cold Spring Harbor Laboratory, N.Y.). Microtiter plate wells were coated with mouse monoclonal antibodies specific for human Ig kappa (clone 6E1, #0173, AMAC, Inc., Westbrook, Me.), human IgM (Clone AF6, #0285, AMAC, Inc., Westbrook, Me.) and human IgG1 (clone JL512, #0280, AMAC, Inc., Westbrook, Me.). Serum samples were serially diluted into the wells and the presence of specific immunoglobulins detected with affinity isolated alkaline phosphatase conjugated goat anti-human Ig (polyvalent) that had been pre-adsorbed to minimize cross-reactivity with mouse immunoglobulins.

Figure 36:
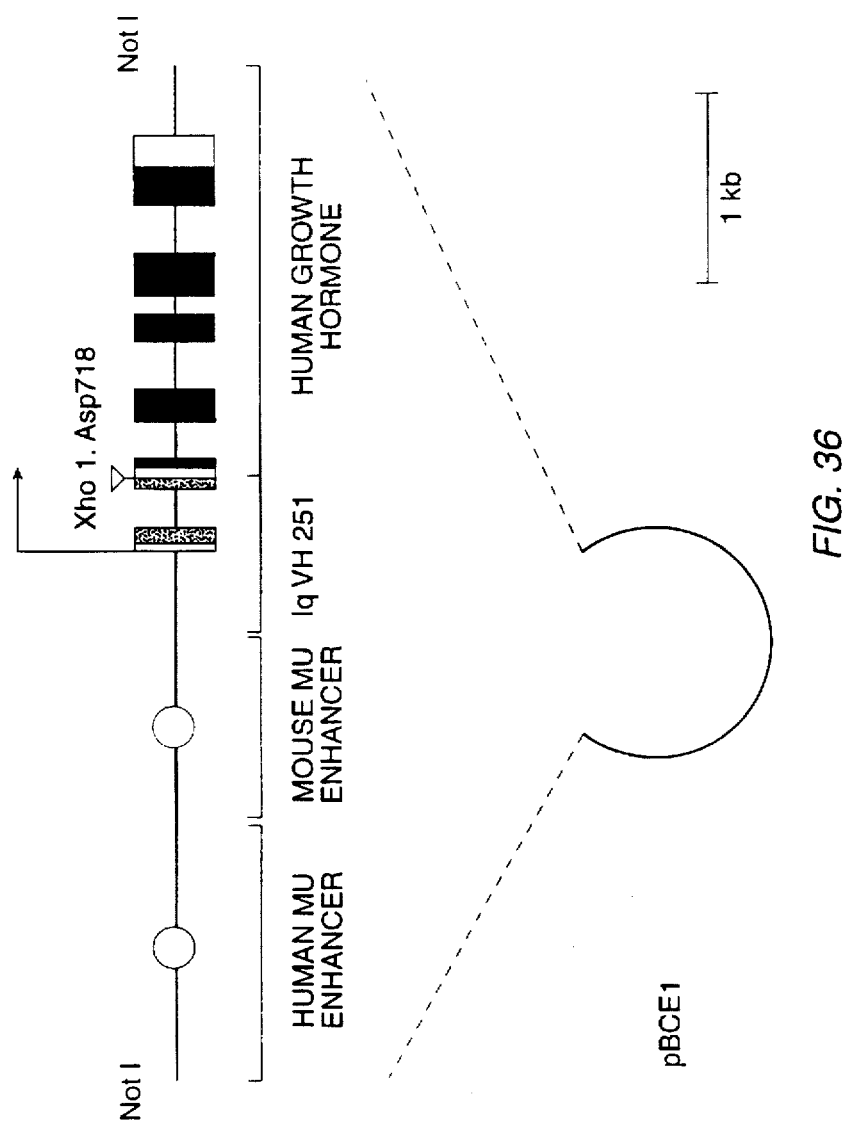
FIG. 36 is a schematic representation of plasmid pBCE1.

FIG. 36 shows the results of an ELISA assay of serum from 8 mice (I.D. #676, 674, 673, 670, 666, 665, 664, and 496). The first seven of these mice developed from embryos that were injected with the pKC1 transgene insert and the eighth mouse is derived from a mouse generated by microinjection of the pHC1 transgene (described previously). Two of the seven mice from KC1 injected embryos (I.D.#'s 666 and 664) did not contain the transgene insert as assayed by DAN Southern blot analysis, and five of the mice (I.D.#'s 676, 674, 673, 670, and 665) contained the transgene. All but one of the KC1 transgene positive animals express detectable levels of human Ig kappa protein, and the single non-expressing animal appears to be a genetic mosaic on the basis of DNA Southern blot analysis. The pHC1 positive transgenic mouse expresses human IgM and IgG1 but not Ig kappa, demonstrating the specificity of the reagents used in the assay.

pKC2

The kappa light chain minilocus transgene pKC2 was generated by inserting an 8 kb XhoI/SalI fragment containing $V_\kappa 65.5$ into the 5' XhoI site of pKC1. The resulting transgene insert, which contains two $V_\kappa$ segments, was isolated prior to microinjection by digestion with NotI.

pKVe2

This construct is identical to pKC1 except that it includes 1.2 kb of additional sequence 5' of $J_\kappa$ and is missing 4.5 kb of sequence 3' of $V_\kappa 65.8$. In additional it contains a 0.9 kb XbaI fragment containing the mouse heavy chain J-m intronic enhancer (Banerji et al., *Cell* 33: 729–740 (1983)) together with a 1.4 kb MluI HindIII fragment containing the human heavy chain J-m intronic enhancer (Hayday et al., *Nature* 307: 334–340 (1984)) inserted downstream. This construct tests the feasibility of initiating early rearrangement of the light chain minilocus to effect allelic and isotypic exclusion. Analogous constructs can be generated with different enhancers, i.e., the mouse or rat 3' kappa or heavy chain enhancer (Meyer and Neuberger, *EMBO J.* 8: 1959–1964 (1989); Petterson et al. *Nature* 344: 165–168 (1990), which are incorporated herein by reference).

Rearranged Light Chain Transgenes

Figure 33:
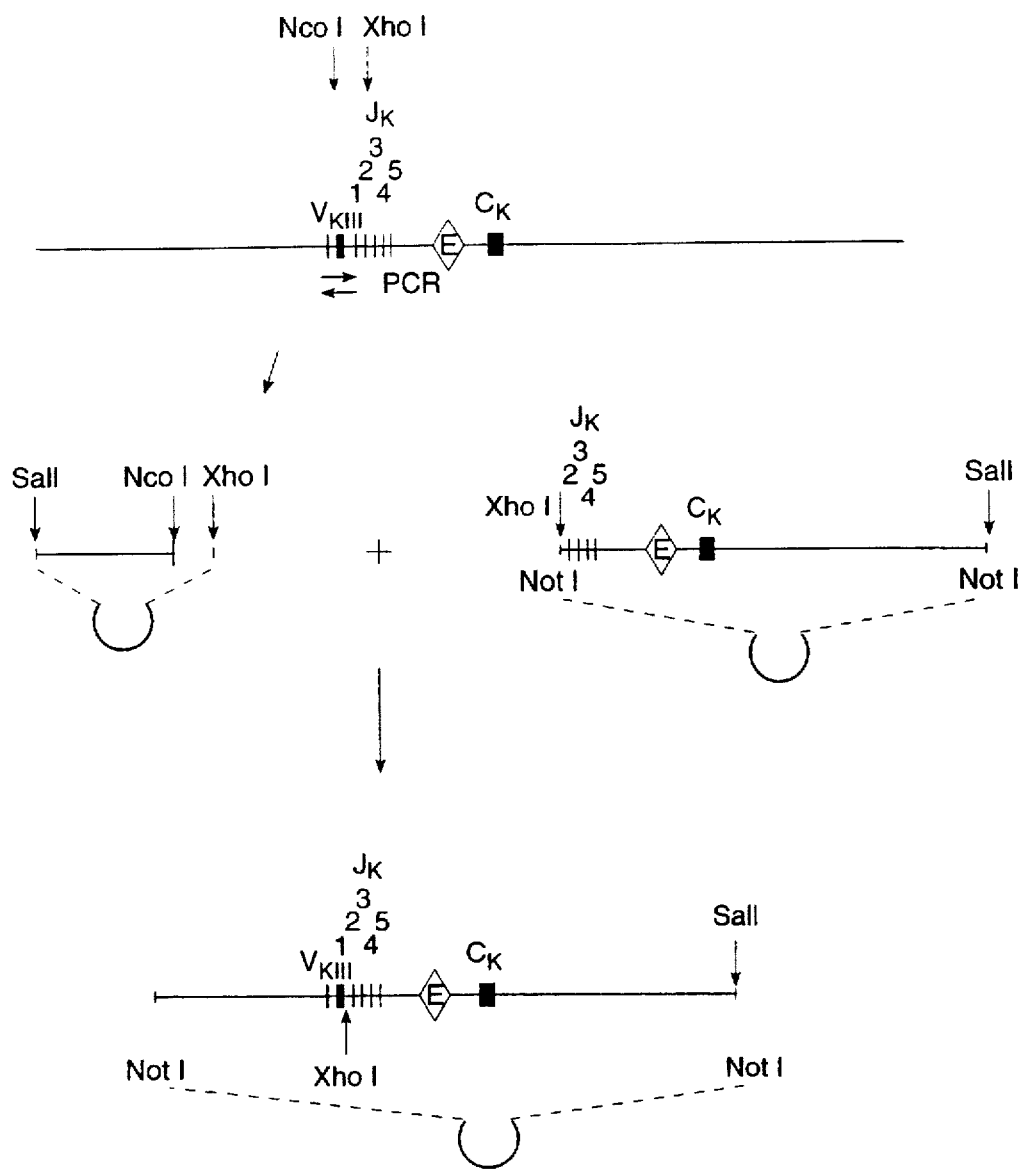
FIG. 33 depicts a scheme to reconstruct functionally rearranged light chain genes.

A kappa light chain expression cassette was designed to reconstruct functionally rearranged light chain genes that have been amplified by PCR from human B-cell DNA. The scheme is outlined in FIG. 33. PCR amplified light chain genes are cloned into the vector pK5nx that includes 3.7 kb of 5' flanking sequences isolated from the kappa light chain gene 65.5. The VJ segment fused to the 5' transcriptional sequences are then cloned into the unique XhoI site of the vector pK31s that includes $J_\kappa 2$–4, the $J_\kappa$ intronic enhancer, $C_\kappa$, and 9 kb of downstream sequences. The resulting plasmid contains a reconstructed functionally rearranged kappa light chain transgene that can be excised with NotI for microinjection into embryos. The plasmids also contain unique SalI sites at the 3' end for the insertion of additional cis-acting regulatory sequences.

Two synthetic oligonucleotides (o-130, o-131) were used to amplify rearranged kappa light chain genes from human spleen genomic DNA. Oligonucleotide o-131 (gga ccc aga (g,c)gg aac cat gga a(g,a)(g,a,t,c)) is complementary to the 5' region of $V_\kappa III$ family light chain genes and overlaps the first ATC of the leader sequence. Oligonucleotide o-130 (gtg aa tca att ctc gag ttt gac tac aga c) is complementary to a sequence approximately 150 bp 3' of $J_\kappa 1$ and includes an XhoI site. These two oligonucleotides amplify a 0.7 kb DNA fragment from human spleen DNA corresponding to rearranged $V_\kappa III$ genes joined to $J_\kappa 1$ segments. The PCR amplified DNA was digested with NcoI and XhoI and cloned individual PCR products into the plasmid pNN03. The DNA sequence of 5 clones was determined and identified two with functional VJ joints (open reading frames). Additional functionally rearranged light chain clones are collected. The functionally rearranged clones can be individually cloned into light chain expression cassette described above (FIG. 33). Transgenic mice generated with the rearranged light chain constructs can be bred with heavy chain minilocus transgenics to produce a strain of mice that express a spectrum of fully human antibodies in which all of the diversity of the primary repertoire is contributed by the heavy chain. One source of light chain diversity can be from somatic mutation. Because not all light chains will be equivalent with respect to their ability to combine with a variety of different heavy chains, different strains of mice, each containing different light chain constructs can be generated and tested. The advantage of this scheme, as opposed to the use of unrearranged light chain miniloci, is the increased light chain allelic and isotypic exclusion that comes from having the light chain ready to pair with a heavy chain as soon as heavy chain VDJ joining occurs. This combination can result in an increased frequency of B-cells expressing fully human antibodies, and thus it can facilitate the isolation of human Ig expressing hybridomas.

NotI inserts of plasmids pIGM1, pHC1, pIGG1, pKC1, and pKC2 were isolated away from vector sequences by agarose gel electrophoresis. The purified inserts were microinjected into the pronuclei of fertilized (C57BL/6 x CBA)F2 mouse embryos and transferred the surviving embryos into pseudopregnant females as described by Hogan et al. (Hogan et al., *Methods of Manipulating the Mouse Embryo*, Cold spring Harbor Laboratory, N.Y. (1986)).

EXAMPLE 9

Inactivation of the Mouse Kappa Light Chain Gene by Homologous Recombination

This example describes the inactivation of the mouse endogenous kappa locus by homologous recombination in embryonic stem (ES) cells followed by introduction of the mutated gene into the mouse germ line by injection of targeted ES cells bearing an inactivated kappa allele into early mouse embryos (blastocysts).

The strategy is to delete $J_K$ and $C_K$ by homologous recombination with a vector containing DNA sequences homologous to the mouse kappa locus in which a 4.5 kb segment of the locus, spanning the $J_K$ gene and $C_K$ segments, is deleted and replaced by the selectable marker neo.

Construction of the kappa targeting vector

The plasmid pGEM7 (KJ1) contains the neomycin resistance gene (neo), used for drug selection of transfected ES cells, under the transcriptional control of the mouse phosphoglycerate kinase (pgk) promoter (XbaI/TaqI fragment; Adra et al., *Gene* 60: 65–74 (1987)) in the cloning vector pGEM7Zf(+). The plasmid also includes a heterologous polyadenylation site for the neo gene, derived from the 3' region of the mouse pgk gene (PvuII/HindIII fragment; Boer et al., *Biochemical Genetics*, 28: 299–308 (1990)). This plasmid was used as the starting point for construction of the kappa targeting vector. The first step was to insert sequences homologous to the kappa locus 3' of the neo expression cassette.

Mouse kappa chain sequences (FIG. 20a) were isolated from a genomic phage library derived from liver DNA using oligonucleotide probes specific for the Cκ locus:

5'- GGC TGA TGC TGC ACC AAC TGT ATC CAT CTT CCC ACC ATC CAG -3'(SEQ ID NO:47)

and for the JK5 gene segment:

5'- CTC ACG TTC GGT GCT GGG ACC AAG CTG GAG CTG AAA CGT AAG -3'(SEQ ID NO: 48)

An 8 kb BglII/SacI fragment extending 3' of the mouse $C_K$ segment was isolated from a positive phage clone in two pieces, as a 1.2 kb BglII/SacI fragment and a 6.8 kb SacI fragment, and subcloned into BglII/SacI digested pGEM7 (KJ1) to generate the plasmid pNEO-K3' (FIG. 20b).

A 1.2 kb EcoRI/SphI fragment extending 5' of the $J_K$ region was also isolated from a positive phage clone. An SphI/XbaI/BglII/EcoRI adaptor was ligated to the SphI site of this fragment, and the resulting EcoRI fragment was ligated into EcoRI digested pNEO-K3', in the same 5' to 3' orientation as the neo gene and the downstream 3' kappa sequences, to generate pNEO-K5'3' (FIG. 20c).

The Herpes Simplex Virus (HSV) thymidine kinase (TK) gene was then included in the construct in order to allow for enrichment of ES clones bearing homologous recombinants, as described by Mansour et al., *Nature* 336: 348–352 (1988), which is incorporated herein by reference. The HSV TK cassette was obtained from the plasmid pGEM7 (TK), which contains the structural sequences for the HSV TK gene bracketed by the mouse pgk promoter and polyadenylation sequences as described above for pGEM7 (KJ1). The EcoRI site of pGEM7 (TK) was modified to a BamHI site and the TK cassette was then excised as a BamHI/HindIII fragment and subcloned into pGP1b to generate pGP1b-TK. This plasmid was linearized at the XhoI site and the XhoI fragment from pNEO-K5'3', containing the neo gene flanked by genomic sequences from 5' of JK and 3' of CK, was inserted into pGP1b-TK to generate the targeting vector J/C KI (FIG. 20d). The putative structure of the genomic kappa locus following homologous recombination with J/C K1 is shown in FIG. 20e.

Generation and analysis of ES cells with targeted inactivation of a kappa allele The ES cells used were the AB-1 line grown on mitotically inactive SNL76/7 cell feeder layers (McMahon and Bradley, *Cell* 62: 1073–1085 (1990)) essentially as described (Robertson, E. J. (1987) in *Teratocarcinomas and Embryonic Stem Cells: A Practical Approach*. E. J. Robertson, ed. (Oxford: IRL Press), p. 71–112). Other suitable ES lines include, but are not limited to, the E14 line (Hooper et al. (1987) *Nature* 326: 292–295), the D3 line (Doetschman et al. (1985) *J. Embryol. Exp. Morph.* 87: 27–45), and the CCE line (Robertson et al. (1986) *Nature* 323: 445–448). The success of generating a mouse line from ES cells bearing a specific targeted mutation depends on the pluripotence of the ES cells (i.e., their ability, once injected into a host blastocyst, to participate in embryogenesis and contribute to the germ cells of the resulting animal).

The pluripotence of any given ES cell line can vary with time in culture and the care with which it has been handled. The only definitive assay for pluripotence is to determine whether the specific population of ES cells to be used for targeting can give rise to chimeras capable of germline transmission of the ES genome. For this reason, prior to gene targeting, a portion of the parental population of AB-1 cells is injected into C57B1/6J blastocysts to ascertain whether the cells are capable of generating chimeric mice with extensive ES cell contribution and whether the majority of these chimeras can transmit the ES genome to progeny.

The kappa chain inactivation vector J/C K1 was digested with NotI and electroporated into AB-1 cells by the methods described (Hasty et al., *Nature*, 350: 243–246 (1991)).

Electroporated cells were plated onto 100 mm dishes at a density of 1–2×10⁶ cells/dish. After 24 hours, G418 (200 g/ml of active component) and FIAU (0.5 µM) were added to the medium, and drug-resistant clones were allowed to develop over 10–11 days. Clones were picked, trypsinized, divided into two portions, and further expanded. Half of the cells derived from each clone were then frozen and the other half analyzed for homologous recombination between vector and target sequences.

DNA analysis was carried out by Southern blot hybridization. DNA was isolated from the clones as described (Laird et al., *Nucl. Acids Res.* 19: 4293 (1991)) digested with XbaI and probed with the 800 bp EcoRI/XbaI fragment indicated in FIG. 20e as probe A. This probe detects a 3.7 kb XbaI fragment in the wild type locus, and a diagnostic 1.8 kb band in a locus which has homologously recombined with the targeting vector (see FIG. 20a and e). Of 901 G418 and FIAU resistant clones screened by Southern blot analysis, 7 displayed the 1.8 kb XbaI band indicative of a homologous recombination into one of the kappa genes. These 7 clones were further digested with the enzymes BglII, SacI, and PstI to verify that the vector integrated homologously into one of the kappa genes. When probed with the diagnostic 800 bp EcoRI/XbaI fragment (probe A), BglII, SacI, and PstI digests of wild type DNA produce fragments of 4.1, 5.4, and 7 kb, respectively, whereas the presence of a targeted kappa allele would be indicated by fragments of 2.4, 7.5, and 5.7 kb, respectively (see FIG. 20a and e). All 7 positive clones detected by the XbaI digest showed the expected BglII, SacI, and PstI restriction fragments diagnostic of a homologous recombination at the kappa light chain. In addition, Southern blot analysis of an NsiI digest of the targeted clones using a neo specific probe (probe B, FIG. 20e) generated only the predicted fragment of 4.2 kb, demonstrating that the clones each contained only a single copy of the targeting vector.

Generation of mice bearing the inactivated kappa chain

Five of the targeted ES clones described in the previous section were thawed and injected into C57B1/6J blastocysts as described (Bradley, A. (1987) in *Teratocarcinomas and Embryonic Stem Cells: A Practical Approach*. E. J. Robertson, ed. (Oxford: IRL Press), p. 113–151) and transferred into the uteri of pseudopregnant females to generate chimeric mice resulting from a mixture of cells derived from the input ES cells and the host blastocyst. The extent of ES cell contribution to the chimeras can be visually estimated by the amount of agouti coat coloration, derived from the ES cell line, on the black C57B1/6J background. Approximately half of the offspring resulting from blastocyst injection of the targeted clones were chimeric (i.e., showed agouti as well as black pigmentation) and of these, the majority showed extensive (70 percent or greater) ES cell contribution to coat pigmentation. The AB1 ES cells are an XY cell line and a majority of these high percentage chimeras were male due to sex conversion of female embryos colonized by male ES cells. Male chimeras derived from 4 of the 5 targeted clones were bred with C57BL/6J females and the offspring monitored for the presence of the dominant agouti coat color indicative of germline transmission of the ES genome. Chimeras from two of these clones consistently generated agouti offspring. Since only one copy of the kappa locus was targeted in the injected ES clones, each agouti pup had a 50 percent chance of inheriting the mutated locus. Screening for the targeted gene was carried out by Southern blot analysis of Bgl II-digested DNA from tail biopsies, using the probe utilized in identifying targeted ES clones (probe A, FIG. 20e). As expected, approximately 50 percent of the agouti offspring showed a hybridizing Bgl II band of 2.4 kb in addition to the wild-type band of 4.1 kb, demonstrating the germline transmission of the targeted kappa locus.

In order to generate mice homozygous for the mutation, heterozygotes were bred together and the kappa genotype of the offspring determined as described above. As expected, three genotypes were derived from the heterozygote matings: wild-type mice bearing two copies of a normal kappa locus, heterozygotes carrying one targeted copy of the kappa gene and one NT kappa gene, and mice homozygous for the kappa mutation. The deletion of kappa sequences from these latter mice was verified by hybridization of the Southern blots with a probe specific for $J_K$ (probe C, FIG. 20a). Whereas hybridization of the $J_K$ probe was observed to DNA samples from heterozygous and wild-type siblings, no hybridizing signal was present in the homozygotes, attesting to the generation of a novel mouse strain in which both copies of the kappa locus have been inactivated by deletion as a result of targeted mutation.

EXAMPLE 10

Inactivation of the Mouse Heavy Chain Gene by Homologous Recombination

This example describes the inactivation of the endogenous murine immunoglobulin heavy chain locus by homologous recombination in embryonic stem (ES) cells. The strategy is to delete the endogenous heavy chain J segments by homologous recombination with a vector containing heavy chain sequences from which the $J_H$ region has been deleted and replaced by the gene for the selectable marker neo.

Construction of a heavy chain targeting vector

Mouse heavy chain sequences containing the $J_H$ region (FIG. 21a) were isolated from a genomic phage library derived from the D3 ES cell line (Gossler et al., *Proc. Natl. Acad. Sci. U.S.A.* 83: 9065–9069 (1986)) using a JH⁴ specific oligonucleotide probe:

5'- ACT ATG CTA TGG ACT ACT GGG GTC AAG GAA CCT CAG TCA CCG-3'(SEQ ID NO:49)

A 3.5 kb genomic SacI/StuI fragment, spanning the $J_H$ region, was isolated from a positive phage clone and subcloned into SacI/SmaI digested pUC18. The resulting plasmid was designated pUC18 $J_H$. The neomycin resistance gene (neo), used for drug selection of transfected ES cells, was derived from a repaired version of the plasmid pGEM7 (KJ1). A report in the literature (Yenofsky et al. (1990) *Proc. Natl. Acad. Sci.* (U.S.A.) 87: 3435–3439) documents a point mutation the neo coding sequences of several commonly used expression vectors, including the construct pMC1neo (Thomas and Cappechi (1987) *Cell* 51: 503–512) which served as the source of the neo gene used in pGEM7 (KJ1). This mutation reduces the activity of the neo gene product and was repaired by replacing a restriction fragment encompassing the mutation with the corresponding sequence from a wild-type neo clone. The HindIII site in the prepared pGEM7 (KJ1) was converted to a SalI site by addition of a synthetic adaptor, and the neo expression cassette excised by digestion with XbaI/SalI. The ends of the neo fragment were then blunted by treatment with the Klenow form of DNA poli, and the neo fragment was subcloned into the NaeI site of pUC18 $J_H$, generating the plasmid pUC18 $J_H$-neo (FIG. 21b).

Further construction of the targeting vector was carried out in a derivative of the plasmid pGP1b. pGP1b was digested with the restriction enzyme NotI and ligated with the following oligonucleotide as an adaptor:

5'- GGC CGC TCG ACG ATA GCC TCG AGG CTA TAA
ATC TAG AAG AAT TCC AGC AAA GCT TTG GC
-3'(SEQ ID NO:50)

The resulting plasmid, called pGMT, was used to build the mouse immunoglobulin heavy chain targeting construct.

The Herpes Simplex Virus (HSV) thymidine kinase (TK) gene was included in the construct in order to allow for enrichment of ES clones bearing homologous recombinants, as described by Mansour et al. (*Nature* 336, 348–352 (1988)). The HSV TK gene was obtained from the plasmid pGEM7 (TK) by digestion with EcoRI and HindIII. The TK DNA fragment was subcloned between the EcoRI and HindIII sites of pGMT, creating the plasmid PGMT-TK (FIG. 21c).

To provide an extensive region of homology to the target sequence, a 5.9 kb genomic XbaI/XhoI fragment, situated 5' of the $J_H$ region, was derived from a positive genomic phage clone by limit digestion of the DNA with XhoI, and partial digestion with XbaI. As noted in FIG. 21a, this XbaI site is not present in genomic DNA, but is rather derived from phage sequences immediately flanking the cloned genomic heavy chain insert in the positive phage clone. The fragment was subcloned into XbaI/XhoI digested pGMT-TK, to generate the plasmid pGMT-TK-$J_H$5' (FIG. 21d).

The final step in the construction involved the excision from pUC18 $J_H$-neo of the 2.8 kb EcoRI fragment which contained the neo gene and flanking genomic sequences 3' of $J_H$. This fragment was blunted by Klenow polymerase and subcloned into the similarly blunted XhoI site of pGMT-TK-$J_H$5'. The resulting construct, $J_H$KO1 (FIG. 21e), contains 6.9 kb of genomic sequences flanking the $J_H$ locus, with a 2.3 kb deletion spanning the $J_H$ region into which has been inserted the neo gene. FIG. 21f shows the structure of an endogenous heavy chain gene after homologous recombination with the targeting construct.

EXAMPLE 11

Generation and analysis of targeted ES cells

AB-1 ES cells (McMahon and Bradley, *Cell* 62: 1073–1085 (1990)) were grown on mitotically inactive SNL76/7 cell feeder layers essentially as described (Robertson, E. J. (1987) *Teratocarcinomas and Embryonic Stem Cells: A Practical Approach*, E. J. Robertson, ed. (Oxford: IRL Press), pp. 71–112). As described in the previous example, prior to electroporation of ES cells with the targeting construct $J_H$KO1, the pluripotency of the ES cells was determined by generation of AB-1 derived chimeras which were shown capable of germline transmission of the ES genome.

The heavy chain inactivation vector $J_H$KO1 was digested with NotI and electroporated into AB-1 cells by the methods described (Hasty et al., *Nature* 350: 243–246 (1991)). Electroporated cells were plated into 100 mm dishes at a density of 1–2×10$^6$ cells/dish. After 24 hours, G418 (200 mg/ml of active component) and FIAU (0.5 mM) were added to the medium, and drug-resistant clones were allowed to develop over 8–10 days. Clones were picked, trypsinized, divided into two portions, and further expanded. Half of the cells derived from each clone were then frozen and the other half analyzed for homologous recombination between vector and target sequences.

DNA analysis was carried out by Southern blot hybridization. DNA was isolated from the clones as described (Laird et al. (1991) *Nucleic Acids Res.* 19: 4293), digested with StuI and probed with the 500 bp EcoRI/StuI fragment designated as probe A in FIG. 21f. This probe detects a StuI fragment of 4.7 kb in the wild-type locus, whereas a 3 kb band is diagnostic of homologous recombination of endogenous sequences with the targeting vector (see FIG. 21a and f). Of 525 G418 and FIAU doubly-resistant clones screened by Southern blot hybridization, 12 were found to contain the 3 kb fragment diagnostic of recombination with the targeting vector. That these clones represent the expected targeted events at the $J_H$ locus (as shown in FIG. 21f) was confirmed by further digestion with HindIII, SpeI and HpaI. Hybridization of probe A (see FIG. 21f) to Southern blots of HindIII, SpeI, and HpaI digested DNA produces bands of 2.3 kb, >10 kb, and >10 kb, respectively, for the wild-type locus (see FIG. 21a), whereas bands of 5.3 kb, 3.8 kb, and 1.9 kb, respectively, are expected for the targeted heavy chain locus (see FIG. 21f). All 12 positive clones detected by the StuI digest showed the predicted HindIII, SpeI, and HpaI bands diagnostic of a targeted $J_H$ gene. In addition, Southern blot analysis of a StuI digest of all 12 clones using a neo-specific probe (probe B, FIG. 21f) generated only the predicted fragment of 3 kb, demonstrating that the clones each contained only a single copy of the targeting vector.

Generation of mice carrying the $J_H$ deletion

Three of the targeted ES clones described in the previous section were thawed and injected into C57BL/6J blastocysts as described (Bradley, A. (1987) in *Teratocarcinomas and Embryonic Stem Cells: A Practical Approach*, E. J. Robertson, ed. (Oxford: IRL Press), p.113–151) and transferred into the uteri of pseudopregnant females. The extent of ES cell contribution to the chimera was visually estimated from the amount of agouti coat coloration, derived from the ES cell line, on the black C57BL/6J background. Half of the offspring resulting from blastocyst injection of two of the targeted clones were chimeric (i.e., showed agouti as well as black pigmentation); the third targeted clone did not generate any chimeric animals. The majority of the chimeras showed significant (approximately 50 percent or greater) ES cell contribution to coat pigmentation. Since the AB-1 ES cells are an XY cell line, most of the chimeras were male, due to sex conversion of female embryos colonized by male ES cells. Males chimeras were bred with C57BL/6J females and the offspring monitored for the presence of the dominant agouti coat color indicative of germline transmission of the ES genome. Chimeras from both of the clones consistently generated agouti offspring. Since only one copy of the heavy chain locus was targeted in the injected ES clones, each agouti pup had a 50 percent chance of inheriting the mutated locus. Screening for the targeted gene was carried out by Southern blot analysis of StuI-digested DNA from tail biopsies, using the probe utilized in identifying targeted ES clones (probe A, FIG. 21f). As expected, approximately 50 percent of the agouti offspring showed a hybridizing StuI band of approximately 3 kb in addition to the wild-type band of 4.7 kb, demonstrating germline transmission of the targeted $J_H$ gene segment.

In order to generate mice homozygous for the mutation, heterozygotes were bred together and the heavy chain genotype of the offspring determined as described above. As expected, three genotypes were derived from the heterozygote matings: wild-type mice bearing two copies of the normal $J_H$ locus, heterozygotes caring one targeted copy of the gene and one normal copy, and mice homozygous for the $J_H$ mutation. The absence of $J_H$ sequences from these latter mice was verified by hybridization of the Southern blots of StuI-digested DNA with a probe specific for $J_H$ (probe C, FIG. 21a). Whereas hybridization of the $J_H$ probe to a 4.7 kb fragment in DNA samples from heterozygous and wild-type siblings was observed, no signal was present in samples

49 from the $J_H$-mutant homozygotes, attesting to the generation of a novel mouse strain in which both copies of the heavy chain gene have been mutated by deletion of the $J_H$ sequences.

EXAMPLE 12

Heavy Chain Minilocus Transgene

A. Construction of plasmid vectors for cloning large DNA sequences 1. pGP1a

The plasmid pBR322 was digested with EcoRI and StyI and ligated with the following oligonucleotides:

oligo-42 5'- caa gag ccc gcc taa tga gcg ggc ttt ttt ttg cat act gcg gcc gct -3'(SEQ ID NO:51)

oligo-43 5'- aat tag cgg ccg cag tat gca aaa aaa agc ccg ctc att agg cgg gct -3'(SEQ ID NO:52)

The resulting plasmid, pGP1a, is designed for cloning very large DNA constructs that can be excised by the rare cutting restriction enzyme NotI. It contains a NotI restriction site downstream (relative to the ampicillin resistance gene, AmpR) of a strong transcription termination signal derived from the trpA gene (Christie et al., Proc. Natl. Acad. Sci. USA 78: 4180 (1981)). This termination signal reduces the potential toxicity of coding sequences inserted into the NotI site by eliminating readthrough transcription from the AmpR gene. In addition, this plasmid is low copy relative to the pUC plasmids because it retains the pBR322 copy number control region. The low copy number further reduces the potential toxicity of insert sequences and reduces the selection against large inserts due to DNA replication. The vectors pGP1b, pGP1c, pGP1d, and pGP1f are derived from pGP1a and contain different polylinker cloning sites. The polylinker sequences are given below pGP1a
NotI
GCGGCCGC
pGP1b
NotI XhoI ClaI BamHI HindIII NotI
G C g g c c g c c t c g a g a t c a c t a t c g a t- taattaaggatccagcagtaagcttgcGGCCGC (SEQ ID NO:53)
pGI1c
NotI SmaI XhoI SalI HindIII BamHI SacII NotI
G C g g c c g c a t c c c g g g t c t c g a g g t c g a- caagctttcgaggatccgcGGCCGC (SEQ ID NO:54)
pGP1d

50

NotI SalI HindIII ClaI BaInHI XhoI NotI
GCggccgctgtcgacaagcttatcgatggatcctcgagtgcGGCCGC (SEQ ID NO:55)
pGP1f
NotI SalI HindIII EcoRI ClaI KpnI BamHI XhoI NotI
G C g g c c g c t g t c g a c a a g c t t c g a a t- tcagatcgatgtggtacctggatcctcgagtgcGGCCGC (SEQ ID NO:56)

Each of these plasmids can be used for the construction of large transgene inserts that are excisable with NotI so that the transgene DNA can be purified away from vector sequences prior to microinjection.

2. PGP1b pGP1a was digested with NotI and ligated with the following oligonucleotides:

oligo-47 5'- ggc cgc aag ctt act gct gga tcc tta att aat cga tag tga tct cga ggc -3'(SEQ ID NO:57)

oligo-48 5'- ggc cgc ctc gag atc act atc gat taa tta agg atc cag cag taa gct tgc -3'(SEQ ID NO:58)

The resulting plasmid, pGP1b, contains a short polylinker region flanked by NotI sites. This facilitates the construction of large inserts that can be excised by NotI digestion.

3. pGPe

The following oligonucleotides:

oligo-44 5'- ctc cag gat cca gat atc agt acc tga aac agg gct tgc -3'(SEQ ID NO:59)

oligo-45 5'- ctc gag cat gca cag gac ctg gag cac aca cag cct tcc -3'(SEQ ID NO:60)

were used to amplify the immunoglobulin heavy chain 3' enhancer (S. Petterson, et al., Nature 344: 165–168 (1990)) from rat liver DNA by the polymerase chain reaction technique.

Figure 22:
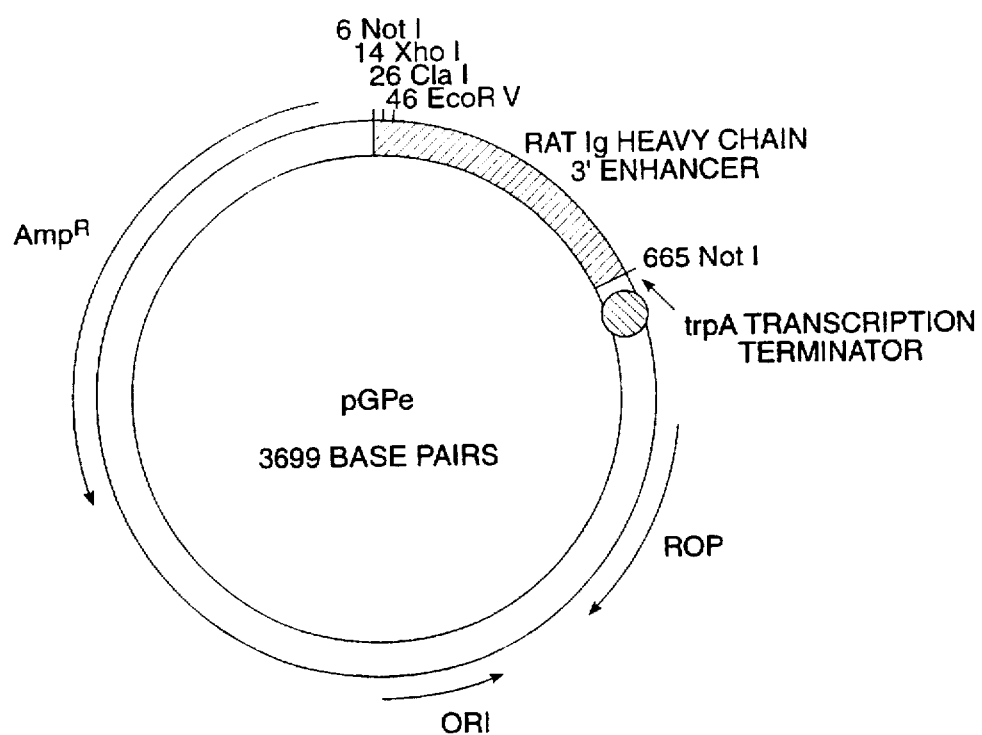
FIG. 22 depicts the map of vector pGPe.

The amplified product was digested with BamHI and SphI and cloned into BamHI/SphI digested pNN03 (pNN03 is a pUC derived plasmid that contains a polylinker with the following restriction sites, listed in order: NotI, BamHI, NcoI, ClaI, EcoRV, XbaI, SacI, XhoI, SphI, PstI, BglII, EcoRI, SmaI, KpnI, HindIII, and NotI). The resulting plasmid, pRE3, was digested with BamHI and HindIII, and the insert containing the rat Ig heavy chain 3' enhancer cloned into BamHI/HindIII digested pGP1b. The resulting plasmid, pGPe (FIG. 22 and Table 1), contains several unique restriction sites into which sequences can be cloned and subsequently excised together with the 3' enhancer by NotI digestion.

TABLE 1

SEQ ID NO: 120

AATTAGCggccgcctcgagatcactatcgattaattaaggatccagatatcagtacccgaaacagggcttgctcacaaca
tctctctctctgtctctctgtctctgtgtgtgtctctctctgtctctgtctctctctgtctctctctgtctctgtgtg
tctctctctgtctctctctctgtctctctgtctctctgtctgtctctgtctctgtctctctctctctctctc
tcggggcacatgcaaatggatgtttgttccatgcagaaaaacatgtttctcattctctgagccaaaaatagcatcaatga
ttcccccaccctgcagctgcaggttcaccccacctggccaggttgaccagctttggggatggggctgggggttccatgac
ccctaacggtgacattgaattcagtgttttcccatttatcgacactgctggaatctgaccctaggagggaatgacaggag
ataggcaaggtccaaacaccccagggaagtgggagagacaggaaggctgtgtgtgctccaggtcctgtgcatgctgcaga
tctgaattcccgggtaccaagcttgcGGCCGCAGTATGCAAAAAAAAGCCCGCTCATTAGGCGGGCTCTTGGCAGAACAT
ATCCATCGCGTCCGCCATCTCCAGCAGCCGCACGCGGCGCATCTCGGGCAGCGTTGGGTCCTGGCCACGGGTGCGCATGA
TCGTGCTCCTGTCGTTGAGGACCCGGCTAGGCTGGCGGGGTTGCCTTACTGGTTAGCAGAATGAATCACCGATACGCGAG
CGAACGTGAAGCGACTGCTGCTGCAAAACGTCTGCGACCTGAGCAACAACATGAATGGTCTTCGGTTTCCGTGTTTCGTA
AAGTCTGGAAACGCGGAAGTCAGCGCCCTGCACCATTATGTTCCGGATCTGCATCGCAGGATGCTGCTGGCTACCCTGTG
GAACACCTACATCTGTATTAACGAAGCGCTGGCATTGACCCTGAGTGATTTTTCTCTGGTCCCGCCGCATCCATACCGCC
AGTTGTTTACCCTCACAACGTTCCAGTAACCGGGCATGTTCATCATCAGTAACCCGTATCGTGAGCATCCTCTCTCGTTT
CATCGGTATCATTACCCCCATGAACAGAAATTCCCCCTTACACGGAGGCATCAAGTGACCAAACAGGAAAAAACCGCCCT
TAACATGGCCCGCTTTATCAGAAGCCAGACATTAACGCTTCTGGAGAAACTCAACGAGCTGGACGCGGATGAACAGGCAG
ACATCTGTGAATCGCTTCACGACCACGCTGATGAGCTTTACCGCAGCTGCCTCGCGCGTTTCGGTGATGACGGTGAAAAC
CTCTGACACATGCAGCTCCCGGAGACGGTCACAGCTTGTCTGTAAGCGGATGCCGGGAGCAGACAAGCCCGTCAGGGCGC

TABLE 1-continued

SEQ ID NO: 120

```
GTCAGCGGGTGTTGGCGGGTGTCGGGGCGCAGCCATGACCCAGTCACGTAGCGATAGCGGAGTGTATACTGGCTTAACTA
TGCGGCATCAGAGCAGATTGTACTGAGAGTGCACCATATGCGGTGTGAAATACCGCACAGATGCGTAAGGAGAAAATACC
GCATCAGGCGCTCTTCCGCTTCCTCGCTCACTGACTCGTCGGTCGTTCGGCTGCGGCGAGCGGTATCAGCTCAC
TCAAAGGCGGTAATACGGTTATCCACAGAATCAGGGGATAACGCAGGAAAGAACATGTGAGCAAAAGGCCAGCAAAAGGC
CAGGAACCGTAAAAAGGCCGCGTTGCTGGCGTTTTTCCATAGGCTCCGCCCCCTGACGAGCATCACAAAAATCGACGCT
CAAGTCAGAGGTGGCGAAACCCGACAGGACTATAAAGATACCAGGCGTTTCCCCCTGGAAGCTCCCTCGTGCGCTCTCCT
GTTCCGACCCTGCCGCTTACCGGATACCTGTCCGCCTTTCTCCCTTCGGGAAGCGTGGCGCTTTCTCATAGCTCACGCTG
TAGGTATCTCAGTTCGGTGTAGGTCGTTCGCTCCAAGCTGGGCTGTGTGCACGAACCCCCCGTTCAGCCCGACCGCTGCG
CCTTATCCGGTAACTATCGTCTTGAGTCCAACCCGGTAAGACACGACTTATCGCCACTGGCAGCAGCCACTGGTAACAGG
ATTAGCAGAGCGAGGTATGTAGGCGGTGCTACAGAGTTCTTGAAGTGGTGGCCTAACTACGGCTACACTAGAAGGACAGT
ATTTGGTATCTGCGCTCTGCTGAAGCCAGTTACCTTCGGAAAAAGAGTTGGTAGCTCTTGATCCGGCAAACAAACCACCG
CTGGTAGCGGTGGTTTTTTTGTTTGCAAGCAGCAGATTACGCGCAGAAAAAAAGGATCTCAAGAAGATCCTTTGATCTTT
TCTACGGGGTCTGACGCTCAGTGGAACGAAAACTCACGTTAAGGGATTTTGGTCATGAGATTATCAAAAAGGATCTTCAC
CTAGATCCTTTTAAATTAAAAATGAAGTTTTAAATCAATCTAAAGTATATATGAGTAAACTTGGTCTGACAGTTACCAAT
GCTTAATCAGTGAGGCACCTATCTCAGCGATCTGTCTATTTCGTTCATCCATAGTTGCCTGACTCCCCGTCGTGTAGATA
ACTACGATACGGGAGGGCTTACCATCTGGCCCCAGTGTCGCAATGATACCGCGAGACCCACGCTCACCGGCTCCAGATTT
ATCAGCAATAAACCAGCCAGCCGGAAGGGCCGAGCGCAGAAGTGGTCCTGCAACTTTATCCGCCTCCATCCAGTCTATTA
ATTGTTGCCGGGAAGCTAGAGTAAGTAGTTCGCCAGTTAATAGTTTGCGCAACGTTGTTGCCATTGCTGCAGGCATCGTG
GTGTCACGCTCGTCGTTTGGTATGGCTTCATTCAGCTCCGGTTCCCAACGATCAAGGCGAGTTACATGATCCCCCATGTT
GTGCAAAAAAGCGGTTAGCTCCTTCGGTCCTTCAGATCGTTGTCAGAAGTAAGTTGGCCGCAGTGTTATCACTCATGGTTA
TGGCAGCACTGCATAATTCTCTTACTGTCATGCCATCCGTAAGATGCTTTTCTGTGACTGGTGAGTACTCAACCAAGTCA
TTCTGAGAATAGTGTATGCGGCGACCGAGTTGCTCTTGCCCGGCGTCAACACGGGATAATACCGCGCCACATAGCAGAAC
TTTAAAAGTGCTCATCATTGGAAAACGTTCTTCGGGGCGAAAACTCTCAAGGATCTTACCGCTGTTGAGATCCAGTTCGA
TGTAACCCACTCGTGCACCCAACTGATCTTCAGCATCTTTTACTTTCACCAGCGTTTCTGCGTGAGCCAAAACAGGAAGG
CAAAATGCCGCAAAAAAGGGAATAAGGGCGACACGGAAATGTTTGAATACTCATACTCTTCCTTTTCAATATTATTGAAG
CATTTATCAGGGTTATTGTCTCATGAGCGGATThCATATTTGAATGTATTTAGAAAAAATAAACAAATAGGGGCTCCGCGCA
CATTTCCCCGAAAAGTGCCACCTGACGTCTAAGAAACCATTATTATCATGACATTAACCTATAAAAATAGGCGTATCACG
AGGCCCTTTCGTCTTCAAG
```
Sequence of vector pGPe.

B. Construction of IgM expressing minilocus transgene, pIGM1

1. Isolation of J-μ constant region clones and construction of pJM1

A human placental genomic DNA library cloned into the phage vector AEMBL3/SP6/T7 (Clonetech Laboratories, Inc., Palo Alto, Calif.) was screened with the human heavy chain J region specific oligonucleotide:

oligo-1 5'- gga ctg tgt ccc tgt gtg atg ctt ttg atg tct ggg gcc aag -3'(SEQ ID NO:64)

and the phage clone 1.3 isolated. A 6 kb HindIII/KpnI fragment from this clone, containing all six J segments as well as D segment DHQ52 and the heavy chain J-μ intronic enhancer, was isolated. The same library was screened with the human μ specific oligonucleotide:

oligo-2 5'- cac caa gtt gac ctg cct ggt cac aga cct gac cac cta tga -3'(SEQ ID NO:65)

and the phage clone λ2.1 isolated. A 10.5 kb HindIII/XhoI fragment, containing the μ switch region and all of the μ constant region exons, was isolated from this clone. These two fragments were ligated together with KpnI/XhoI digested pNNO3 to obtain the plasmid pJM1.

2. pJM2

Figure 23:
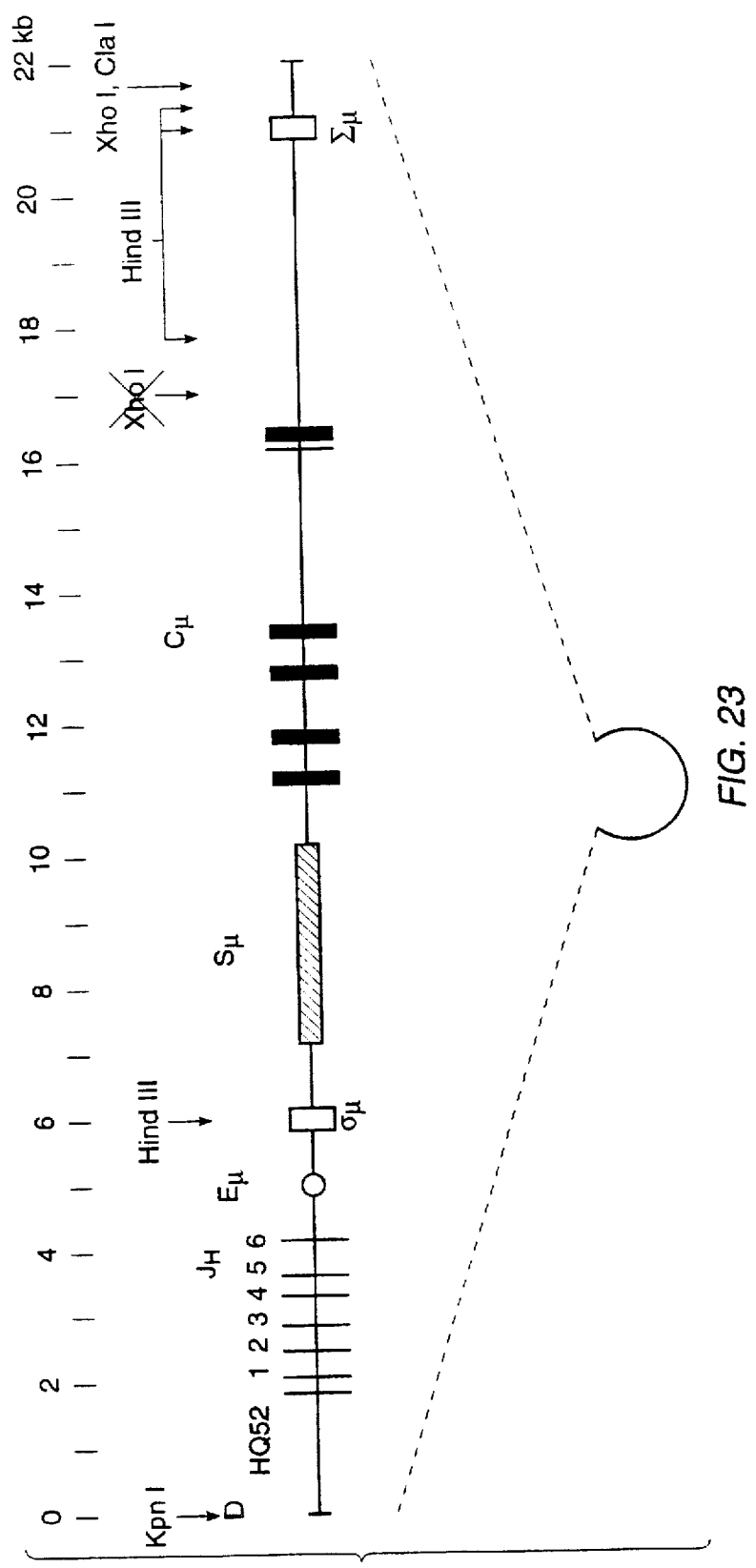
FIG. 23 depicts the structure of vector pJM2.

A 4 kb XhoI fragment was isolated from phage clone λ2.1 that contains sequences immediately downstream of the sequences in pJM1, including the so called Σμ element involved in δ-associated deleteon of the μ in certain IgD expressing B-cells (Yasui et al., Eur. J. Immunol. 19: 1399 (1989), which is incorporated herein by reference). This fragment was treated with the Klenow fragment of DNA polymerase I and ligated to XhoI cut, Klenow treated, pJM1. The resulting plasmid, pJM2 (FIG. 23), had lost the internal XhoI site but retained the 3' XhoI site due to incomplete reaction by the Klenow enzyme. pJM2 contains the entire human J region, the heavy chain J-μ intronic enhancer, the μ switch region and all of the g constant region exons, as well as the two 0.4 kb direct repeats, σμ and Σv, involved in S-associated deletion of the μ gene.

3. Isolation of D region clones and construction of DDH1

The following human D region specific oligonucleotide:

oligo-4 5'- tgg tat tac tat ggt tcg ggg agt tat tat aac cac 10 agt gtc -3'(SEQ ID NO:66)

was used to screen the human placenta genomic library for D region clones. Phage clones λ4.1 and λ4.3 were isolated. A 5.5 kb XhoI fragment, that includes the D elements $D_{K1}$, $D_{N1}$, and $D_{M2}$ (Ichihara et al., EMBO J. 7: 4141 (1988)), was isolated from phage clone 14.1. An adjacent upstream 5.2 kb XhoI fragment, that includes the D elements $D_{LR1}D_{XP1}$, $D_{XP'1}$, and $D_{A1}$, was isolated from phage clone λ4.3. Each of these D region XhoI fragments were cloned into the SalI site of the plasmid vector pSP72 (Promega, Madison, Wis.) so as to destroy the XhoI site linking the two sequences. The upstream fragment was then excised with XhoI and SmaI, and the downstream fragment with EcoRV and XhoI. The resulting isolated fragments were ligated together with SalI digested pSP72 to give the plasmid pDH1. pDH1 contains a 10.6 kb insert that includes at least 7 D segments and can be excised with XhoI (5') and EcoRV (3').

4. pCOR1

Figure 24:
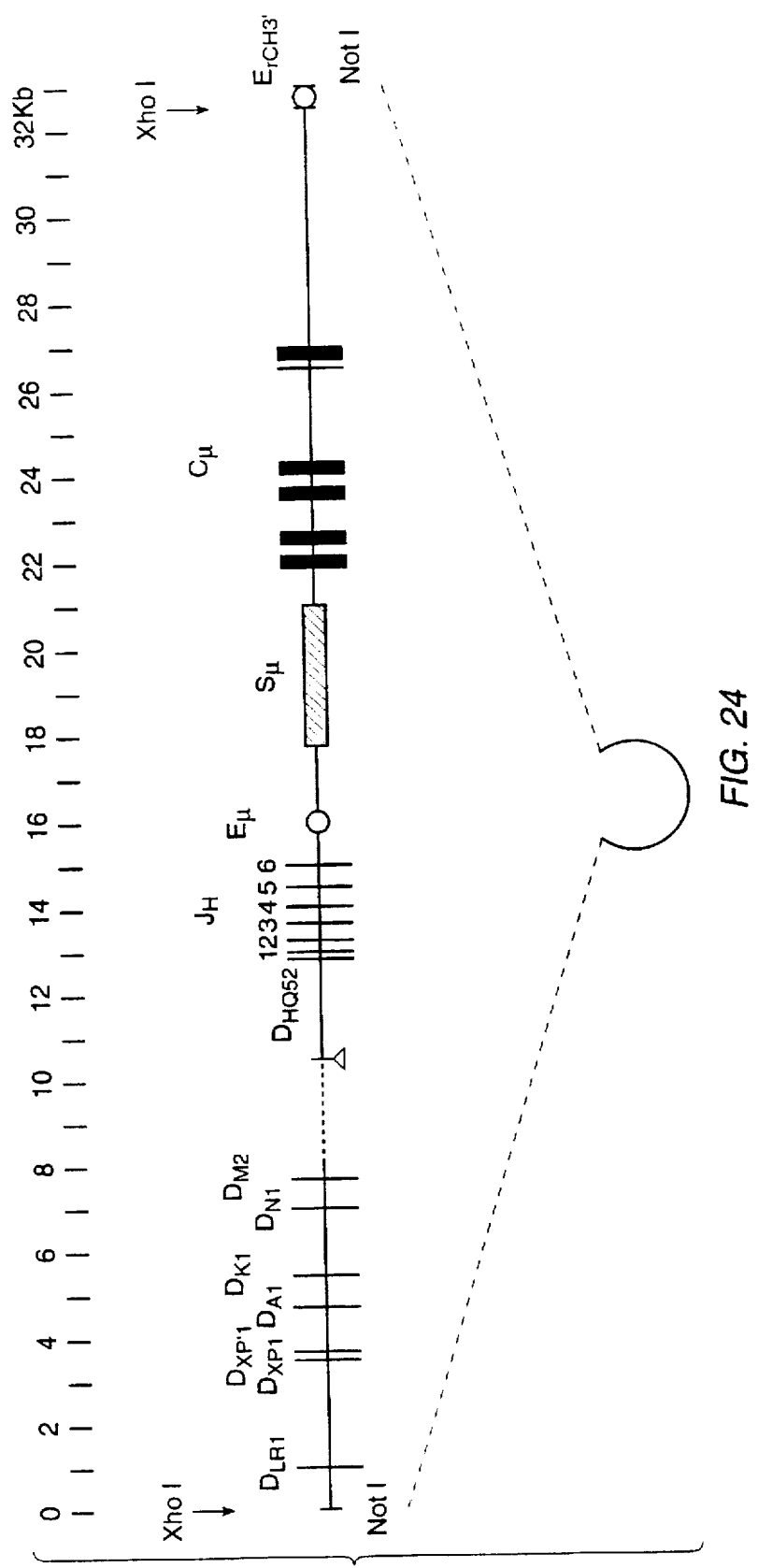
FIG. 24 depicts the structure of vector pCOR1.

The plasmid pJM2 was digested with Asp718 (an isoschizomer of KpnI) and the overhang filled in with the Klenow fragment of DNA polymerase I. The resulting DNA was then digested with ClaI and the insert isolated. This insert was ligated to the XhoI/EcoRV insert of pDH1 and XhoI/ClaI digested pGPe to generate pCOR1 (FIG. 24).

5. pVH251

A 10.3 kb genomic HindIII fragment containing the two human heavy chain variable region segments $V_H251$ and $V_H105$ (Humphries et al., Nature 331: 446 (1988), which is incorporated herein by reference) was subcloned into pSP72 to give the plasmid pVH251.

6. pIGM1

Figure 25:
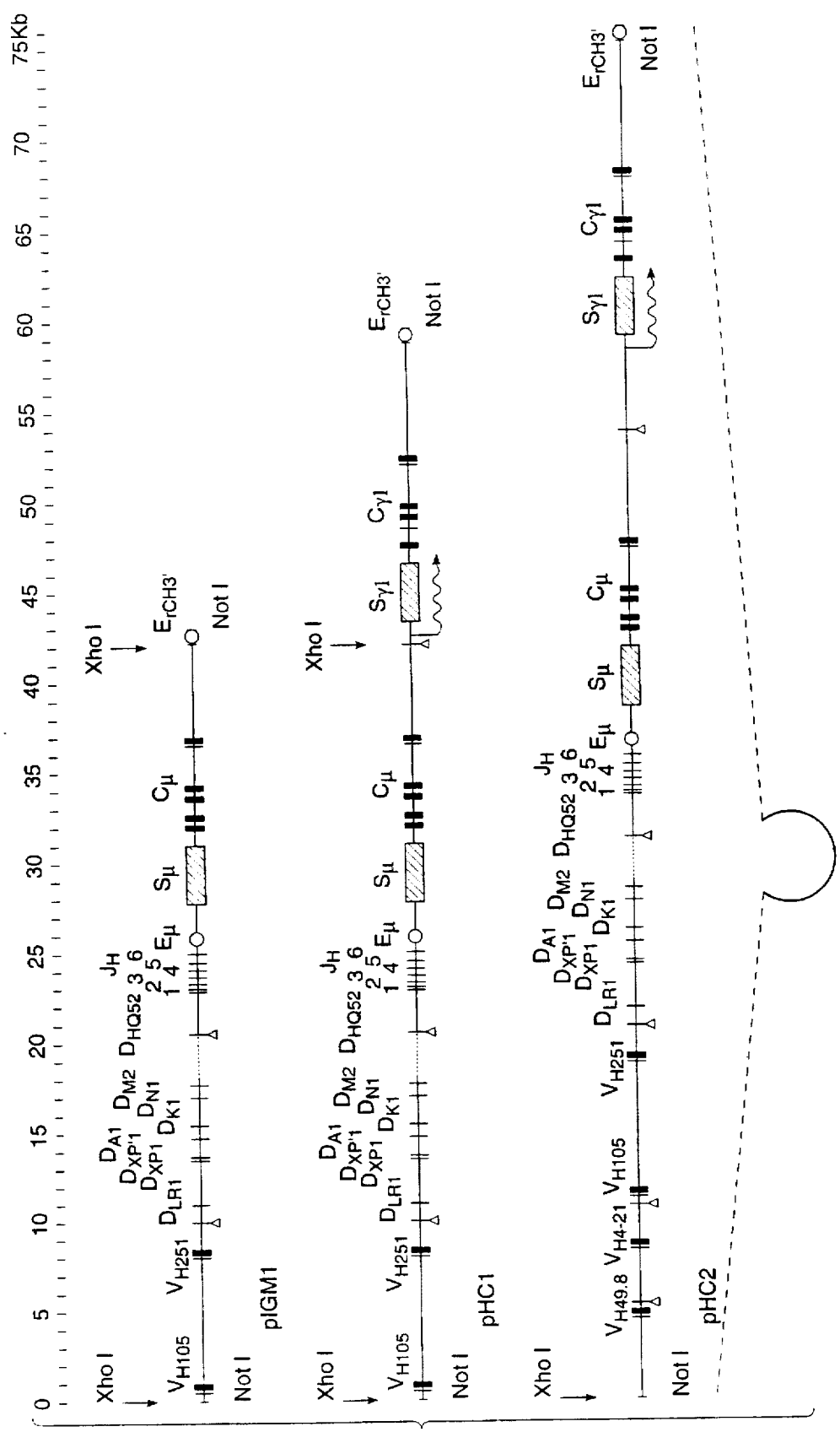
FIG. 25 depicts the transgene constructs for pIGM1, pHC1 and pHC2.

The plasmid pCOR1 was partially digested with XhoI and the isolated XhoI/SalI insert of pVH251 cloned into the upstream XhoI site to generate the plasmid pIGM1 (FIG. 25). pIGM1 contains 2 functional human variable region segments, at least 8 human D segments all 6 human $J_H$ segments, the human J-μ enhancer, the human σμ element, the human μ switch region, all of the human μ coding exons, and the human Σν element, together with the rat heavy chain 3' enhancer, such that all of these sequence elements can be isolated on a single fragment, away from vector sequences, by digestion with NotI and microinjected into mouse embryo pronuclei to generate transgenic animals.

C. Construction of IgM and IgG expressing minilocus transgene, pHC1

1. Isolation of γ constant region clones

The following oligonucleotide, specific for human Ig g constant region genes:

oligo-29 5'- cag cag gtg cac acc caa tgc cca tga gcc cag aca ctg gac -3'(SEQ ID NO:67)

was used to screen the human genomic library. Phage clones 129.4 and 129.5 were isolated. A 4 kb HindIII fragment of phage clone μ29.4, containing a γ switch region, was used to probe a human placenta genomic DNA library cloned into the phage vector lambda FIX™ II (Stratagene, La Jolla, Calif.). Phage clone λSg1.13 was isolated. To determine the subclass of the different γ clones, dideoxy sequencing reactions were carried out using subclones of each of the three phage clones as templates and the following oligonucleotide as a primer:

oligo-67 5'- tga gcc cag aca ctg gac -3'(SEQ ID NO:68)

Phage clones 129.5 and λSγ1.13 were both determined to be of the γ1 subclass.

2. pγe1

A 7.8 kb HindIII fragment of phage clone 129.5, containing the γ1 coding region was cloned into pUC18. The resulting plasmid, pLT1, was digested with XhoI, Klenow treated, and religated to destroy the internal XhoI site. The resulting clone, pLT1xk, was digested with HindIII and the insert isolated and cloned into pSP72 to generate the plasmid clone pLT1xks. Digestion of pLT1xks at a polylinker XhoI site and a human sequence derived BamHI site generates a 7.6 kb fragment containing the γ1 constant region coding exons. This 7.6 kb XhoI/BamHI fragment was cloned together with an adjacent downstream 4.5 kb BamHI fragment from phage clone λ29.5 into XhoI/BamHI digested pGPe to generate the plasmid clone pγe1. pγe1 contains all of the γ1 constant region coding exons, together with 5 kb of downstream sequences, linked to the rat heavy chain 3' enhancer.

3. pγe2

A 5.3 kb HindIII fragment containing the γ1 switch region and the first exon of the pre-switch sterile transcript (P.

Figure 26:
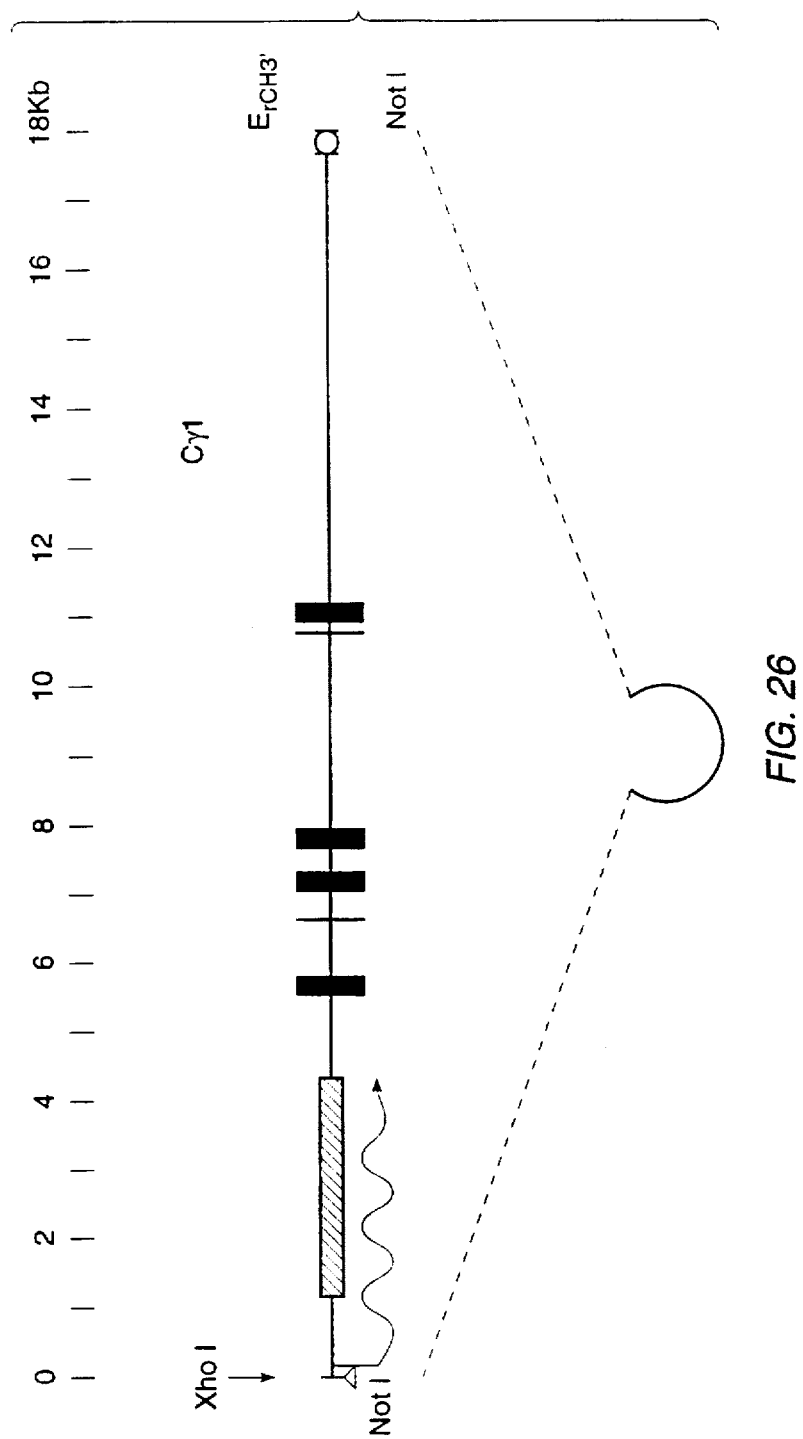
FIG. 26 depicts the structure of pγe2.

Sideras et al. (1989) *International Immunol.* 1, 631) was isolated from phage clone λSγ1.13 and cloned into pSP72 with the polylinker XhoI site adjacent to the 5' end of the insert, to generate the plasmid clone psγ1s. The XhoI/SalII insert of pSγ1s was cloned into XhoI digested pγe1 to generate the plasmid clone pγe2 (FIG. 26). pγe2 contains all of the γ1 constant region coding exons, and the upstream switch region and sterile transcript exons, together with 5 kb of downstream sequences, linked to the rat heavy chain 3' enhancer. This clone contains a unique XhoI site at the 5' end of the insert. The entire insert, together with the XhoI site and the 3' rat enhancer can be excised from vector sequences by digestion with NotI.

4. pHC1

The plasmid pIGM1 was digested with XhoI and the 43 kb insert isolated and cloned into XhoI digested pge2 to generate the plasmid pHC1 (FIG. 25). pHC1 contains 2 functional human variable region segments, at least 8 human D segments all 6 human $J_H$ segments, the human J-μ enhancer, the human σμ element, the human μ switch region, all of the human μ coding exons, the human Σμ element, and the human γ1 constant region, including the associated switch region and sterile transcript associated exons, together with the rat heavy chain 3' enhancer, such that all of these sequence elements can be isolated on a single fragment, away from vector sequences, by digestion with NotI and microinjected into mouse embryo pronuclei to generate transgenic animals.

D. Construction of IgM and IgG expressing minilocus transgene, pHC2

1. Isolation of human heavy chain V region gene VH49.8

The human placental genomic DNA library lambda, FIX™ II, Stratagene, La Jolla, Calif.) was screened with the following human VH1 family specific oligonucleotide:

oligo-49 5'- gtt aaa gag gat ttt att cac ccc tgt gtc ctc tcc aca ggt gtc -3' (SEQ ID NO:69)

Phage clone A49.8 was isolated and a 6.1 kb XbaI fragment containing the variable segment VH49.8 subcloned into pNNO3 (such that the polylinker ClaI site is downstream of VH49.8 and the polylinker XhoI site is upstream) to generate the plasmid pVH49.8. An 800 bp region of this insert was sequenced, and VH49.8 found to have an open reading frame and intact splicing and recombination signals, thus indicating that the gene is functional (Table 2).

TABLE 2

| (SEQ ID NOS:61,62,63) | | | | | |
|---|---|---|---|---|---|
| TTCCTCAGGC | AGGATTTAGG | GCTTGGTCTC | TCAGCATCCC | ACACTTGTAC | 50 |
| AGCTGATGTG | GCATCTGTGT | TTTCTTTCTC | ATCCTAGATC | AAGCTTTGAG | 100 |
| CTGTGAAATA | CCCTGCCTCA | TGAATATGCA | AATAATCTGA | GGTCTTCTGA | 150 |
| GATAAATATA | GATATATTGG | TGCCCTGAGA | GCATCACATA | ACAACCAGAT | 200 |
| TCCTCCTCTA | AAGAAGCCCC | TGGGAGCACA | GCTCATCACC | ATGGACTGGA Met Asp Trp T | 250 |
| CCTGGAGGTT hr Trp Arg Ph | CCTCTTTGTG e Leu Phe Val | GTGGCAGCAG Val Ala Ala A | CTACAGgt aa la Thr | ggggcttcct | 300 |

TABLE 2-continued (SEQ ID NOS:61,62,63)

| | | | | | |
|---|---|---|---|---|---|
| agt cct aagg | ct gaggaagg | gat cct ggt t | t agt t aaaga | ggat t t t at t | 350 |
| caccccl gt g | t cct ct ccac | ag GTGTCCAG<br>Gly Val Gln | TCCCAGGTCC<br>Ser Gln Val G | AGCTGGTGCA<br>ln Leu Val Gl | 400 |
| GTCTGGGGCT<br>n Ser Gly Ala | GAGGTGAAGA<br>Glu Val Lys L | AGCCTGGGTC<br>ys Pro Gly Se | CTCGGTGAAG<br>r Ser Val Lys | GTCTCCTGCA<br>Val Ser Cys L | 450 |
| AGGCTTCTGG<br>ys Ala Ser Gl | AGGCACCTTC<br>y Gly Thr Phe | AGCAGCTATG<br>Ser Ser Tyr A | CTATCAGCTG<br>la Ile Ser Tr | GGTGCGACAG<br>p Val Arg Gln | 500 |
| GCCCCTGGAC<br>Ala Pro Gly G | AAGGGCTTGA<br>ln Gly Leu Gl | GTGGATGGGA<br>u Trp Met Gly | AGGATCATCC<br>Arg Ile Ile P | CTATCCTTGG<br>ro Ile Leu Gl | 550 |
| TATAGCAAAC<br>y Ile Ala Asn | TACGCACAGA<br>Tyr Ala Gln L | AGTTCCAGGG<br>ys Phe Gln Gl | CAGAGTCACG<br>y Arg Val Thr | ATTACCGCGG<br>Ile Thr Ala A | 600 |
| ACAAATCCAC<br>sp Lys Ser Th | GAGCACAGCC<br>r Ser Thr Ala | TACATGGAGC<br>Tyr Met Glu L | TGAGCAGCCT<br>eu Ser Ser Le | GAGATCTGAG<br>u Arg Ser Glu | 650 |
| GACCACGCCG<br>Asp Thr Ala V | TGTATTACTG<br>al Tyr Tyr Cy | TGCGAGAGA<u>C ACAG</u>TGTGAA<br>s Ala Arg | | AACCCACATC | 700 |
| CTGAGAGT<u>GT CAGAAACC</u>CT | GAGGGAGAAG | GCAGCTGTGC | CGGGCTGAGG | | 750 |
| AGATGACAGG | GTTTATTAGG | TTTAAGGCTG | TTTACAAAAT | GGGTTATATA | 800 |
| TTTGAGAAAA | AA | | | | 812 |

Sequence of human V$_H$I family gene V$_H$49.8

2. pV2

A 4 kb XbaI genomic fragment containing the human V$_H$1V family gene V$_H$4-21 (Sanz et al., *EMBO J.*, 8: 3741 (1989)), subcloned into the plasmid pUC12, was excised with SmaI and HindIII, and treated with the Klenow fragment of polymerase I. The blunt ended fragment was then cloned into ClaI digested, Klenow treated, pVH49.8. The resulting plasmid, pV2, contains the human heavy chain gene VH49.8 linked upstream of VH4-21 in the same orientation, with a unique SalI site at the 3' end of the insert and a unique XhoI site at the 5' end.

3. pSγ1-5'

A 0.7 kb XbaI/HindIII fragment (representing sequences immediately upstream of, and adjacent to, the 5.3 kb γ1 switch region containing fragment in the plasmid pye2) together with the neighboring upstream 3.1 kb XbaI fragment were isolated from the phage clone λSg1.13 and cloned into HindIII/XbaI digested pUC18 vector. The resulting plasmid, pSγ1-5', contains a 3.8 kb insert representing sequences upstream of the initiation site of the sterile transcript found in B-cells prior to switching to the γ1 isotype (P. Sideras et al., *International Immunol.* 1: 631 (1989)). Because the transcript is implicated in the initiation of isotype switching, and upstream cis-acting sequences are often important for transcription regulation, these sequences are included in transgene constructs to promote correct expression of the sterile transcript and the associated switch recombination.

4. pVGE1

The pSγ1-5' insert was excised with SmaI and HindIII, treated with Klenow enzyme, and ligated with the following oligonucleotide linker:

5'- ccg gtc gac cgg -3'(SEQ ID NO:70).

Figure 27:
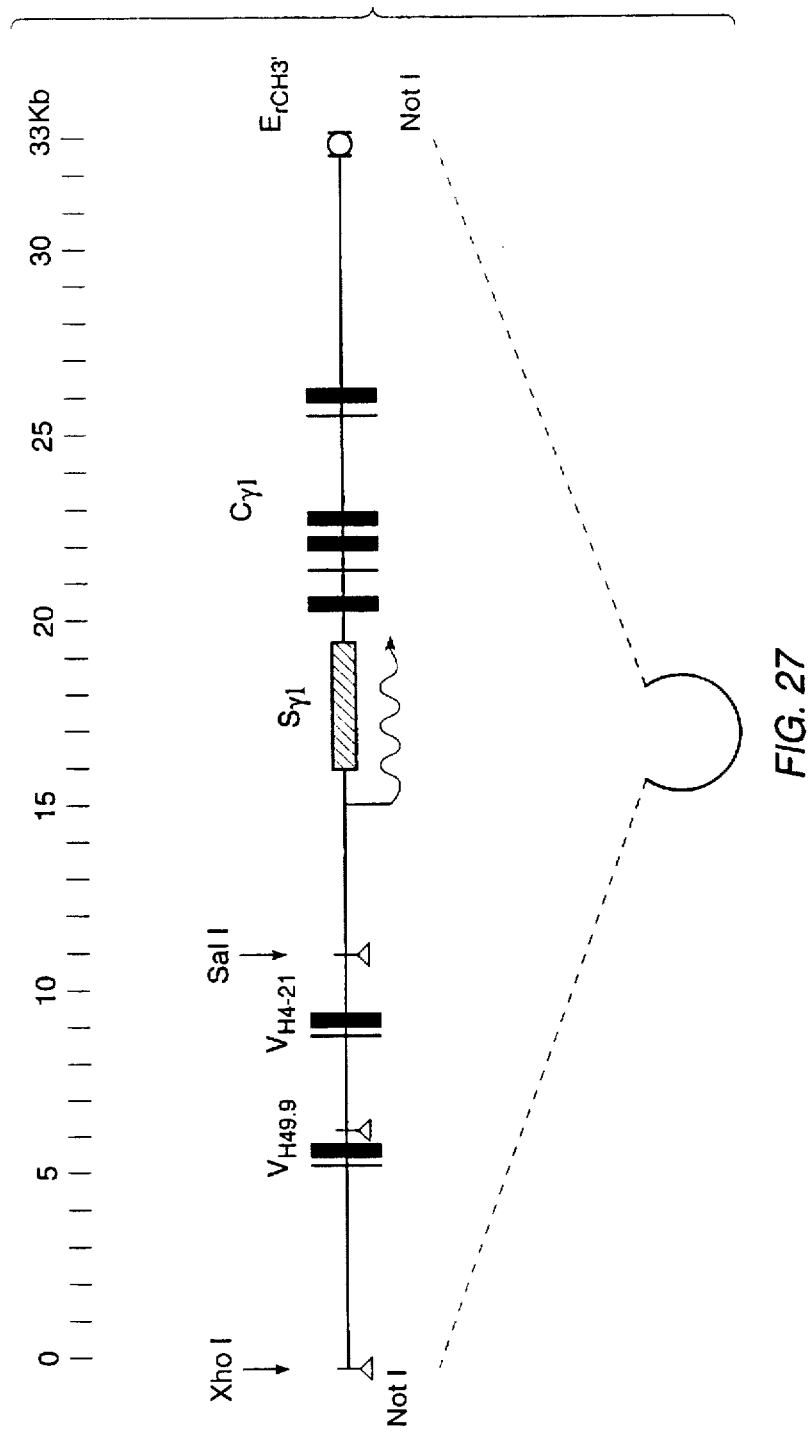
FIG. 27 depicts the structure of pVGE1.

The ligation product was digested with SalI and ligated to SalI digested pV2. The resulting plasmid, pVP, contains 3.8 kb of γ1 switch 5' flanking sequences linked downstream of the two human variable gene segments VH49.8 and VH4-21 (see Table 2). The pVP insert is isolated by partial digestion with SalI and complete digestion with XhoI, followed by purification of the 15 kb fragment on an agarose gel. The insert is then cloned into the XhoI site of pye2 to generate the plasmid clone pVGE1 (FIG. 27). pVGE1 contains two human heavy chain variable gene segments upstream of the human γ1 constant gene and associated switch region. A unique SalI site between the variable and constant regions can be used to clone in D, J, and μ gene segments. The rat heavy chain 3' enhancer is linked to the 3' end of the γ1 gene and the entire insert is flanked by NotI sites.

5. pHC2

The plasmid clone pVGE1 is digested with SalI and the XhoI insert of pIGM1 is cloned into it. The resulting clone, pHC2 (FIG. 25), contains 4 functional human variable region segments, at least 8 human D segments all 6 human J$_H$ segments, the human J-m enhancer, the human σμ element, the human μ switch region, all of the human μ coding exons, the human σμ element, and the human γ1 constant region, including the associated switch region and sterile transcript associated exons, together with 4 kb flanking sequences upstream of the sterile transcript initiation site. These human sequences are linked to the rat heavy chain 3' enhancer, such that all of the sequence elements can be isolated on a single fragment, away from vector sequences, by digestion with NotI and microinjected into mouse embryo pronuclei to generate transgenic animals. A unique XhoI site at the 5' end of the insert can be used to clone in additional human variable gene segments to further expand the recombinational diversity of this heavy chain minilocus.

E. Transgenic mice

Figure 28:
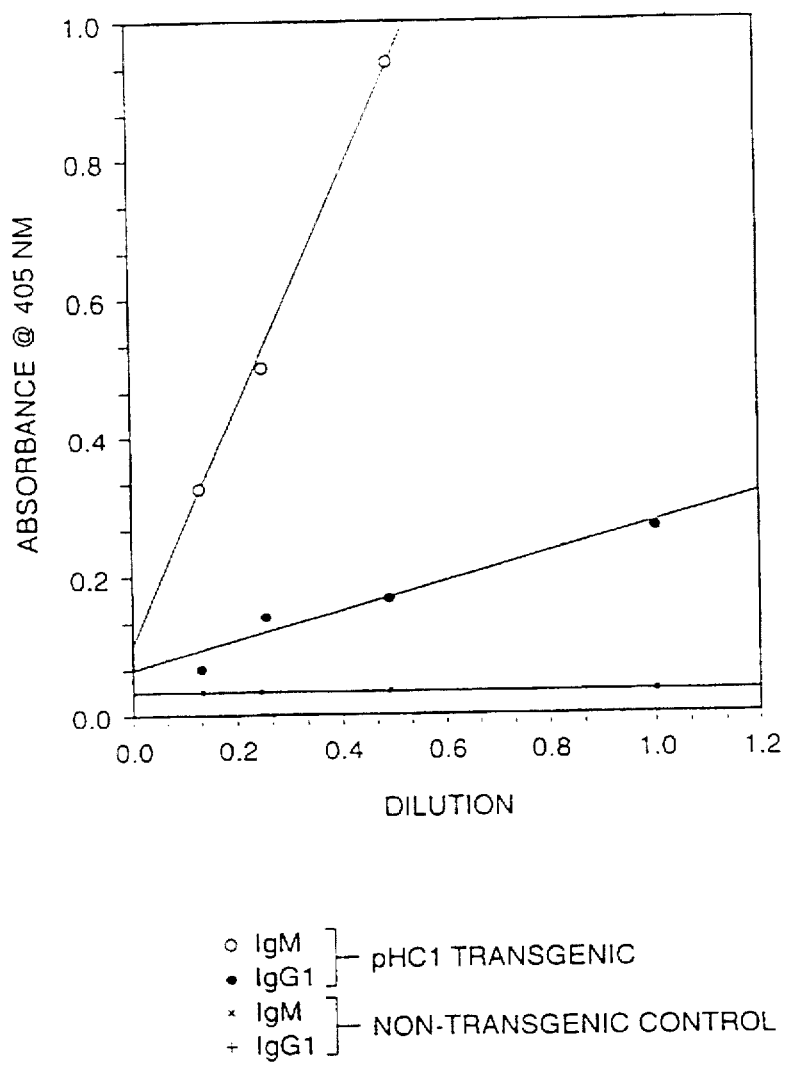
FIG. 28 depicts the assay results of human Ig expression in a pHC1 transgenic mouse.
Figure 29:
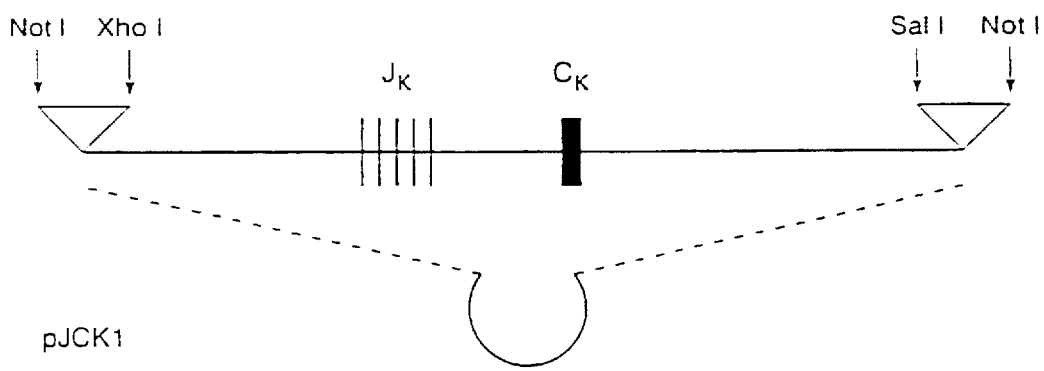
FIG. 29 depicts the structure of pJCK1.
Figure 30:
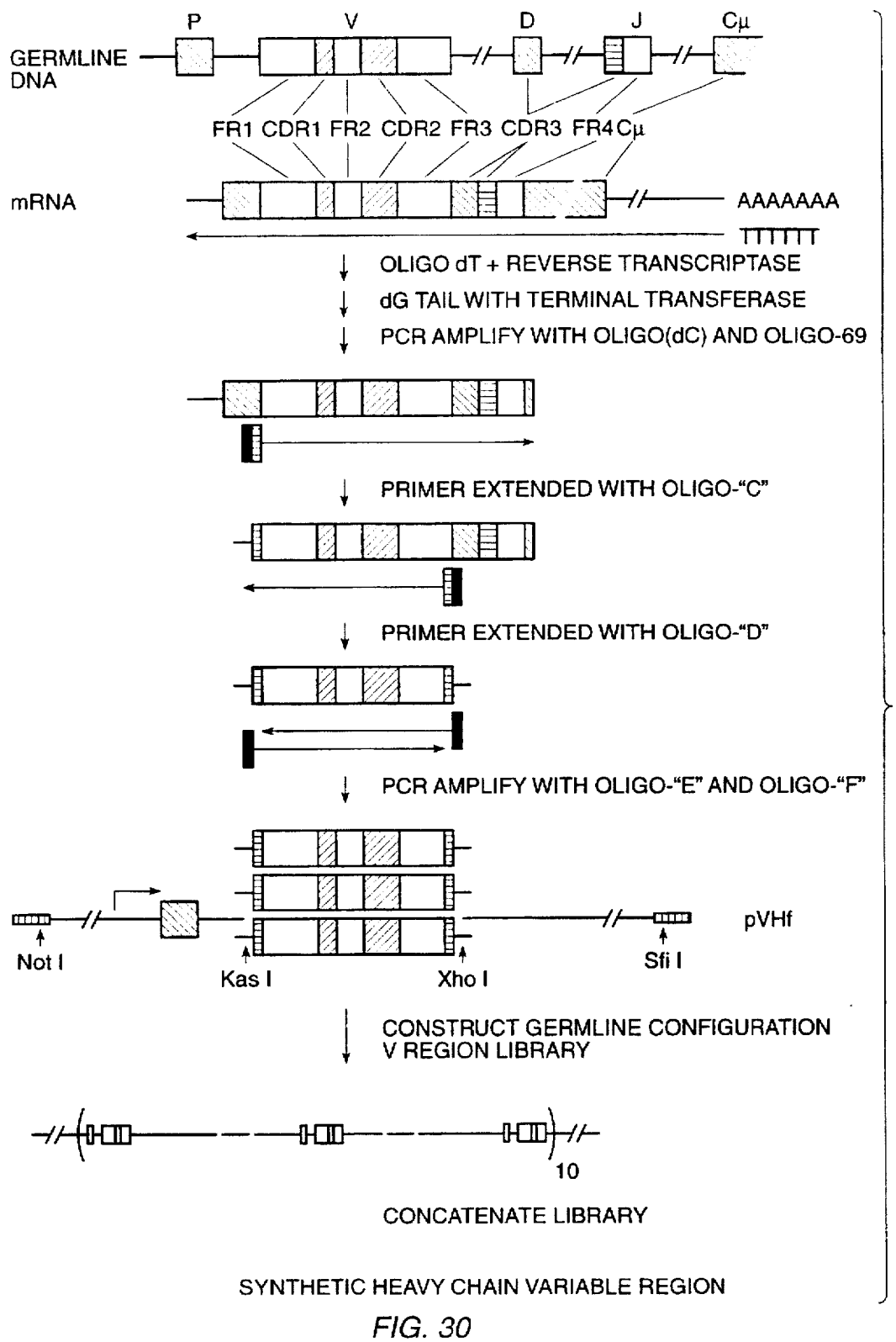
FIG. 30 depicts the construction of a synthetic heavy chain variable region.
Figure 31:
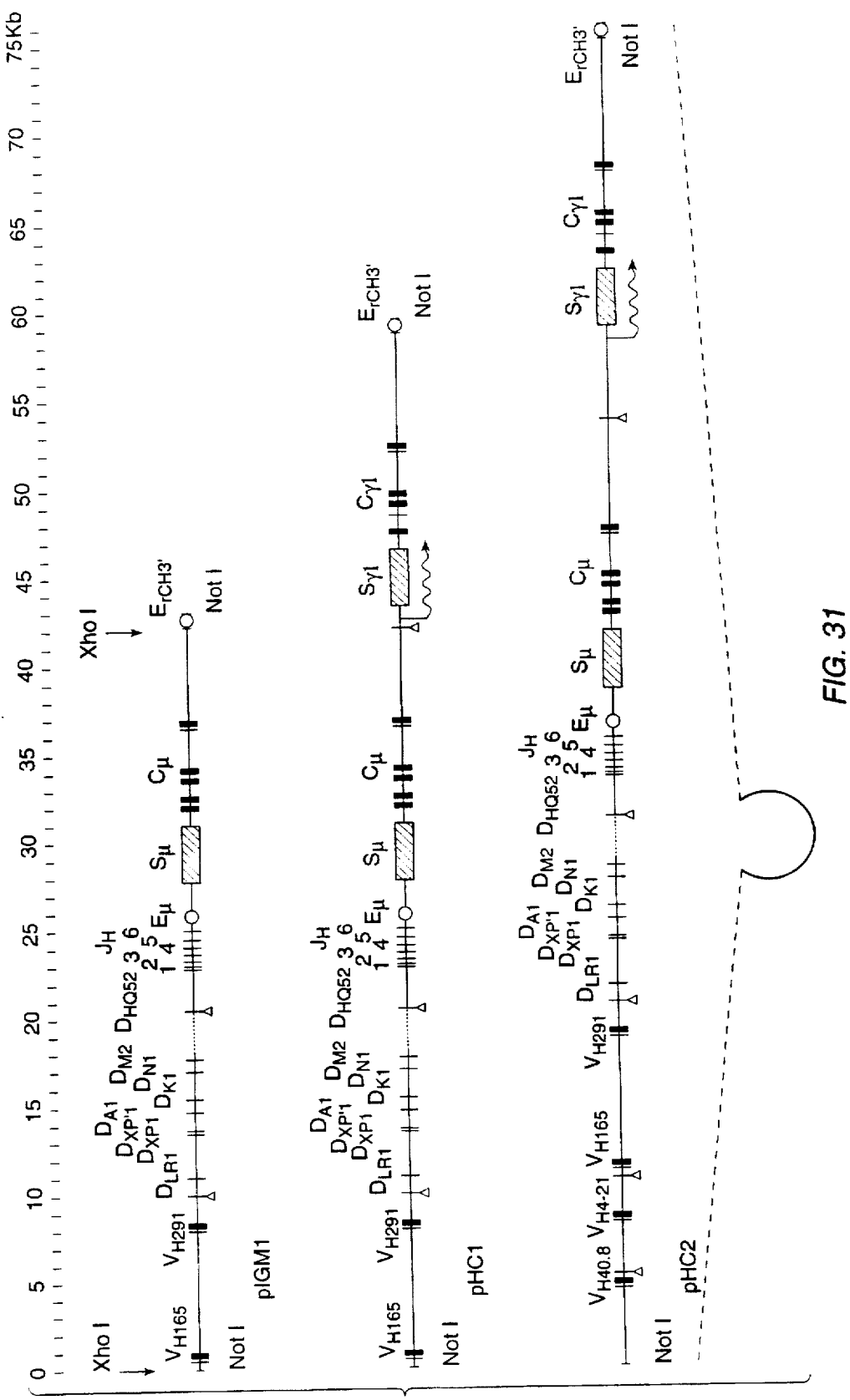
FIG. 31 is a schematic representation of the heavy chain minilocus constructs pIGM$_1$, pHC1, and pHC2.

The NotI inserts of plasmids pIGM1 and pHC1 were isolated from vector sequences by agarose gel electrophoresis. The purified inserts were microinjected into the pronuclei of fertilized (C57BL/6 x CBA)F2 mouse embryos and transferred the surviving embryos into pseudopregnant females as described by Hogan et al. (B. Hogan, F. Costantini, and E. Lacy, Methods of Manipulating the Mouse Embryo, 1986, Cold Spring Harbor Laboratory, N.Y.). Mice that developed from injected embryos were analyzed for the presence of transgene sequences by Southern blot analysis of tail DNA. Transgene copy number was estimated by band intensity relative to control standards containing known quantities of cloned DNA. At 3 to 8 weeks of age, serum was isolated from these animals and assayed for the presence of transgene encoded human IgM and IgG1 by ELISA as described by Harlow and Lane (E. Harlow and D. Lane. Antibodies: A Laboratory Manual, 1988, Cold Spring Harbor Laboratory, N.Y.). Microtiter plate wells were coated with mouse monoclonal antibodies specific for human IgM (clone AF6, #0285, AMAC, Inc. Westbrook, Me.) and human IgG1 (clone JL512, #0280, AMAC, Inc. Westbrook, Me.). Serum samples were serially diluted into the wells and the presence of specific immunoglobulins detected with affinity isolated alkaline phosphatase conjugated goat anti-human Ig (polyvalent) that had been pre-adsorbed to minimize cross-reactivity with mouse immunoglobulins. Table 3 and FIG. 28 show the results of an ELISA assay for the presence of human IgM and IgG1 in the serum of two animals that developed from embryos injected with the transgene insert of plasmid pHC1. All of the control non-transgenic mice tested negative for expression of human IgM and IgG1 by this assay. Mice from two lines containing the pIGM1 NotI insert (lines #6 and 15) express human IgM but not human IgG1. We tested mice from 6 lines that contain the pHC1 insert and found that 4 of the lines (lines #26, 38, 57 and 122) express both human IgM and human IgG1, while mice from two of the lines (lines #19 and 21) do not express detectable levels of human immunoglobulins. The pHC1 transgenic mice that did not express human immunoglobulins were so-called $G_o$ mice that developed directly from microinjected embryos and may have been mosaic for the presence of the transgene. Southern blot analysis indicates that many of these mice contain one or fewer copies of the transgene per cell. The detection of human IgM in the serum of pIGM1 transgenics, and human IgM and IgG1 in pHC1 transgenics, provides evidence that the transgene sequences function correctly in directing VDJ joining, transcription, and isotype switching. One of the animals (#18) was negative for the transgene by Southern blot analysis, and showed no detectable levels of human IgM or IgG1. The second animal (#38) contained approximately 5 copies of the transgene, as assayed by Southern blotting, and showed detectable levels of both human IgM and IgG1. The results of ELISA assays for 11 animals that developed from transgene injected embryos is summarized in the table below (Table 3).

TABLE 3

Detection of human IgM and IgG1 in the serum of transgenic animals by ELISA assay

| animal # | injected transgene | approximate transgene copies per cell | human IgM | human IpG1 |
|---|---|---|---|---|
| 6 | pIGM1 | 1 | ++ | – |
| 7 | pIGM1 | 0 | – | – |
| 9 | pIGM1 | 0 | – | – |
| 10 | pIGM1 | 0 | – | – |
| 12 | pIGM1 | 0 | – | – |
| 15 | pIGM1 | 10 | ++ | – |
| 18 | pHC1 | 0 | – | – |
| 19 | pHC1 | 1 | – | – |
| 21 | pHC1 | <1 | – | – |
| 26 | pHC1 | 2 | ++ | + |
| 38 | pHC1 | 5 | ++ | + |

Table 3 shows a correlation between the presence of integrated transgene DNA and the presence of transgene encoded immunoglobulins in the serum. Two of the animals that were found to contain the pHC1 transgene did not express detectable levels of human immunoglobulins. These were both low copy animals and may not have contained complete copies of the transgenes, or the animals may have been genetic mosaics (indicated by the <1 copy per cell estimated for animal #21), and the transgene containing cells may not have populated the hematopoietic lineage. Alternatively, the transgenes may have integrated into genomic locations that are not conducive to their expression. The detection of human IgM in the serum of pIGM1 transgenics, and human IgM and IgG1 in pHC1 transgenics, indicates that the transgene sequences function correctly in directing VDJ joining, transcription, and isotype switching.

F. cDNA clones

To assess the functionality of the pHC1 transgene in VDJ joining and class switching, as well the participation of the transgene encoded human B-cell receptor in B-cell development and allelic exclusion, the structure of immunoglobulin cDNA clones derived from transgenic mouse spleen mRNA were examined. The overall diversity of the transgene encoded heavy chains, focusing on D and J segment usage, N region addition, CDR3 length distribution, and the frequency of joints resulting in functional mRNA molecules was examined. Transcripts encoding IgM and IgG incorporating VH105 and VH251 were examined.

Figure 34:
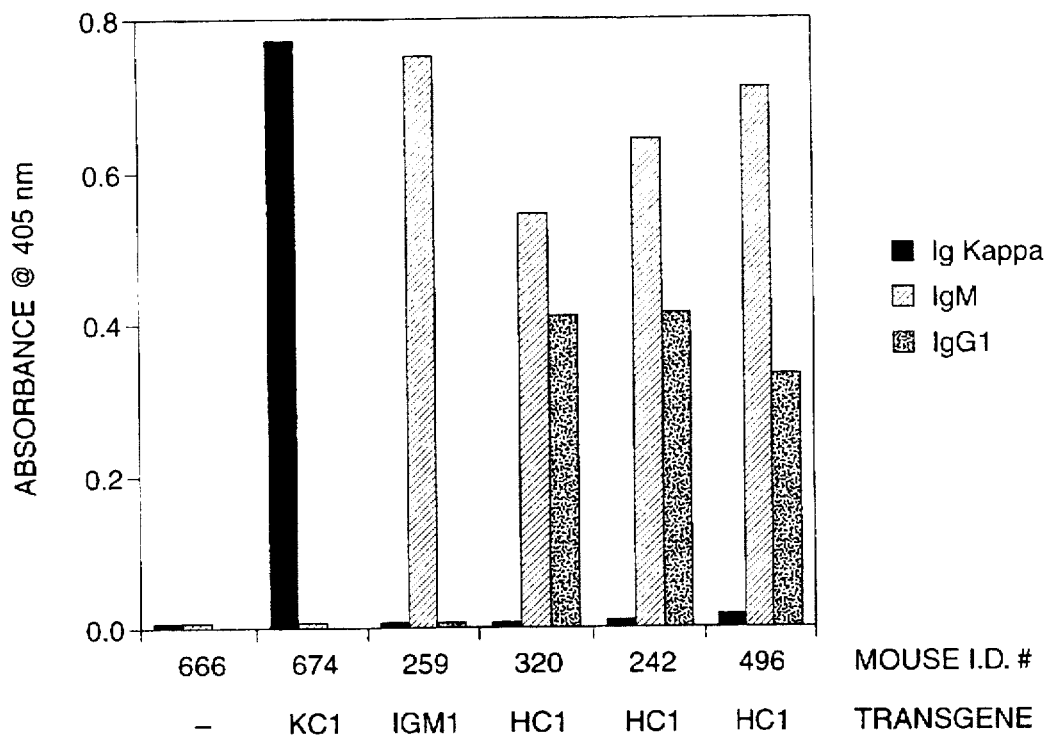
FIG. 34 depicts serum ELISA results
Figure 35:
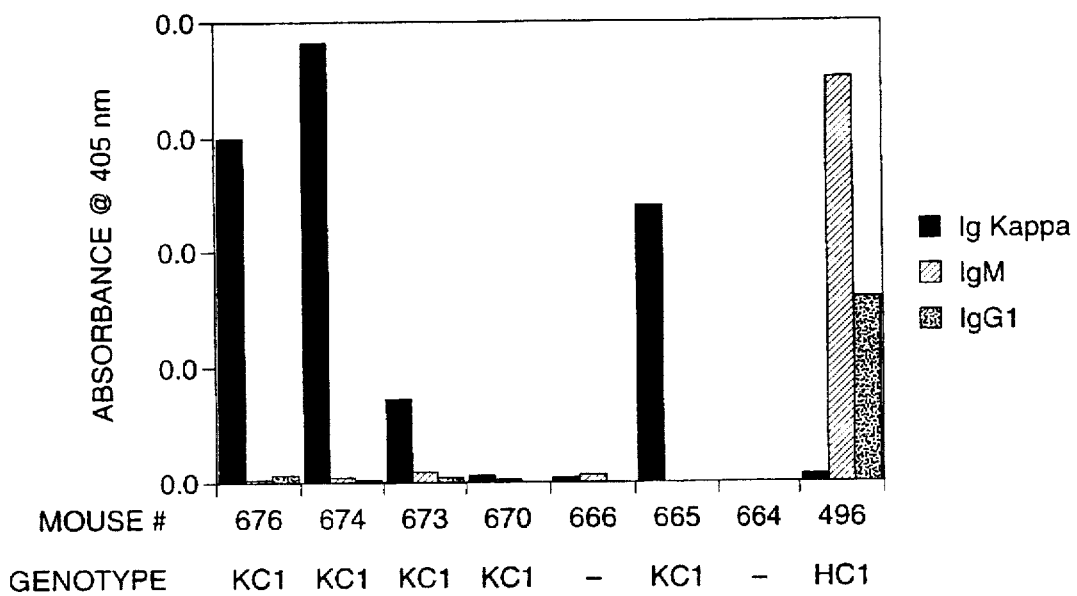
FIG. 35 depicts the results of an ELISA assay of serum from 8 transgenic mice.

Polyadenylated RNA was isolated from an eleven week old male second generation line-57 pHC1 transgenic mouse. This RNA was used to synthesize oligo-dT primed single stranded cDNA. The resulting cDNA was then used as template for four individual PCR amplifications using the following four synthetic oligonucleotides as primers: VH251 specific oligo-149, cta gct cga gtc caa gga gtc tgt gcc gag gtg cag ctg (g,a,t,c) (SEQ ID NO:101); VH105 specific o-150, gtt gct cga gtg aaa ggt gtc cag tgt gag gtg cag ctg (g,a,t,c) (SEQ ID NO:102); human gamma1 specific oligo-151, ggc gct cga gtt cca cga cac cgt cac cgg ttc (SEQ ID NO:103); and human mu specific oligo-152, act gat cga ggc aga caa cgg cca cgc tgc tag (SEQ ID NO:104). Reaction 1 used primers o-149 and o-151 to amplify VH251-gamma1 transcripts, reaction 2 used o-149 and o-152 to amplify VH251-mu transcripts, reaction 3 used o-150 and o-151 to amplify VH105-gamma1 transcripts, and reaction 4 used o-150 and o-152 to amplify VH105-mu transcripts. The resulting 0.5 kb PCR products were isolated from an agarose gel; the μ transcript products were more abundant than the γ transcript products, consistent with the corresponding ELISA data (FIG. 34). The PCR products were digested with XhoI and cloned into the plasmid pNNO3. Double-stranded plasmid DNA was isolated from minipreps of nine clones from each of the four PCR amplifications and dideoxy sequencing reactions were performed. Two of the clones turned out to be deletions containing no D or J segments. These could not have been derived from normal RNA splicing products and are likely to have originated from deletions introduced during PCR amplification. One of the DNA samples turned out to be a mixture of two individual clones, and three additional clones did not produce readable DNA sequence (presumably because the DNA samples were not clean enough). The DNA sequences of the VDJ joints from the remaining 30 clones are compiled in Table 4. Each of the sequences are unique, indicating that no single pathway of gene rearrangement, or single clone of transgene expressing B-cells is dominant. The fact that no two sequences are alike is also an indication of the large diversity of immunoglobulins that can be expressed from a compact minilocus containing only 2 V segments, 10 D segments, and 6 J segments. Both of the V segments, all six of the J segments, and 7 of the 10 D segments that are included in the transgene are used in VDJ joints. In addition, both constant region genes (mu and gamma1) are incorporated into transcripts. The VH105 primer turned out not to be specific for VH105 in the reactions performed. Therefore many of the clones from reactions 3 and 4 contained VH251 transcripts. Additionally, clones isolated from ligated reaction 3 PCR product turned out to encode IgM rather than IgG; however this may reflect contamination with PCR product from reaction 4 as the DNA was isolated on the same gel. An analogous experiment, in which immunoglobulin heavy chain sequences were amplified from adult human peripheral blood lymphocytes (PBL), and the DNA sequence of the VDJ joints determined, was recently reported by Yamada et al. (*J. Exp. Med.* 173: 395–407 (1991), which is incorporated herein by reference). We compared the data from human PBL with our data from the pHC1 transgenic mouse.

TABLE 4

(SEQ ID NO: 121)

| | | | | V | n-D-n |
|---|---|---|---|---|---|
| 1 VH251 | DHQ52 | J3 | γ1 | TACTGTGCGAGA | CGGCTAACTGGGGTTGAT |
| 2 VH251 | DN1 | J4 | γ1 | TACTGTGCGAGA | CACCGTATAGCAGCAGCTGG |
| 3 VH251 | D? | J6 | γ1 | TACTGTGCGAGA | T |
| 4 VH251 | DXP1 | J6 | γ1 | TACTGTGCGAGA | CATTACGATATTTTGACTGGTC |
| 5 VH251 | DXP1 | J4 | γ1 | TACTGTGCGAGA | CGGAGGTACTATGGTTCGGGGAGTTATTATAACGT |
| 6 VH251 | D? | J3 | γ1 | TACTGTGCGAGA | CGGGGGGTGTCTGAT |
| 7 VH251 | DHQ52 | J3 | μ | TACTGTGCGAGA | GCAACTGGC |
| 8 VH251 | DHQ52 | J6 | μ | TACTGTGCGAGA | TCGGCTAACTGGGGATC |
| 9 VH251 | — | J1 | μ | TACTGTGCGAGA | |
| 10 VH251 | DLR2 | J4 | μ | TACTGTGCGAGA | CACGTAGCTAACTCT |
| 11 VH251 | DXP1 | J4 | μ | TACTGTGCGAGA | CAAATTACTATGGTTCGGGGAGTTCC |
| 12 VH251 | D? | J1 | μ | TACTGTGCGAGA | C |
| 13 VH251 | DHQ52 | J6 | μ | TACTGTGCGAGA | CAAACTGGGG |
| 14 VH251 | DXP1 | J6 | μ | TACTGTGCGAGA | CATTACTATGGTTCGGGGAGTTATG |
| 15 VH251 | DXP1 | J4 | γ1 | TACTGTGCGAGA | CAGGGAG |
| 16 VH105 | DXP1 | J5 | μ | TACTGTGTGAGA | TTCTGGGAG |
| 17 VH251 | DXP1 | J4 | γ1 | TACTGTGCGAGA | CGGAGGTACTATGGTTCGGGGAGTTATTATAACGT |
| 18 VH251 | DNQ52 | J4 | γ1 | TACTGTGCGAGA | CAAACCTGGGGAGGA |
| 19 VH251 | DK1 | J6 | γ1 | TACTGTGCGAGA | GGATATAGTGGCTACGATA |
| 20 VH251 | DHQ52 | J4 | μ | TACTGTGCGAGA | CAAACTGGGGAGG |
| 21 VH251 | DK1 | J2 | γ1 | TACTGTGCGAGA | TATAGTGGCTACGATTAC |
| 22 VH251 | DIR2 | J6 | γ1 | TACTGTGCGAGA | GCATCCCTCCCCTCCTTTG |
| 23 VH251 | DIR2 | J1 | μ | TACTGTGCGAGA | CGGGGTGGGGG |
| 24 VH105 | D? | J6 | μ | TACTGYGTG | CCGGTCGAAACT |
| 25 VH105 | DXP1 | J4 | μ | TACTGTGTGAGA | GATATTTTGACTGGTTAACG |
| 26 VH251 | DN1 | J3 | μ | TACTGYGCGAGA | CATGGTATAGCAGCAGCTGGTAC |
| 27 VH105 | DHQ52 | J3 | μ | TACTGTGTGAGA | TCAACTGGGGTTG |
| 28 VH251 | DN1 | J4 | μ | TACTGTGCG | GAAATAGCAGCAGCTGCC |
| 29 VH105 | DN1 | J4 | μ | TACTGTGTG | TGTATAGCAGCAGCTGGTAAAGGAAACGG |
| 30 VH251 | DNQ52 | J4 | μ | TACTGTGCGAGA | CAAACTGGGG |

| | J C |
|---|---|
| 1 | GCTTTTGATATCTGGGGCCAAGGGACAATGGTCACCGTCTCTTCAG CCTCCACCAAG |
| 2 | CTTTTGACTACTGGGGCCAGGGAACCCTGGTCACCGTCTCCTCAG CCTCCACCAAG (SEQ ID NO: 122) |
| 3 | ATTACTACTACTACTACGGTATGGACGTCTGGGGCCAAGGGACCACGGTCACCGTCTCCTCAG CCTCCACCAAG (SEQ ID NO: 123) |
| 4 | CTACTACTACTACGGTATGGACGTCTGGGGCCAAGGGACCACGGTCACCGTCTCCTCAG CCTCCACCAAG (SEQ ID NO: 124) |
| 5 | CTTTGACTACTGGGGCCAGGGAACCCTGGTCACCGTCTCCTCAG CCTCCACCAAG (SEQ ID NO: 125) |
| 6 | GCTTTTGATATCTGGGGCCAAGGGACAATGGTCACCGTCTCTTCAG CCTCCACCAAG (SEQ ID NO: 126) |
| 7 | GCTTTTGATATCTGGGGCCAAGGGACAATGGTCACCGTCTCTTCAG GGAGTGCATCC (SEQ ID NO: 127) |
| 8 | CTACTACTACTACGGTATGGACGTCTGGGGCCAAGGGACCACGGTCACCGTCTCCTCAG GGAGTGCATCC (SEQ ID NO: 128) |
| 9 | TACTTCCAGCACTGGGGCCAGGGCACCCTGGTCACCGTCTCCTCAG GGAGTGCGTCC (SEQ ID NO: 129) |
| 10 | TTTGACTACTGGGGCCAGGGAACCCTGGTCACCGTCTCCTCAG GGAGTGCATCC (SEQ ID NO: 130) |
| 11 | CTTTGACTACTGGGGCCAGGGAACCCTGGTCACCCTCTCCTCAG GGAGTGCATCC (SEQ ID NO: 131) |
| 12 | AATACTTCCAGCACTGGGGCCAGGGCACCCTGGTCACCGTCTCCTCAG GGAGTGCATCC (SEQ ID NO: 132) |
| 13 | ACTACTACTACTACGGTATGGACGTCTGGGGCCAAGGGACCACGGTCACCGTCTCCTCAG GGAGTGCATCC (SEQ ID NO: 133) |
| 14 | ACTACTACTACTACGGTATGGACGTCTGGGGCCAAGGGACCACGGTCACCGTCTCCTCAG GGAGTGCATCC (SEQ ID NO: 134) |
| 15 | TGGGGCCAGGGAACCCTGGTCACCGTCTCCTCAG CCTCCACCAAG (SEQ ID NO: 135) |

TABLE 4-continued (SEQ ID NO: 121)

| | | |
|---|---|---|
| 16 | ACTGGTTCGACCCCTGGGGCCAGGGAACCCTGGTCACCGTCTCCTCAG GGAGTGCATCC | (SEQ ID NO: 136) |
| 17 | CTTTGACTACTGGGGCCAGGGAACCCTGGTCACCGTCTCCTCAG CCTCCACCAAG | (SEQ ID NO: 137) |
| 18 | GACTACTGGGGCCAGGGAACCCTGGTCACCGTCTCCTCAG CCTCCACCAAG | (SEQ ID NO: 138) |
| 19 | ACTACTACTACGGTATGGACGTCTGGGGCCAAGGGACCACGGTCACCGTCTCCTCAG CCTCCACCAAG | (SEQ ID NO: 139) |
| 20 | ACTACTTTGACTACTGGGGCCAGGGAACCCTGGTCACCGTCTCCTCAG GGAGTGCATCC | (SEQ ID NO: 140) |
| 21 | CTACTGGTACTTCGATCTCTGGGGCCGTGGCACCCTGGTCACTGTCTCCTCAG CCTCCACCGAG | (SEQ ID NO: 141) |
| 22 | ACTACTACGGTATGGACGTCTGGGGCCAAGGGACCACGGTCACCGTCTCCTCAG CCTCCACCAAG | (SEQ ID NO: 142) |
| 23 | TTTGACTACTGGGGCCAGGGAACCCTGGTCACCGTCTCCTCAG GGAGTGCATCC | (SEQ ID NO: 143) |
| 24 | TTACTACTACTACTACGGTATGGACGTCTGGGGCCAAGGGACCACGGTCACCGTCTCCTCAG GGAGTGCATCC | (SEQ ID NO: 144) |
| 25 | TGACTACTGGGGCCAGGGAACCCTGGTCACCGTCTCCTCAG GGAGTGCATCC | (SEQ ID NO: 145) |
| 26 | TGCTTTTGATATCTGGGGCCAAGGGACAATGGTCACCGTCTCTTCAG GGAGTGCATCC | (SEQ ID NO: 146) |
| 27 | ATGCTTTTGATATCTGGGGCCAAGGGACAATGGTCACCGTCTCTTCAG GGAGTGCATCC | (SEQ ID NO: 147) |
| 28 | CTACTTTGACTACTGGGGCCAGGGAACCCTGGTCACCGTCTCCTCAG GGAGTGCATCC | (SEQ ID NO: 148) |
| 29 | CTACTGGGGCCAGGGAACCCTGGTCACCGTCTCCTCAG GGAGTGCATCC | (SEQ ID NO: 149) |
| 30 | TGACTACTGGGGCCAGGGAACCCTGGTCACCGTCTCCTCAG GGAGTGCATCC | (SEQ ID NO: 150) |

G. J segment choice

Table 5 compared the distribution of J segments incorporated into pHC1 transgene encoded transcripts to J segments found in adult human PBL immunoglobulin transcripts. The distribution profiles are very similar. J4 is the dominant segment in both systems, followed by J6. J2 is the least common segment in human PBL and the transgenic animal.

TABLE 5

J. Segment Choice

| | Percent Usage (±3%) | |
|---|---|---|
| J. Segment | HC1 transgenic | Human PBL |
| J1 | 7 | 1 |
| J2 | 3 | <1 |
| J3 | 17 | 9 |
| J4 | 44 | 53 |
| J5 | 3 | 15 |
| J6 | 26 | 22 |
| | 100% | 100% |

H. D segment choice

49% (40 of 82) of the clones analyzed by Yamada et al. incorporated D segments that are included in the pHC1 transgene. An additional 11 clones contained sequences that were not assigned by the authors to any of the known D segments. Two of these 11 unassigned clones appear to be derived from an inversion of the DIR2 segments which is included in the pHC1 construct. This mechanism, which was predicted by Ichihara et al. (*EMBO J.* 7: 4141 (1988)) and observed by Sanz (*J. Immunol.* 147: 1720–1729 (1991)), was not considered by Yamada et al. (*J. Exp. Med.* 173: 395–407 (1991)). Table 5 is a comparison of the D segment distribution for the pHC1 transgenic mouse and that observed for human PBL transcripts by Yamada et al. The data of Yamada et al. was recompiled to include DIR2 use, and to exclude D segments that are not in the pHC1 transgene. Table 6 demonstrates that the distribution of D segment incorporation is very similar in the transgenic mouse and in human PBL. The two dominant human D segments, DXP'1 and DN1, are also found with high frequency in the transgenic mouse. The most dramatic dissimilarity between the two distributions is the high frequency of DHQ52 in the transgenic mouse as compared to the human. The high frequency of DHQ52 is reminiscent of the D segment distribution in the human fetal liver. Sanz has observed that 14% of the heavy chain transcripts contained DHQ52 sequences. If D segments not found in pHC1 are excluded from the analysis, 31% of the fetal transcripts analyzed by Sanz contain DHQ52. This is comparable to the 27% that we observe in the pHC1 transgenic mouse.

TABLE 6

D Segment Choice

| | Percent Usage (±3%) | |
|---|---|---|
| D. Segment | HC1 transgenic | Human PBL |
| DLR1 | <1 | <1 |
| DXP1 | 3 | 6 |
| DXP'1 | 25 | 19 |
| DA1 | <1 | 12 |
| DK1 | 7 | 12 |
| DN1 | 12 | 22 |
| DIR2 | 7 | 4 |
| DM2 | <1 | 2 |
| DLR2 | 3 | 4 |
| DHQ52 | 26 | 2 |
| ? | 17 | 17 |
| | 100% | 100% |

I. Functionality of VDJ joints

Table 7 shows the predicted amino acid sequences of the VDJ regions from 30 clones that were analyzed from the pHC1 transgenic. The translated sequences indicate that 23 of the 30 VDJ joints (77%) are in-frame with respect to the variable and J segments.

TABLE 7

Functionality of V-D-J Joints

| | | | FR3 | CDR3 | FR4 | |
|---|---|---|---|---|---|---|
| 1 | VH251 DHQ52 | J3 γ1 | YCAR | RLTGVDAFDI | WGQGTMVTVSSASTK | (SEQ ID NO:71) |
| 2 | VH251 DN1 | J4 γ1 | YCAR | HRIAAAGFDY | WGQGTLVTVSSASTK | (SEQ ID NO:72) |
| 3 | VH251 D? | J6 γ1 | YCAR | YYYYYYGMDV | WGQGTTVTVSSASTK | (SEQ ID NO:73) |
| 4 | VH251 DXP1 | J6 γ1 | YCAR | HYDILTGPTTTTVWTSGAKGPRSPSPQPPP | | (SEQ ID NO:74) |
| 5 | VH251 DXP1 | J4 γ1 | YCAR | RRYYGSGSYYNVFDY | WGQGTLVTVSSASTK | (SEQ ID NO:75) |
| 6 | VH251 D? | J3 γ1 | YCAR | RGVSDAFDI | WGQGTMVTVSSASTK | (SEQ ID NO:76) |
| 7 | VH251 DHQ52 | J3 μ | YCAR | ATGAFDI | WGQGTMVTVSSGSAS | (SEQ ID NO:77) |
| 8 | VH251 DHQ52 | J6 μ | YCAR | SANWGSYYYYGMDV | WGQGTTVTVSSGSAS | (SEQ ID NO:28) |
| 9 | VH251 — | J1 μ | YCAR | YFQH | WGQGTLVTVSSGSAS | (SEQ ID NO:29) |
| 10 | VH251 DLR2 | J4 μ | YCAR | HVANSFDY | WGQGTLVTVSSGSAS | (SEQ ID NO:80) |
| 11 | VH251 DXP1 | J4 μ | YCAR | QITMVRGVPFDY | WGQGTLVTVSSGSAS | (SEQ ID NO:81) |
| 12 | VH251 D? | J1 μ | YCAR | QYFQH | WGQGTLVTVSSGSAS | (SEQ ID NO:82) |
| 13 | VH251 DHQ52 | J6 μ | YCAR | QTGDYYYYGMDV | WGQGTTVTVSSGSAS | (SEQ ID NO:83) |
| 14 | VH251 DXP1 | J6 μ | YCAR | HYYGSGSYDYYYYGMDV | WGQGTTVTVSSGSAS | (SEQ ID NO:84) |
| 15 | VH251 DXP1 | J4 γ1 | YCAR | QGVGPGNPGHRLLSLHQ | | (SEQ ID NO:85) |
| 16 | VH105 DXP1 | J5 μ | YCVR | FWETGSTPGAREPWSPSPQGVH | | (SEQ ID NO:86) |
| 17 | VH251 DXP1 | J4 γ1 | YCAR | RRYYGSGSYYNVFDY | WGQGTLVTVSSASTK | (SEQ ID NO:87) |
| 18 | VH251 DHQ52 | J4 γ1 | YCAR | QTWGGDY | WGQGTLVTVSSASTK | (SEQ ID NO:88) |
| 19 | VH251 DK1 | J6 γ1 | YCAR | GYSGYDNYYYGIHV | WGQGTTVTVSSASTK | (SEQ ID NO:89) |
| 20 | VH251 DHQ52 | J4 μ | YCAR | QTGEDYFDY | WGQGTLVTVSSGSAS | (SEQ ID NO:90) |
| 21 | VH251 DK1 | J2 γ1 | YCAR | YSGYDYLLVLRSLGPWHPGHCLLSLHR | | (SEQ ID NO:91) |
| 22 | VH251 DIR2 | J6 γ1 | YCAR | ASLPSFDYYGMDV | WGQGTTVTVSSASTK | (SEQ ID NO:92) |
| 23 | VH251 DIR2 | J4 μ | YCAR | RGGGLTTGAREPWSPSPQGVH | | (SEQ ID NO:93) |
| 24 | VH105 D? | J6 μ | YCVP | VETLLLLLRYGRLGPRDHGHRLLRECI | | (SEQ ID NO:94) |
| 25 | VH105 DXP1 | J4 μ | YCVR | DILTGZRDY | WGQGTLVTVSSGSAS | (SEQ ID NO:95) |
| 26 | VH251 DM1 | J3 μ | YCAR | HGIAAAGTAFDI | WGQGTMVTVSSGSAS | (SEQ ID NO:96) |
| 27 | VH105 DHQ52 | J3 μ | YCVR | STGVDAFDI | WGQGTMVTVSSGSAS | (SEQ ID NO:97) |
| 28 | VH251 DN1 | J4 μ | YCAE | IAAAALLZLLGPGNPGHRLLRECI | | (SEQ ID NO:98) |
| 29 | VH105 DN1 | J4 μ | YCVC | IAAAGKGNGY | WGQGTLVTVSSGSAS | (SEQ ID NO:99) |
| 30 | VH251 DHQ52 | J4 μ | YCAR | QNWDGY | WGQGTLVTVSSGSAS | (SEQ ID NO:100) |

J. CDR3 length distribution

Table 8 compared the length of the CDR3 peptides from transcripts with in-frame VDJ joints in the pHC1 transgenic mouse to those in human PBL. Again the human PBL data comes from Yamada et al. The profiles are similar with the transgenic profile skewed slightly toward smaller CDR3 peptides than observed from human PBL. The average length of CDR3 in the transgenic mouse is 10.3 amino acids. This is substantially the same as the average size reported for authentic human CDR3 peptides by Sanz (*J. Immunol.* 147: 1720–1729 (1991)).

TABLE 8

CDR3 Length Distribution

| | Percent Occurrence (±3%) | |
|---|---|---|
| #amino acids in CDR3 | HC1 transgenic | Human PBL |
| 3–8 | 26 | 14 |
| 9–12 | 48 | 41 |
| 13–18 | 26 | 37 |
| 19–23 | <1 | 7 |
| >23 | <1 | 1 |
| | 100% | 100% |

EXAMPLE 13

Rearranged Heavy Chain Transgenes

A. Isolation of Rearranged Human Heavy Chain VDJ segments.

Two human leukocyte genomic DNA libraries cloned into the phage vector μEMBL3/SP6/T7 (Clonetech Laboratories, Inc., Palo Alto, Calif.) are screened with a 1 kb PacI/HindIII fragment of 11.3 containing the human heavy chain J-μ intronic enhancer. Positive clones are tested for hybridization with a mixture of the following $V_H$ specific oligonucleotides:

oligo-7 5'-tca gtg aag gtt tcc tgc aag gca tct gga tac acc ttc acc-3'(SEQ ID NO:105)

oligo-8 5'-tcc ctg aga ctc tcc tgt gca gcc tct gga ttc acc ttc agt-3'(SEQ ID NO:106)

Clones that hybridized with both V and J-μ probes are isolated and the DNA sequence of the rearranged VDJ segment determined.

B. Construction of rearranged human heavy chain transgenes

Fragments containing functional VJ segments (open reading frame and splice signals) are subcloned into the plasmid vector pSP72 such that the plasmid derived XhoI site is adjacent to the 5' end of the insert sequence. A subclone containing a functional VDJ segment is digested with XhoI and PacI (PacI, a rare-cutting enzyme, recognizes a site near the J-m intronic enhancer), and the insert cloned into XhoI/PacI digested pHC2 to generate a transgene construct with a functional VDJ segment, the J-μ intronic enhancer, the μ switch element, the μ constant region coding exons, and the γ1 constant region, including the sterile transcript associated sequences, the γ1 switch, and the coding exons. This transgene construct is excised with NotI and microinjected into the pronuclei of mouse embryos to generate transgenic animals as described above.

EXAMPLE 14

Light Chain Transgenes

A. Construction of Plasmid vectors

1. Plasmid vector pGP1c

Plasmid vector pGP1a is digested with NotI and the following oligonucleotides ligated in:

oligo-81 5'-ggc cgc atc ccg ggt ctc gag gtc gac aag ctt tcg agg atc cgc-3'(SEQ ID NO:107)

oligo-82 5'-ggc cgc gga tcc tcg aaa gct tgt cga cct cga gac ccg gga tgc-3'(SEQ ID NO:108)

The resulting plasmid, pGP1c, contains a polylinker with XmaI, XhoI, SalI, HindIII, and BamHI restriction sites flanked by NotI sites.

2. Plasmid vector pGP1d

Plasmid vector pGP1a is digested with NotI and the following oligonucleotides ligated in:

oligo-87 5'-ggc cgc tgt cga caa gct tat cga tgg atc ctc gag tgc -3'(SEQ ID NO:109)

oligo-88 5'-ggc cgc act cga gga tcc atc gat aag ctt gtc gac agc -3'(SEQ ID NO:110)

The resulting plasmid, pGP1d, contains a polylinker with SalI, HindIII, ClaI, BamHI, and XhoI restriction sites flanked by NotI sites.

B. Isolation of Jκ and Cκ clones

A human placental genomic DNA library cloned into the phage vector λEMBL3/SP6/T7 (Clonetech Laboratories, Inc., Palo Alto, Calif.) was screened with the human kappa light chain J region specific oligonucleotide:

oligo-36 5'- cac ctt cgg cca agg gac acg act gga gat taa acg taa gca -3'(SEQ ID NO:111)

and the phage clones 136.2 and 136.5 isolated. A 7.4 kb XhoI fragment that includes the Jκ1 segment was isolated from 136.2 and subcloned into the plasmid pNN03 to generate the plasmid clone p36.2. A neighboring 13 kb XhoI fragment that includes Jk segments 2 through 5 together with the $C_\kappa$ gene segment was isolated from phage clone 136.5 and subcloned into the plasmid pNN03 to generate the plasmid clone p36.5. Together these two clones span the region beginning 7.2 kb upstream of Jκ1 and ending 9 kb downstream of $C_\kappa$.

C. Construction of rearranged light chain transgenes 1. pCK1, a Cκ vector for expressing rearranged variable segments The 13 kb XhoI insert of plasmid clone p36.5 containing the Cκ gene, together with 9 kb of downstream sequences, is cloned into the SalI site of plasmid vector pGP1c with the 5' end of the insert adjacent to the plasmid XhoI site. The resulting clone, pCK1 can accept cloned fragments containing rearranged VJκ segments into the unique 5' XhoI site. The transgene can then be excised with NotI and purified from vector sequences by gel electrophoresis. The resulting transgene construct will contain the human J-Cκ intronic enhancer and may contain the human 3' κ enhancer.

2. pCK2, a Cκ vector with heavy chain enhancers for expressing rearranged variable segments A 0.9 kb XbaI fragment of mouse genomic DNA containing the mouse heavy chain J-µ intronic enhancer (J. Banerji et al., *Cell* 33: 729–740 (1983)) was subcloned into pUC18 to generate the plasmid pJH22.1. This plasmid was linearized with SphI and the ends filled in with Klenow enzyme. The Klenow treated DNA was then digested with HindIII and a 1.4 kb MluI/HindIII fragment of phage clone 11.3 (previous example), containing the human heavy chain J-µ intronic enhancer (Hayday et al., *Nature* 307: 334–340 (1984)), to it. The resulting plasmid, pMHE1, consists of the mouse and human heavy chain J-µ intronic enhancers ligated together into pUC18 such that they are excised on a single BamHI/HindIII fragment. This 2.3 kb fragment is isolated and cloned into pGP1c to generate pMHE2. pMHE2 is digested with SalI and the 13 kb XhoI insert of p36.5 cloned in. The resulting plasmid, pCK2, is identical to pCK1, except that the mouse and human heavy chain J-µ intronic enhancers are fused to the 3' end of the transgene insert. To modulate expression of the final transgene, analogous constructs can be generated with different enhancers, i.e. the mouse or rat 3' kappa or heavy chain enhancer (Meyer and Neuberger, *EMBO J.*, 8: 1959–1964 (1989); Petterson et al., *Nature*, 344: 165–168 (1990)).

3. Isolation of rearranged kappa light chain variable segments

Two human leukocyte genomic DNA libraries cloned into the phage vector λEMBL3/SP6/T7 (Clonetech Laboratories, Inc., Palo Alto, Calif.) were screened with the human kappa light chain J region containing 3.5 kb XhoI/SmaI fragment of p36.5. Positive clones were tested for hybridization with the following Vκ specific oligonucleotide:

oligo-65 5'-agg ttc agt ggc agt ggg tct ggg aca gac ttc act ctc acc atc agc-3'(SEQ ID NO:112)

Clones that hybridized with both V and J probes are isolated and the DNA sequence of the rearranged VJκ segment determined.

4. Generation of transgenic mice containing rearranged human light chain constructs.

Fragments containing functional VJ segments (open reading frame and splice signals) are subcloned into the unique XhoI sites of vectors pCK1 and pCK2 to generate rearranged kappa light chain transgenes. The transgene constructs are isolated from vector sequences by digestion with NotI. Agarose gel purified insert is microinjected into mouse embryo pronuclei to generate transgenic animals. Animals expressing human kappa chain are bred with heavy chain minilocus containing transgenic animals to generate mice expressing fully human antibodies.

Because not all VJκ combinations may be capable of forming stable heavy-light chain complexes with a broad spectrum of different heavy chain VDJ combinations, several different light chain transgene constructs are generated, each using a different rearranged VJk clone, and transgenic mice that result from these constructs are bred with heavy chain minilocus transgene expressing mice. Peripheral blood, spleen, and lymph node lymphocytes are isolated from double transgenic (both heavy and light chain constructs) animals, stained with fluorescent antibodies specific for human and mouse heavy and light chain immunoglobulins (Pharmingen, San Diego, Calif.) and analyzed by flow cytometry using a FACScan analyzer (Becton Dickinson, San Jose, Calif.). Rearranged light chain transgenes constructs that result in the highest level of human heavy/light chain complexes on the surface of the highest number of B cells, and do not adversely affect the immune cell compartment (as assayed by flow cytometric analysis with B and T cell subset specific antibodies), are selected for the generation of human monoclonal antibodies.

D. Construction of unrearranged light chain minilocus transgenes 1. pJCK1, a Jκ, Cκ containing vector for constructing minilocus transgenes The 13 kb Cκ containing XhoI insert of p36.5 is treated with Klenow enzyme and cloned into HindIII digested, Klenow-treated, plasmid pGP1d. A plasmid clone is selected such that the 5' end of the insert is adjacent to the vector derived ClaI site. The resulting plasmid, p36.5-1d, is digested with ClaI and Klenow-treated. The Jκ1 containing 7.4 kb XhoI insert of p36.2 is then Klenow-treated and cloned into the ClaI, Klenow-treated p36.5-1d. A clone is selected in which the p36.2 insert is in the same orientation as the p36.5 insert. This clone, pJCK1 (FIG. 34), contains the entire human Jκ region and Cκ, together with 7.2 kb of upstream sequences and 9 kb of downstream sequences. The insert also contains the human J-Cκ intronic enhancer and may contain a human 3' κ enhancer. The insert is flanked by a unique 3' SalI site for the purpose of cloning additional 3' flanking sequences such as heavy chain or light chain enhancers. A unique XhoI site is located at the 5' end of the insert for the purpose of cloning in unrearranged Vκ gene segments. The unique SalI and XhoI sites are in turn flanked by NotI sites that are used to isolate the completed transgene construct away from vector sequences.

2. Isolation of unrearranged Vκ gene segments and generation of transgenic animals expressing human Ig light chain protein The Vκ specific oligonucleotide, oligo-65 (discussed above), is used to probe a human placental genomic DNA library cloned into the phage vector 1EMBL3/SP6/T7 (Clonetech Laboratories, Inc., Palo Alto, Calif.). Variable gene segments from the resulting clones are sequenced, and clones that appear functional are selected. Criteria for judging functionality include: open reading frames, intact splice acceptor and donor sequences, and intact recombination sequence. DNA fragments containing selected variable gene segments are cloned into the unique XhoI site of plasmid pJCK1 to generate minilocus constructs. The resulting clones are digested with NotI and the inserts isolated and injected into mouse embryo pronuclei to generate transgenic animals. The transgenes of these animals will undergo V to J joining in developing B-cells. Animals expressing human kappa chain are bred with heavy chain minilocus containing transgenic animals to generate mice expressing fully human antibodies.

EXAMPLE 15

Genomic Heavy Chain Human Ig Transgene

This Example describes the cloning of a human genomic heavy chain immunoglobulin transgene which is then introduced into the murine germline via microinjection into zygotes or integration in ES cells.

Nuclei are isolated from fresh human placental tissue as described by Marzluff, W. F., et al. (1985), *Transcription and Translation: A Practical Approach*, B. D. Hammes and S. J. Higgins, eds., pp. 89–129, IRL Press, Oxford). The isolated nuclei (or PBS washed human spermatocytes) are embedded in 0.5% low melting point agarose blocks and lysed with 1 mg/ml proteinase K in 500 mM EDTA, 1% SDS for nuclei, or with 1 mg/ml proteinase K in 500 mM EDTA, 1% SDS, 10 mM DTT for spermatocytes at 50° C. for 18 hours. The proteinase K is inactivated by incubating the blocks in 40 µg/ml PMSF in TE for minutes at 50° C., and then washing extensively with TE. The DNA is then digested in the agarose with the restriction enzyme NotI as described by M. Finney in *Current Protocols in Molecular Biology* (F. Ausubel et al., eds. John Wiley & Sons, Supp. 4, 1988, e.g., Section 2.5.1).

The NotI digested DNA is then fractionated by pulsed field gel electrophoresis as described by Anand et al., *Nuc. Acids Res.* 17: 3425–3433 (1989). Fractions enriched for the NotI fragment are assayed by Southern hybridization to detect one or more of the sequences encoded by this fragment. Such sequences include the heavy chain D segments, J segments, and γ1 constant regions together with representatives of all 6 $V_H$ families (although this fragment is identified as 670 kb fragment from HeLa cells by Berman et al. (1988), supra., we have found it to be an 830 kb fragment from human placental and sperm DNA). Those fractions containing this NotI fragment are ligated into the NotI cloning site of the vector pYACNN as described (McCormick et al., *Technique* 2: 65–71 (1990)). Plasmid pYACNN is prepared by digestion of pYACneo (Clontech) with EcoRI and ligation in the presence of the oligonucleotide 5' - AAT TGC GGC CGC - 3'(SEQ ID NO:113).

YAC clones containing the heavy chain NotI fragment are isolated as described by Traver et al., *Proc. Natl. Acad. Sci. USA*, 86: 5898–5902 (1989). The cloned NotI insert is isolated from high molecular weight yeast DNA by pulse field gel electrophoresis as described by M. Finney, op. cit. The DNA is condensed by the addition of 1 mM spermine and microinjected directly into the nucleus of single cell embryos previously described. Alternatively, the DNA is isolated by pulsed field gel electrophoresis and introduced into ES cells by lipofection (Gnirke et al., *EMBO J.* 10: 1629–1634 (1991)), or the YAC is introduced into ES cells by spheroplast fusion.

EXAMPLE 16

Discontinuous Genomic Heavy Chain Ig Transgene

An 85 kb SpeI fragment of human genomic DNA, containing $V_H6$, D segments, J segments, the µ constant region and part of the γ constant region, has been isolated by YAC cloning essentially as described in Example 1. A YAC carrying a fragment from the germline variable region, such as a 570 kb NotI fragment upstream of the 670–830 kb NotI fragment described above containing multiple copies of $V_1$ through $V_5$, is isolated as described. (Berman et al. (1988), supra, detected two 570 kb NotI fragments, each containing multiple V segments.) The two fragments are coinjected into the nucleus of a mouse single cell embryo as described in Example 1.

Typically, coinjection of two different DNA fragments result in the integration of both fragments at the same insertion site within the chromosome. Therefore, approximately 50% of the resulting transgenic animals that contain at least one copy of each of the two fragments will have the V segment fragment inserted upstream of the constant region containing fragment. Of these animals, about 50% will carry out V to DJ joining by DNA inversion and about 50% by deletion, depending on the orientation of the 570 kb NotI fragment relative to the position of the 85 kb SpeI fragment. DNA is isolated from resultant transgenic animals and those animals found to be containing both transgenes by Southern blot hybridization (specifically, those animals containing both multiple human V segments and human constant region genes) are tested for their ability to express human immunoglobulin molecules in accordance with standard techniques.

EXAMPLE 17

Identification of functionally rearranged variable region sequences in transgenic B cells An antigen of interest is used to immunize (see Harlow and Lane, *Antibodies: A Laboratory Manual*, Cold Spring Harbor, N.Y. (1988)) a mouse with the following genetic traits: homozygosity at the endogenous having chain locus for a deletion of $J_H$ (Examples 10); hemizygous for a single copy of unrearranged human heavy chain minilocus transgene (examples 5 and 14); and hemizygous for a single copy of a rearranged human kappa light chain transgene (Examples 6 and 14).

Following the schedule of immunization, the spleen is removed, and spleen cells used to generate hybridomas. Cells from an individual hybridoma clone that secretes antibodies reactive with the antigen of interest are used to prepare genomic DNA. A sample of the genomic DNA is digested with several different restriction enzymes that recognize unique six base pair sequences, and fractionated on an agarose gel. Southern blot hybridization is used to identify two DNA fragments in the 2–10 kb range, one of which contains the single copy of the rearranged human heavy chain VDJ sequences and one of which contains the single copy of the rearranged human light chain VJ sequence. These two fragments are size fractionated on agarose gel and cloned directly into pUC18. The cloned inserts are then subcloned respectively into heavy and light chain expression cassettes that contain constant region sequences.

The plasmid clone pγe1 (Example 12) is used as a heavy chain expression cassette and rearranged VDJ sequences are cloned into the XhoI site. The plasmid clone pCK1 is used as a light chain expression cassette and rearranged VJ sequences are cloned into the XhoI site. The resulting clones are used together to transfect SP$_O$ cells to produce antibodies that react with the antigen of interest (Co. et al., Proc. Natl. Acad. Sci. USA 88: 2869 (1991), which is incorporated herein by reference).

Alternatively, mRNA is isolated from the cloned hybridoma cells described above, and used to synthesize cDNA. The expressed human heavy and light chain VDJ and VJ sequence are then amplified by PCR and cloned (Larrick et al., Biol. Technology, 7: 934–938 (1989)). After the nucleotide sequence of these clones has been determined, oligonucleotides are synthesized that encode the same polypeptides, and synthetic expression vectors generated as described by Queen et al., Proc. Natl. Acad. Sci. USA., 84: 5454–5458 (1989).

The foregoing description of the preferred embodiments of the present invention has been presented for purposes of illustration and description. They are not intended to be exhaustive or to limit the invention to the precise form disclosed, and many modifications and variations are possible in light of the above teaching.

All publications and patent applications herein are incorporated by reference to the same extent as if each individual publication or patent application was specifically and individually indicated to be incorporated by reference.

Such modifications and variations which may be apparent to a person skilled in the art are intended to be within the scope of this invention.

EXAMPLE 18

Reduction of Endogenous Mouse Immunoglobulin Expression by Antisense RNA

A. Vector for Expression of Antisense Ig Sequences

1. Construction of the cloning vector pGP1h

The vector pGP1b (referred to in a previous example) is digested with XhoI and BamHI and ligated with the following oligonucleotides:

5'- gat cct cga gac cag gta cca gat ctt gtg aat tcg -3'(SEQ ID NO:114)

5'- tcg acg aat tca caa gat ctg gta cct ggt ctc gag -3'(SEQ ID NO:115)

to generate the plasmid pGP1h. This plasmid contains a polylinker that includes the following restriction sites: NotI, EcoRI, BglII, Asp718, XhoI, BamHI, HindIII, NotI.

Construction of pBCE1.

A 0.8 kb XbaI/BglII fragment of pVH251 (referred to in a previous example), that includes the promoter leader sequence exon, first intron, and part of the second exon of the human VH-V family immunoglobulin variable gene segment, was inserted into XbaI/BglII digested vector pNNO3 to generate the plasmid pVH251.

The 2.2 kb BamHI/EcoRI DNA fragment that includes the coding exons of the human growth hormone gene (hGH; Seeburg, (1982) DNA 1: 239–249) is cloned into BglII/EcoRI digested pGH1h. The resulting plasmid is digested with BamHI and the BamHI/BglII of pVH251N is inserted in the same orientation as the hGH gene to generate the plasmid pVhgh.

A 0.9 kb XbaI fragment of mouse genomic DNA containing the mouse heavy chain J-μ intronic enhancer (Banerji et al., (1983) Cell 33: 729–740) was subcloned into pUC18 to generate the plasmid pJH22.1. This plasmid was linearized with SphI and the ends filled in with klenow enzyme. The klenow treated DNA was then digested with HindIII and a 1.4 kb MluI(klenow)/HindIII fragment of phage clone λ1.3 (previous example), containing the human heavy chain J-μ intronic enhancer (Hayday et al., (1984) Nature 307: 334–340), to it. The resulting plasmid, pMHE1, consists of the mouse and human heavy chain J-μ intron enhancers ligated together into pUC18 such that they can be excised on a single BamHI/HindIII fragment.

The BamHI/HindIII fragment of pMHE1 is cloned into BamHI/HindIII cut pvhgh to generate the B-cell expression vector pBCE1. This vector, depicted in FIG. 37, contains unique XhoI and Asp718 cloning sites into which antisense DNA fragments can be cloned. The expression of these antisense sequences is driven by the upstream heavy chain promoter-enhancer combination the downstream hGH gene sequences provide polyadenylation sequences in addition to intron sequences that promote the expression of transgene constructs. Antisense transgene constructs generated from pBCE1 can be separated from vector sequences by digestion with NotI.

B. An IgM antisense transgene construct.

The following two oligonucleotides:

5'- cgc ggt acc gag agt cag tcc ttc cca aat gtc -3'(SEQ ID NO:116)

5'- cgc ctc gag aca gct gga atg ggc aca tgc aga -3'(SEQ ID NO:117)

are used as primers for the amplification of mouse IgM constant region sequences by polymerase chain reaction (PCR) using mouse spleen cDNA as a substrate. The resulting 0.3 kb PCR product is digested with Asp718 and XhoI and cloned into Asp718/XhoI digested pBCE1 to generate the antisense transgene construct pMAS1. The purified NotI insert of pMAS1 is microinjected into the pronuclei of half day mouse embryos—alone or in combination with one or more other transgene constructs—to generate transgenic mice. This construct expresses an RNA transcript in B-cells that hybridizes with mouse IgM mRNA, thus downregulating the expression of mouse IgM protein. Double transgenic mice containing pMAS1 and a human heavy chain transgene minilocus such as pHC1 (generated either by coinjection of both constructs or by breeding of singly transgenic mice) will express the human transgene encoded Ig receptor on a higher percentage of B-cell than mice transgenic for the human heavy chain minilocus alone. The ratio of human to mouse Ig receptor expressing cells is due in part to competition between the two populations for factors and cells that promoter B-cell differentiation and expansion. Because the Ig receptor plays a key role in B-cell development, mouse Ig receptor expressing B-cells that express reduced levels of IgM on their surface (due to mouse Ig specific antisense down-regulation) during B-cell development will not compete as well as cells that express the human receptor.

C. An IgKappa antisense transgene construct.

The following two oligonucleotides:

5'- cgc ggt acc gct gat gct gca cca act gta tcc -3'(SEQ ID NO:118)

5'- cgc ctc gag cta aca ctc att cct gtt gaa gct -3'(SEQ ID NO:119)

are used as primers for the amplification of mouse IgKappa constant region sequences by polymerase chain reaction (PCR) using mouse spleen cDNA as a substrate. The resulting 0.3 kb PCR product is digested with Asp718 and XhoI and cloned into Asp718/XhoI digested pBCE1 to generate the antisense transgene construct pKAS1. The purified NotI insert of pKAS1 is microinjected into the pronuclei of half day mouse embryos—alone or in combination with one or more other transgene constructs—to generate transgenic mice. This construct expresses an RNA transcript in B-cells that hybridizes with mouse IgK mRNA, thus down-regulating the expression of mouse IgK protein as described above for pMAS1.

What is claimed is:

1. A transgenic mouse having DNA segments from a human immunoglobulin gene locus incorporated into the germline DNA of the transgenic mouse such that the transgenic mouse develops primary response B cells expressing IgM and secondary response B cells expressing somatically mutated, substantially human IgO, the germline DNA of said transgenic mouse comprises:

an unrearranged human immunoglobulin locus obtained from one or more YAC DNA segments comprising a plurality of human heavy chain V gene segments, a plurality of human heavy chain D gene segments, a plurality of human heavy chain J gene segments, a mu constant region comprised of a μ switch region located upstream from a μ coding segment, and a gamma constant region comprised of a γ switch region located upstream from a human γ coding segment, wherein the γ constant region is in closer proximity to the μ constant region that in the naturally-occurring germline human immunoglobulin gene locus;

said primary response B cells expressing IgM having chromosomal DNA comprised of said mu coding region and said human gamma coding region and a rearranged variable region which is comprised of a VDJ rearrangement of said unrearranged human immunoglobulin minilocus, said rearranged variable region having N-region nucleotides at recombination joints between said human heavy chain V gene segments and human D gene segments and between said human D gene segments and said human heavy chain J segments, and therein FR1, FR2, FR3, CDR1, and CDR2 portions of said rearranged variable region consist essentially of DNA sequences from said human heavy chain V gene segments of said unrearranged human immunoglobulin locus;

said secondary response B cells having chromosomal DNA comprised of a class switch recombination from said mu constant region to said gamma constant region, and said rearranged variable region; wherein FR1, FR2, FR3, CDR1, and CDR2 portions of said rearranged variable region include a plurality of DNA sequences not from said human heavy chain V segments of said unrearranged human immunoglobulin locus not identical to corresponding segments in the immunoglobulin gene locus.

2. The transgenic mouse of claim 1 wherein the human immunoglobulin locus is comprised of between 2 and 4 human V segments, between 2 and 15 human D segments, and between 2 and 6 human J segments.

3. The transgenic mouse of claim 1 wherein the unrearranged human immunoglobulin locus contains a discontinuity between the μ coding region and the γ switch region.

4. The transgenic mouse of claim 1, wherein the entire unrearranged immunoglobulin gene locus is obtained from YAC DNA segments.

5. The transgenic mouse of claim 1, wherein said human IgG comprises a human kappa light chain encoded by a human kappa immunoglobulin locus obtained from one or more YAC DNA segments.

* * * * *